US008895804B2

(12) United States Patent
Frohberg et al.

(10) Patent No.: US 8,895,804 B2
(45) Date of Patent: *Nov. 25, 2014

(54) PLANTS WITH INCREASED ACTIVITY OF A STARCH PHOSPHORYLATING ENZYME

(75) Inventors: Claus Frohberg, Kleinmachnow (DE); Oliver Koetting, Zürich (CH); Gerhard Ritte, Postdam (DE); Martin Steup, Berlin (DE)

(73) Assignee: Bayer Cropscience AG, Monheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/174,228

(22) Filed: Jun. 30, 2011

(65) Prior Publication Data

US 2012/0017333 A1     Jan. 19, 2012

Related U.S. Application Data

(62) Division of application No. 12/774,420, filed on May 5, 2010, now Pat. No. 8,007,592, which is a division of application No. 10/591,428, filed as application No. PCT/EP2005/002449 on Mar. 4, 2005, now Pat. No. 7,772,463.

(60) Provisional application No. 60/549,945, filed on Mar. 5, 2004.

(30) Foreign Application Priority Data

Mar. 5, 2004   (EP) ...................................... 04090086
Mar. 29, 2004   (EP) ...................................... 04090121

(51) Int. Cl.
| | |
|---|---|
| *C12N 15/82* | (2006.01) |
| *C12N 15/00* | (2006.01) |
| *C12N 15/29* | (2006.01) |
| *C12N 15/63* | (2006.01) |
| *A01H 5/00* | (2006.01) |
| *B02C 9/00* | (2006.01) |
| *C12N 9/12* | (2006.01) |

(52) U.S. Cl.
CPC ... *B02C 9/00* (2013.01); *C12N 9/12* (2013.01); *C12N 9/1205* (2013.01); *C12N 15/8245* (2013.01)
USPC ........... 800/284; 800/278; 800/296; 435/183; 435/320.1; 435/410; 435/468; 536/23.1; 536/23.2; 536/23.6

(58) Field of Classification Search
None
See application file for complete search history.

(56) References Cited

U.S. PATENT DOCUMENTS

| | | | |
|---|---|---|---|
| 5,855,946 A | 1/1999 | Seib et al. | |
| 6,428,886 B1 | 8/2002 | Lewis et al. | |
| 6,521,816 B1 | 2/2003 | Frohberg | |
| 7,772,463 B2 | 8/2010 | Frohberg et al. | |
| 7,842,853 B2 | 11/2010 | Uwer et al. | |
| 7,932,436 B2 * | 4/2011 | Frohberg et al. | 800/284 |
| 2002/0160378 A1 * | 10/2002 | Harper et al. | 435/6 |
| 2006/0123505 A1 | 6/2006 | Kikuchi et al. | |

FOREIGN PATENT DOCUMENTS

| | | |
|---|---|---|
| WO | WO 96/27674 | 9/1996 |
| WO | WO 97/11188 | 3/1997 |
| WO | WO 00/77229 | 12/2000 |
| WO | WO 02/10210 | 2/2002 |
| WO | WO 02/22675 | 3/2002 |
| WO | WO 02/34923 | 5/2002 |
| WO | WO 2005/095632 | 10/2005 |

OTHER PUBLICATIONS

Alonso et al.(Aug. 1, 2003) "Genome-Wide Insertional Mutagenesis of *Arabidopsis* Thaliana" *Science* 301:653-657.
Baunsgaard et al. (2005) "A novel Isoform of Glucan, Water Dikinase Phosphorylates Pre-Phosphorylated α-glucans and is Involved in Starch Degradation in *Arabidopsis*." *The Plant Journal*, vol. 41, pp. 595 -605.
Blennow et al. (2000) "Starch Molecular Structure and Phosphorylation Investigated by a Combined Chromatographic and Chemometric Approach." *Carbohydrate Polymers*, vol. 41, pp. 163-174.
Blennow et al. (2000) "The Distribution of Covalendy Bound Phosphate in the Starch Granule in Relation to Starch Crystanallity." *International Journal of Biological Macromolecules*, vol. 27, pp. 211-218.
Blennow et al. (Oct. 2002) "Starch Phosphorylation: a New Front Line in Starch Research." *Trends in Plant Science*, vol. 7, No. 10, pp. 445-450.
GenBank Accession No. AF312027 (Aug. 24, 2001).
GenBank Accession No. AR400184 (Dec. 18, 2003).

(Continued)

*Primary Examiner* — Brent T Page
(74) *Attorney, Agent, or Firm* — Hunton & Williams LLP

(57) ABSTRACT

The present invention relates to plant cells and plants, which are genetically modified, whereby the genetic modification leads to an increase in the activity of a starch-phosphorylating OK1 protein in comparison to the corresponding wild type plant cells or wild type plants that have not been genetically modified. In addition, the present invention concerns means and methods for the manufacture of such plant cells and plants. These types of plant cells and plants synthesize a modified starch. Therefore, the present invention also concerns the starches synthesized from the plant cells and plants according to the invention, methods for manufacturing these starches, and the manufacture of starch derivatives of these modified starches, as well as flours containing starches according to the invention.

Furthermore, the present invention also relates to nucleic acids, coding starch-phosphorylating OK1 proteins, vectors, host cells, plant cells, and plants containing such nucleic acid molecules. In addition, the present invention relates to OK1 proteins that have starch-phosphorylating activity.

46 Claims, 6 Drawing Sheets

(56) References Cited

OTHER PUBLICATIONS

GenBank Accession No. AR400813 (Dec. 18, 2003).
GenBank Accession No. AR400815 (Dec. 18, 2003).
GenBank Accession No. AY027522 (Feb. 26, 2001).
GenBank Accession No. AY094062 (Jul. 23, 2003).
GenBank Accession No. AY747068 (Mar. 1, 2005).
GenBank Accession No. Y09533 (Jul. 22, 2003).
GenPept Accession No. AAN93923 (Dec. 20, 2002).
GenPept Accession No. AAR61444 (Dec. 18, 2003).
GenPept Accession No. AAR61445 (Dec. 18, 2003).
GenPept Accession No. AAR61446 (Dec. 18, 2003).
GenPept Accession No. AR236165 (Dec. 20, 2002).
GenPept Accession No. B29959 (Jun. 18, 1999).
GenPept Accession No. S01446 (Jul. 21, 2000).
Hejazi et al., *The Plant Journal*, vol. 55, pp. 323-334 (2008).
Jane et al. (Nov./Dec. 1996) "Phosphorus in Rice and Other Starches." *Cereal Foods World*, vol. 41, No. 11, pp. 827-832.
Köotting et al. (Jan. 2005) "Identification of a Novel Enzyme Required for Starch Metabolism in *Arabidopsis* Leaves. The Phosphoglucan, Water Dikinase [1] [w1]". *Plant Physiology*, vol. 137, pp. 242-252.
Lorberth et al. (May 1998) "Inhibition of a Starch-Granule-Bound Protein Leads to Modified Starch and Repression of Cold of Sweetening." *Nature Biotechnology*, vol. 16, pp. 473-477.
Mikkelsen et al. (2004) "Functional Characterization of □-glucan, Water Dikinase, the Starch Phosphorylating Enzyme." *Biochem. J.*, vol. 377, pp. 525-532.

Ritte, et al. (2000) "Compartmentation of the Starch-Related R1 Protein in Higher Plants." *Starch/Stärke*, vol. 52, pp. 179- 185.
Ritte et al. (2003) "Determination of the starch-phosphorylating enzyme activity in plant extracts." *Planta*, vol. 216, No. 5, pp. 798-801.
Ritte, et al. (May 14, 2002) "The starch-related R1 protein is an α-glucan, water dikinase." *PNAS*, vol. 99, No. 10, pp. 7166-7171.
Ritte, et al., *FEBS Letters*, vol. 580,.pp. 4872-4876 (2006).
Sitohy et al. (2000) "Optimizing the Conditions for Starch Dry Phosphorylation with Sodium Mono-and Dihydrogen Orthophosphateunder Heat and Vacuum." *Starch/Stärke*, vol. 52, No. 4, pp. 95-100.
Tabata et al. (1971) "Studies on Starch 272 Phosphate." *Starch/Stärke*, vol. 23, pp. 267-272.
UniProtKB/Swiss-Prot entry Q6ZY51 (Jun. 13, 2006).
UniProtKB/TrEMBL entry Q84T18 (Jun. 1, 2003).
Yu et. at (Aug. 2001) "The *Arabidopsis* sex1 Mutant is Defective in the R1 Protein, a General Regulator of Starch Degradation in Plants, and Not in the Chloroplast Hexose Transporter." *The Plant Cell*, vol. 13, pp. 1907-1918.
International Search Report for International Application No. PCT/EP2005/002449 mailed Jan. 9, 2006.
Written Opinion for International Application No. PCT/EP2005/002449 mailed Jan. 9, 2006.
International Preliminary Report on Patentability for International Application No. PCT/EP2005/002449 completed May 12, 2006.

* cited by examiner

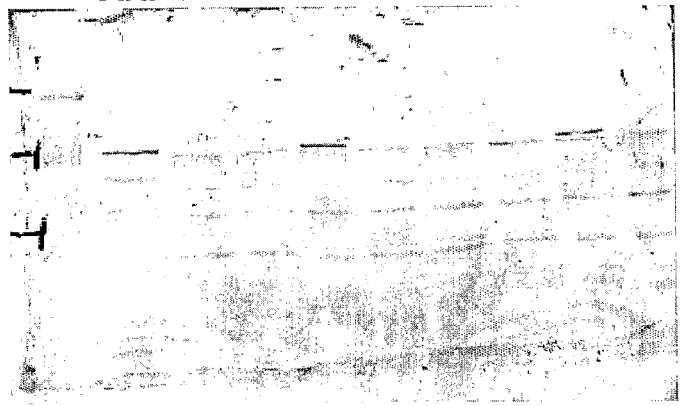
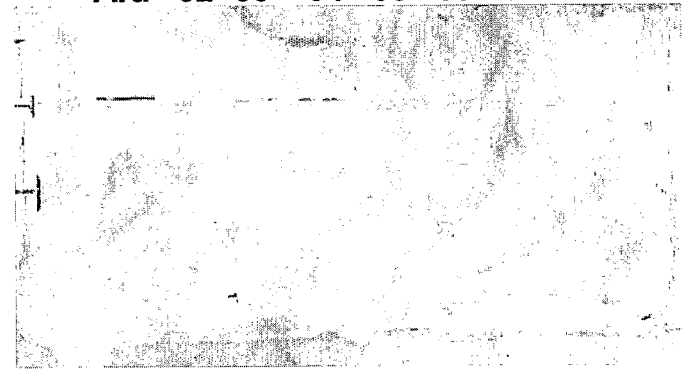
Fig. 7

SEQUENCE LISTING

```
<160> NUMBER OF SEQ ID NOS: 25

<210> SEQ ID NO 1
<211> LENGTH: 3591
<212> TYPE: DNA
<213> ORGANISM: Arabidopsis thaliana
<220> FEATURE:
<221> NAME/KEY: CDS
<222> LOCATION: (1)..(3591)
<223> OTHER INFORMATION:

<400> SEQUENCE: 1 atg gag agc att ggc agc cat tgt tgc agc tct cct ttc acc ttc atc        48
Met Glu Ser Ile Gly Ser His Cys Cys Ser Ser Pro Phe Thr Phe Ile
1               5                   10                  15 act aga aac tca tca tca tca ctt cct aga ctc gtt aac atc act cac        96
Thr Arg Asn Ser Ser Ser Ser Leu Pro Arg Leu Val Asn Ile Thr His
            20                  25                  30
```

```
aga gtt aat ctc agc cac caa tct cac cga ctc aga aac tcc aat tct    144
Arg Val Asn Leu Ser His Gln Ser His Arg Leu Arg Asn Ser Asn Ser
         35                  40                  45 cgt ctc act tgc act gct act tct tct tcc acc att gag gaa caa cgg    192
Arg Leu Thr Cys Thr Ala Thr Ser Ser Ser Thr Ile Glu Glu Gln Arg
 50                  55                  60 aag aag aaa gat gga tca gga acg aaa gtg agg ttg aat gtg agg tta    240
Lys Lys Lys Asp Gly Ser Gly Thr Lys Val Arg Leu Asn Val Arg Leu
 65                  70                  75                  80 gat cat caa gtt aat ttt ggt gac cat gtg gct atg ttt gga tca gct    288
Asp His Gln Val Asn Phe Gly Asp His Val Ala Met Phe Gly Ser Ala
                 85                  90                  95 aaa gag att ggt tca tgg aaa aag aaa tcg cct ttg aat tgg agt gag    336
Lys Glu Ile Gly Ser Trp Lys Lys Lys Ser Pro Leu Asn Trp Ser Glu
            100                 105                 110 aat gga tgg gtt tgt gag ttg gaa ctt gac ggt ggt cag gtt ttg gag    384
Asn Gly Trp Val Cys Glu Leu Glu Leu Asp Gly Gly Gln Val Leu Glu
        115                 120                 125 tat aag ttt gtc att gtt aag aat gat ggt tca ctt tca tgg gaa tct    432
Tyr Lys Phe Val Ile Val Lys Asn Asp Gly Ser Leu Ser Trp Glu Ser
130                 135                 140 ggt gat aat cgt gtc ctt aag gtt cca aat tct ggg aat ttt tct gtt    480
Gly Asp Asn Arg Val Leu Lys Val Pro Asn Ser Gly Asn Phe Ser Val
145                 150                 155                 160 gtt tgt cat tgg gat gct act aga gaa acc ctt gat ttg cct cag gag    528
Val Cys His Trp Asp Ala Thr Arg Glu Thr Leu Asp Leu Pro Gln Glu
                165                 170                 175 gtt ggt aat gat gat gat gtt ggt gat ggt ggg cat gag agg gat aat    576
Val Gly Asn Asp Asp Asp Val Gly Asp Gly Gly His Glu Arg Asp Asn
            180                 185                 190 cat gat gtt ggt gat gat aga gta gtg gga agt gaa aat ggt gcg cag    624
His Asp Val Gly Asp Asp Arg Val Val Gly Ser Glu Asn Gly Ala Gln
        195                 200                 205 ctt cag aag agt aca ttg ggt ggg caa tgg caa ggt aaa gat gcg tcc    672
Leu Gln Lys Ser Thr Leu Gly Gly Gln Trp Gln Gly Lys Asp Ala Ser
    210                 215                 220 ttt atg cgt tct aat gat cat ggt aac aga gaa gtt ggt aga aat tgg    720
Phe Met Arg Ser Asn Asp His Gly Asn Arg Glu Val Gly Arg Asn Trp
225                 230                 235                 240 gat act agt ggt ctt gaa ggc aca gct ctt aag atg gtt gag ggt gat    768
Asp Thr Ser Gly Leu Glu Gly Thr Ala Leu Lys Met Val Glu Gly Asp
                245                 250                 255 cgc aac tct aag aac tgg tgg aga aag ctt gaa atg gta cgc gag gtt    816
Arg Asn Ser Lys Asn Trp Trp Arg Lys Leu Glu Met Val Arg Glu Val
            260                 265                 270 ata gtt ggg agt gtt gag agg gag gaa cga ttg aag gcg ctc ata tac    864
Ile Val Gly Ser Val Glu Arg Glu Glu Arg Leu Lys Ala Leu Ile Tyr
        275                 280                 285 tct gca att tat ttg aag tgg ata aac aca ggt cag att cct tgt ttt    912
Ser Ala Ile Tyr Leu Lys Trp Ile Asn Thr Gly Gln Ile Pro Cys Phe
    290                 295                 300 gaa gat gga ggg cat cac cgt cca aac agg cat gcc gag att tcc aga    960
Glu Asp Gly Gly His His Arg Pro Asn Arg His Ala Glu Ile Ser Arg
305                 310                 315                 320 ctt ata ttc cgt gag ttg gag cac att tgc agt aag aaa gat gct act   1008
Leu Ile Phe Arg Glu Leu Glu His Ile Cys Ser Lys Lys Asp Ala Thr
                325                 330                 335 cca gag gaa gtg ctt gtt gct cgg aaa atc cat ccg tgt tta cct tct   1056
Pro Glu Glu Val Leu Val Ala Arg Lys Ile His Pro Cys Leu Pro Ser
```

```
                340             345             350
ttc aaa gca gag ttt act gca gct gtc cct cta act cgg att agg gac    1104
Phe Lys Ala Glu Phe Thr Ala Ala Val Pro Leu Thr Arg Ile Arg Asp
        355             360             365 ata gcc cat cgg aat gat att cct cat gat ctc aag caa gaa atc aag    1152
Ile Ala His Arg Asn Asp Ile Pro His Asp Leu Lys Gln Glu Ile Lys
370             375             380 cat acg ata caa aat aag ctt cac cgg aat gct ggt cca gaa gat cta    1200
His Thr Ile Gln Asn Lys Leu His Arg Asn Ala Gly Pro Glu Asp Leu
385             390             395             400 att gca aca gaa gca atg ctt caa cga att acc gag acc cca gga aaa    1248
Ile Ala Thr Glu Ala Met Leu Gln Arg Ile Thr Glu Thr Pro Gly Lys
            405             410             415 tat agt gga gac ttt gtg gag cag ttt aaa ata ttc cat aat gag ctt    1296
Tyr Ser Gly Asp Phe Val Glu Gln Phe Lys Ile Phe His Asn Glu Leu
            420             425             430 aaa gat ttc ttt aat gct gga agt ctc act gaa cag ctt gat tct atg    1344
Lys Asp Phe Phe Asn Ala Gly Ser Leu Thr Glu Gln Leu Asp Ser Met
        435             440             445 aaa att tct atg gat gat aga ggt ctt tct gcg ctc aat ttg ttt ttt    1392
Lys Ile Ser Met Asp Asp Arg Gly Leu Ser Ala Leu Asn Leu Phe Phe
450             455             460 gaa tgt aaa aag cgc ctt gac aca tca gga gaa tca agc aat gtt ttg    1440
Glu Cys Lys Lys Arg Leu Asp Thr Ser Gly Glu Ser Ser Asn Val Leu
465             470             475             480 gag ttg att aaa acc atg cat tct cta gct tct tta aga gaa aca att    1488
Glu Leu Ile Lys Thr Met His Ser Leu Ala Ser Leu Arg Glu Thr Ile
            485             490             495 ata aag gaa ctt aat agc ggc ttg cga aat gat gct cct gat act gcc    1536
Ile Lys Glu Leu Asn Ser Gly Leu Arg Asn Asp Ala Pro Asp Thr Ala
            500             505             510 att gca atg cgc cag aag tgg cgc ctt tgt gag atc ggc ctc gag gac    1584
Ile Ala Met Arg Gln Lys Trp Arg Leu Cys Glu Ile Gly Leu Glu Asp
        515             520             525 tac ttt ttt gtt cta cta agc aga ttc ctc aat gct ctt gaa act atg    1632
Tyr Phe Phe Val Leu Leu Ser Arg Phe Leu Asn Ala Leu Glu Thr Met
530             535             540 gga gga gct gat caa ctg gca aaa gat gtg gga tca aga aac gtt gcc    1680
Gly Gly Ala Asp Gln Leu Ala Lys Asp Val Gly Ser Arg Asn Val Ala
545             550             555             560 tca tgg aat gat cca cta gat gct ttg gtg ttg ggt gtt cac caa gta    1728
Ser Trp Asn Asp Pro Leu Asp Ala Leu Val Leu Gly Val His Gln Val
            565             570             575 ggt cta tct ggt tgg aag caa gaa gaa tgt tta gcc att gga aat gaa    1776
Gly Leu Ser Gly Trp Lys Gln Glu Glu Cys Leu Ala Ile Gly Asn Glu
            580             585             590 ctc ctt gct tgg cga gaa agg gac cta ctt gaa aaa gaa ggg gaa gag    1824
Leu Leu Ala Trp Arg Glu Arg Asp Leu Leu Glu Lys Glu Gly Glu Glu
        595             600             605 gat gga aaa aca att tgg gcc atg agg ctg aaa gca act ctt gat cga    1872
Asp Gly Lys Thr Ile Trp Ala Met Arg Leu Lys Ala Thr Leu Asp Arg
610             615             620 gca cgc aga tta aca gca gaa tat tct gat ttg ctt ctt caa ata ttt    1920
Ala Arg Arg Leu Thr Ala Glu Tyr Ser Asp Leu Leu Leu Gln Ile Phe
625             630             635             640 cct cct aat gtg gag att tta gga aaa gct cta gga att cca gag aat    1968
Pro Pro Asn Val Glu Ile Leu Gly Lys Ala Leu Gly Ile Pro Glu Asn
            645             650             655 agt gtc aag acc tat aca gaa gca gag att cgt gct gga att att ttc    2016
Ser Val Lys Thr Tyr Thr Glu Ala Glu Ile Arg Ala Gly Ile Ile Phe
```

|  |  |
|---|---|
| Ser Val Lys Thr Tyr Thr Glu Ala Glu Ile Arg Ala Gly Ile Ile Phe<br>660                      665                  670 |  |
| cag atc tca aag ctc tgc act gtt ctt cta aaa gct gta aga aat tca<br>Gln Ile Ser Lys Leu Cys Thr Val Leu Leu Lys Ala Val Arg Asn Ser<br>          675                  680                  685 | 2064 |
| ctt ggt tct gag ggc tgg gat gtc gtt gta cct gga tcg acg tct ggg<br>Leu Gly Ser Glu Gly Trp Asp Val Val Val Pro Gly Ser Thr Ser Gly<br>690                      695                  700 | 2112 |
| aca tta gtt cag gtt gag agc att gtt ccg gga tca ttg cca gca act<br>Thr Leu Val Gln Val Glu Ser Ile Val Pro Gly Ser Leu Pro Ala Thr<br>705                      710                  715                  720 | 2160 |
| tct ggt ggt cct att att ctc ttg gtc aat aaa gct gat ggc gat gaa<br>Ser Gly Gly Pro Ile Ile Leu Leu Val Asn Lys Ala Asp Gly Asp Glu<br>                  725                  730                  735 | 2208 |
| gag gta agt gct gct aat ggg aac ata gct gga gtc atg ctt ctg cag<br>Glu Val Ser Ala Ala Asn Gly Asn Ile Ala Gly Val Met Leu Leu Gln<br>740                      745                  750 | 2256 |
| gag ctg cct cac ttg tct cac ctt ggc gtt aga gcg cgg cag gag aaa<br>Glu Leu Pro His Leu Ser His Leu Gly Val Arg Ala Arg Gln Glu Lys<br>          755                  760                  765 | 2304 |
| att gtc ttt gtg aca tgt gat gat gat gac aag gtt gct gat ata cga<br>Ile Val Phe Val Thr Cys Asp Asp Asp Asp Lys Val Ala Asp Ile Arg<br>770                      775                  780 | 2352 |
| cga ctt gtg gga aaa ttt gtg agg ttg gaa gca tct cca agt cat gtg<br>Arg Leu Val Gly Lys Phe Val Arg Leu Glu Ala Ser Pro Ser His Val<br>785                      790                  795                  800 | 2400 |
| aat ctg ata ctt tca act gag ggt agg agt cgc act tcc aaa tcc agt<br>Asn Leu Ile Leu Ser Thr Glu Gly Arg Ser Arg Thr Ser Lys Ser Ser<br>          805                  810                  815 | 2448 |
| gcg acc aaa aaa acg gat aag aac agc tta tct aag aaa aaa aca gat<br>Ala Thr Lys Lys Thr Asp Lys Asn Ser Leu Ser Lys Lys Lys Thr Asp<br>820                      825                  830 | 2496 |
| aag aag agc tta tct atc gat gat gaa gaa tca aag cct ggt tcc tca<br>Lys Lys Ser Leu Ser Ile Asp Asp Glu Glu Ser Lys Pro Gly Ser Ser<br>          835                  840                  845 | 2544 |
| tct tcc aat agc ctc ctt tac tct tcc aag gat atc cct agt gga gga<br>Ser Ser Asn Ser Leu Leu Tyr Ser Ser Lys Asp Ile Pro Ser Gly Gly<br>850                      855                  860 | 2592 |
| atc ata gca ctt gct gat gca gat gta cca act tct ggt tca aaa tct<br>Ile Ile Ala Leu Ala Asp Ala Asp Val Pro Thr Ser Gly Ser Lys Ser<br>865                      870                  875                  880 | 2640 |
| gct gca tgt ggt ctt ctt gca tct tta gca gaa gcc tct agt aaa gtg<br>Ala Ala Cys Gly Leu Leu Ala Ser Leu Ala Glu Ala Ser Ser Lys Val<br>                  885                  890                  895 | 2688 |
| cac agc gaa cac gga gtt ccg gca tca ttt aag gtt cca act gga gtt<br>His Ser Glu His Gly Val Pro Ala Ser Phe Lys Val Pro Thr Gly Val<br>900                      905                  910 | 2736 |
| gtc ata cct ttt gga tcg atg gaa tta gct tta aag caa aat aat tcg<br>Val Ile Pro Phe Gly Ser Met Glu Leu Ala Leu Lys Gln Asn Asn Ser<br>          915                  920                  925 | 2784 |
| gaa gaa aag ttt gcg tct ttg cta gaa aaa cta gaa acc gcc aga cct<br>Glu Glu Lys Phe Ala Ser Leu Leu Glu Lys Leu Glu Thr Ala Arg Pro<br>930                      935                  940 | 2832 |
| gag ggt ggt gag cta gac gac ata tgt gac cag atc cat gaa gtg atg<br>Glu Gly Gly Glu Leu Asp Asp Ile Cys Asp Gln Ile His Glu Val Met<br>945                      950                  955                  960 | 2880 |
| aaa acg ttg caa gtg cct aaa gaa aca atc aac agc ata agc aaa gcg<br>Lys Thr Leu Gln Val Pro Lys Glu Thr Ile Asn Ser Ile Ser Lys Ala<br>          965                  970                  975 | 2928 |

| | | |
|---|---|---|
| ttt ctc aaa gat gct cgt ctc att gtt cgt tca agt gct aac gtc gag<br>Phe Leu Lys Asp Ala Arg Leu Ile Val Arg Ser Ser Ala Asn Val Glu<br>          980                   985                  990 | 2976 |
| gac tta gcc gga atg tca gct gca gga ctc tat gaa tca atc cct aac<br>Asp Leu Ala Gly Met Ser Ala Ala Gly Leu Tyr Glu Ser Ile Pro Asn<br>          995                   1000                1005 | 3024 |
| gtg agt ccc tcg gat cct ttg gtg ttt tca gat tcg gtt tgc caa<br>Val Ser Pro Ser Asp Pro Leu Val Phe Ser Asp Ser Val Cys Gln<br>  1010                   1015                 1020 | 3069 |
| gtt tgg gct tct ctc tac aca aga aga gct gtt cta agc cgt aga<br>Val Trp Ala Ser Leu Tyr Thr Arg Arg Ala Val Leu Ser Arg Arg<br>  1025                   1030                 1035 | 3114 |
| gct gct ggt gtc tct caa aga gaa gct tca atg gct gtt ctc gtt<br>Ala Ala Gly Val Ser Gln Arg Glu Ala Ser Met Ala Val Leu Val<br>  1040                   1045                 1050 | 3159 |
| caa gaa atg ctt tcg ccg gac tta tca ttc gtt ctg cac aca gtg<br>Gln Glu Met Leu Ser Pro Asp Leu Ser Phe Val Leu His Thr Val<br>  1055                   1060                 1065 | 3204 |
| agt cca gct gat ccg gac agt aac ctt gtg gaa gcc gag atc gct<br>Ser Pro Ala Asp Pro Asp Ser Asn Leu Val Glu Ala Glu Ile Ala<br>  1070                   1075                 1080 | 3249 |
| cct ggt tta ggt gag act tta gct tca gga aca aga gga aca cca<br>Pro Gly Leu Gly Glu Thr Leu Ala Ser Gly Thr Arg Gly Thr Pro<br>  1085                   1090                 1095 | 3294 |
| tgg aga ctc gct tcg ggt aag ctc gac ggg att gta caa acc tta<br>Trp Arg Leu Ala Ser Gly Lys Leu Asp Gly Ile Val Gln Thr Leu<br>  1100                   1105                 1110 | 3339 |
| gct ttc gca aac ttc agc gaa gag ctt ctt gtg tca gga aca ggt<br>Ala Phe Ala Asn Phe Ser Glu Glu Leu Leu Val Ser Gly Thr Gly<br>  1115                   1120                 1125 | 3384 |
| cct gct gat gga aaa tac gtt cgg ttg acc gtg gac tat agc aaa<br>Pro Ala Asp Gly Lys Tyr Val Arg Leu Thr Val Asp Tyr Ser Lys<br>  1130                   1135                 1140 | 3429 |
| aaa cgt tta act gtt gac tcg gtg ttt aga cag cag ctc ggt cag<br>Lys Arg Leu Thr Val Asp Ser Val Phe Arg Gln Gln Leu Gly Gln<br>  1145                   1150                 1155 | 3474 |
| aga ctc ggt tcg gtt ggt ttc ttc ttg gaa aga aac ttt ggc tgt<br>Arg Leu Gly Ser Val Gly Phe Phe Leu Glu Arg Asn Phe Gly Cys<br>  1160                   1165                 1170 | 3519 |
| gct caa gac gtt gaa ggt tgt ttg gtt ggt gaa gat gtt tac att<br>Ala Gln Asp Val Glu Gly Cys Leu Val Gly Glu Asp Val Tyr Ile<br>  1175                   1180                 1185 | 3564 |
| gtt cag tca agg cca caa cct ctg tag<br>Val Gln Ser Arg Pro Gln Pro Leu<br>  1190                   1195 | 3591 |

```
<210> SEQ ID NO 2
<211> LENGTH: 1196
<212> TYPE: PRT
<213> ORGANISM: Arabidopsis thaliana

<400> SEQUENCE: 2

Met Glu Ser Ile Gly Ser His Cys Cys Ser Ser Pro Phe Thr Phe Ile
1               5                   10                  15

Thr Arg Asn Ser Ser Ser Ser Leu Pro Arg Leu Val Asn Ile Thr His
            20                  25                  30

Arg Val Asn Leu Ser His Gln Ser His Arg Leu Arg Asn Ser Asn Ser
        35                  40                  45

Arg Leu Thr Cys Thr Ala Thr Ser Ser Ser Thr Ile Glu Glu Gln Arg
    50                  55                  60
```

```
Lys Lys Lys Asp Gly Ser Gly Thr Lys Val Arg Leu Asn Val Arg Leu
65                  70                  75                  80

Asp His Gln Val Asn Phe Gly Asp His Val Ala Met Phe Gly Ser Ala
                85                  90                  95

Lys Glu Ile Gly Ser Trp Lys Lys Lys Ser Pro Leu Asn Trp Ser Glu
            100                 105                 110

Asn Gly Trp Val Cys Glu Leu Glu Leu Asp Gly Gly Gln Val Leu Glu
            115                 120                 125

Tyr Lys Phe Val Ile Val Lys Asn Asp Gly Ser Leu Ser Trp Glu Ser
        130                 135                 140

Gly Asp Asn Arg Val Leu Lys Val Pro Asn Ser Gly Asn Phe Ser Val
145                 150                 155                 160

Val Cys His Trp Asp Ala Thr Arg Glu Thr Leu Asp Leu Pro Gln Glu
                165                 170                 175

Val Gly Asn Asp Asp Asp Val Gly Asp Gly His Glu Arg Asp Asn
                180                 185                 190

His Asp Val Gly Asp Asp Arg Val Val Gly Ser Glu Asn Gly Ala Gln
            195                 200                 205

Leu Gln Lys Ser Thr Leu Gly Gly Gln Trp Gly Lys Asp Ala Ser
210                 215                 220

Phe Met Arg Ser Asn Asp His Gly Asn Arg Glu Val Gly Arg Asn Trp
225                 230                 235                 240

Asp Thr Ser Gly Leu Glu Gly Thr Ala Leu Lys Met Val Glu Gly Asp
            245                 250                 255

Arg Asn Ser Lys Asn Trp Trp Arg Lys Leu Glu Met Val Arg Glu Val
            260                 265                 270

Ile Val Gly Ser Val Glu Arg Glu Arg Leu Lys Ala Leu Ile Tyr
        275                 280                 285

Ser Ala Ile Tyr Leu Lys Trp Ile Asn Thr Gly Gln Ile Pro Cys Phe
        290                 295                 300

Glu Asp Gly Gly His His Arg Pro Asn Arg His Ala Glu Ile Ser Arg
305                 310                 315                 320

Leu Ile Phe Arg Glu Leu Glu His Ile Cys Ser Lys Lys Asp Ala Thr
                325                 330                 335

Pro Glu Glu Val Leu Val Ala Arg Lys Ile His Pro Cys Leu Pro Ser
            340                 345                 350

Phe Lys Ala Glu Phe Thr Ala Ala Val Pro Leu Thr Arg Ile Arg Asp
        355                 360                 365

Ile Ala His Arg Asn Asp Ile Pro His Asp Leu Lys Gln Glu Ile Lys
        370                 375                 380

His Thr Ile Gln Asn Lys Leu His Arg Asn Ala Gly Pro Glu Asp Leu
385                 390                 395                 400

Ile Ala Thr Glu Ala Met Leu Gln Arg Ile Thr Glu Thr Pro Gly Lys
            405                 410                 415

Tyr Ser Gly Asp Phe Val Glu Gln Phe Lys Ile Phe His Asn Glu Leu
            420                 425                 430

Lys Asp Phe Phe Asn Ala Gly Ser Leu Thr Glu Gln Leu Asp Ser Met
        435                 440                 445

Lys Ile Ser Met Asp Asp Arg Gly Leu Ser Ala Leu Asn Leu Phe Phe
        450                 455                 460

Glu Cys Lys Lys Arg Leu Asp Thr Ser Gly Glu Ser Ser Asn Val Leu
465                 470                 475                 480
```

```
Glu Leu Ile Lys Thr Met His Ser Leu Ala Ser Leu Arg Glu Thr Ile
            485                 490                 495

Ile Lys Glu Leu Asn Ser Gly Leu Arg Asn Asp Ala Pro Asp Thr Ala
        500                 505                 510

Ile Ala Met Arg Gln Lys Trp Arg Leu Cys Glu Ile Gly Leu Glu Asp
        515                 520                 525

Tyr Phe Phe Val Leu Leu Ser Arg Phe Leu Asn Ala Leu Glu Thr Met
        530                 535                 540

Gly Gly Ala Asp Gln Leu Ala Lys Asp Val Gly Ser Arg Asn Val Ala
545                 550                 555                 560

Ser Trp Asn Asp Pro Leu Asp Ala Leu Val Leu Gly Val His Gln Val
                565                 570                 575

Gly Leu Ser Gly Trp Lys Gln Glu Cys Leu Ala Ile Gly Asn Glu
            580                 585                 590

Leu Leu Ala Trp Arg Glu Arg Asp Leu Leu Glu Lys Glu Gly Glu Glu
        595                 600                 605

Asp Gly Lys Thr Ile Trp Ala Met Arg Leu Lys Ala Thr Leu Asp Arg
        610                 615                 620

Ala Arg Arg Leu Thr Ala Glu Tyr Ser Asp Leu Leu Leu Gln Ile Phe
625                 630                 635                 640

Pro Pro Asn Val Glu Ile Leu Gly Lys Ala Leu Gly Ile Pro Glu Asn
                645                 650                 655

Ser Val Lys Thr Tyr Thr Glu Ala Glu Ile Arg Ala Gly Ile Ile Phe
                660                 665                 670

Gln Ile Ser Lys Leu Cys Thr Val Leu Leu Lys Ala Val Arg Asn Ser
            675                 680                 685

Leu Gly Ser Glu Gly Trp Asp Val Val Val Pro Gly Ser Thr Ser Gly
        690                 695                 700

Thr Leu Val Gln Val Glu Ser Ile Val Pro Gly Ser Leu Pro Ala Thr
705                 710                 715                 720

Ser Gly Gly Pro Ile Ile Leu Leu Val Asn Lys Ala Asp Gly Asp Glu
                725                 730                 735

Glu Val Ser Ala Ala Asn Gly Asn Ile Ala Gly Val Met Leu Leu Gln
                740                 745                 750

Glu Leu Pro His Leu Ser His Leu Gly Val Arg Ala Arg Gln Glu Lys
        755                 760                 765

Ile Val Phe Val Thr Cys Asp Asp Asp Lys Val Ala Asp Ile Arg
        770                 775                 780

Arg Leu Val Gly Lys Phe Val Arg Leu Glu Ala Ser Pro Ser His Val
785                 790                 795                 800

Asn Leu Ile Leu Ser Thr Glu Gly Arg Ser Arg Thr Ser Lys Ser Ser
                805                 810                 815

Ala Thr Lys Lys Thr Asp Lys Asn Ser Leu Ser Lys Lys Thr Asp
                820                 825                 830

Lys Lys Ser Leu Ser Ile Asp Asp Glu Ser Lys Pro Gly Ser Ser
        835                 840                 845

Ser Ser Asn Ser Leu Leu Tyr Ser Ser Lys Ile Pro Ser Gly Gly
        850                 855                 860

Ile Ile Ala Leu Ala Asp Ala Asp Val Pro Thr Gly Ser Lys Ser
865                 870                 875                 880

Ala Ala Cys Gly Leu Leu Ala Ser Leu Ala Glu Ala Ser Ser Lys Val
                885                 890                 895

His Ser Glu His Gly Val Pro Ala Ser Phe Lys Val Pro Thr Gly Val
```

```
                900             905             910
Val Ile Pro Phe Gly Ser Met Glu Leu Ala Leu Lys Gln Asn Asn Ser
        915             920             925

Glu Glu Lys Phe Ala Ser Leu Leu Glu Lys Leu Glu Thr Ala Arg Pro
    930             935             940

Glu Gly Gly Glu Leu Asp Asp Ile Cys Asp Gln Ile His Glu Val Met
945             950             955             960

Lys Thr Leu Gln Val Pro Lys Glu Thr Ile Asn Ser Ile Ser Lys Ala
            965             970             975

Phe Leu Lys Asp Ala Arg Leu Ile Val Arg Ser Ser Ala Asn Val Glu
        980             985             990

Asp Leu Ala Gly Met Ser Ala Ala Gly Leu Tyr Glu Ser Ile Pro Asn
    995             1000            1005

Val Ser Pro Ser Asp Pro Leu Val Phe Ser Asp Ser Val Cys Gln
    1010            1015            1020

Val Trp Ala Ser Leu Tyr Thr Arg Arg Ala Val Leu Ser Arg Arg
    1025            1030            1035

Ala Ala Gly Val Ser Gln Arg Glu Ala Ser Met Ala Val Leu Val
    1040            1045            1050

Gln Glu Met Leu Ser Pro Asp Leu Ser Phe Val Leu His Thr Val
    1055            1060            1065

Ser Pro Ala Asp Pro Asp Ser Asn Leu Val Glu Ala Glu Ile Ala
    1070            1075            1080

Pro Gly Leu Gly Glu Thr Leu Ala Ser Gly Thr Arg Gly Thr Pro
    1085            1090            1095

Trp Arg Leu Ala Ser Gly Lys Leu Asp Gly Ile Val Gln Thr Leu
    1100            1105            1110

Ala Phe Ala Asn Phe Ser Glu Leu Leu Val Ser Gly Thr Gly
    1115            1120            1125

Pro Ala Asp Gly Lys Tyr Val Arg Leu Thr Val Asp Tyr Ser Lys
    1130            1135            1140

Lys Arg Leu Thr Val Asp Ser Val Phe Arg Gln Gln Leu Gly Gln
    1145            1150            1155

Arg Leu Gly Ser Val Gly Phe Phe Leu Glu Arg Asn Phe Gly Cys
    1160            1165            1170

Ala Gln Asp Val Glu Gly Cys Leu Val Gly Glu Asp Val Tyr Ile
    1175            1180            1185

Val Gln Ser Arg Pro Gln Pro Leu
    1190            1195

<210> SEQ ID NO 3
<211> LENGTH: 3644
<212> TYPE: DNA
<213> ORGANISM: Oryza sativa
<220> FEATURE:
<221> NAME/KEY: CDS
<222> LOCATION: (13)..(3633)
<223> OTHER INFORMATION:

<400> SEQUENCE: 3
cgaggaggat ca atg acg tcg ctg cgg ccc ctc gaa acc tcg ctc tcc ata      51
              Met Thr Ser Leu Arg Pro Leu Glu Thr Ser Leu Ser Ile
                  1               5                   10 ggc ggc agg ccg cgc cgt ggt ctc gtc ctc ccg ccg ccc gga gtc ggt        99
Gly Gly Arg Pro Arg Arg Gly Leu Val Leu Pro Pro Pro Gly Val Gly
         15                  20                  25
```

-continued

| | | |
|---|---|---|
| gcg ggt gtg ctg ctc cgc cgg gga gcg atg gcg ctc cct ggg cgg cgc<br>Ala Gly Val Leu Leu Arg Arg Gly Ala Met Ala Leu Pro Gly Arg Arg<br>30                           35                      40                     45 | 147 |
| ggc ttc gcg tgc cgc ggg aga tcc gcg gcc tcg gcg gca gag aga aca<br>Gly Phe Ala Cys Arg Gly Arg Ser Ala Ala Ser Ala Ala Glu Arg Thr<br>               50                      55                      60 | 195 |
| aag gag aaa aag aga aga gat tct tca aag cag cca ttg gtg cat ctc<br>Lys Glu Lys Lys Arg Arg Asp Ser Ser Lys Gln Pro Leu Val His Leu<br>          65                      70                      75 | 243 |
| cag gtt tgt cta gag cac cag gtt aag ttt ggt gag cat gta ggc att<br>Gln Val Cys Leu Glu His Gln Val Lys Phe Gly Glu His Val Gly Ile<br>               80                      85                      90 | 291 |
| atc ggt tcc aca aag gag ctt ggt tca tgg gag gag cag gtt gaa ctg<br>Ile Gly Ser Thr Lys Glu Leu Gly Ser Trp Glu Glu Gln Val Glu Leu<br>95                         100                    105 | 339 |
| gaa tgg act aca aat ggt tgg gtc tgc cag ctt aag ctc cct gga gaa<br>Glu Trp Thr Thr Asn Gly Trp Val Cys Gln Leu Lys Leu Pro Gly Glu<br>110                     115                    120                125 | 387 |
| aca ctt gtg gag ttt aaa ttt gtt ata ttt ttg gtg gga gga aaa gat<br>Thr Leu Val Glu Phe Lys Phe Val Ile Phe Leu Val Gly Gly Lys Asp<br>                      130                    135                   140 | 435 |
| aaa ata tgg gaa gat ggt aat aac cgt gtt gtt gag ctg ccg aag gat<br>Lys Ile Trp Glu Asp Gly Asn Asn Arg Val Val Glu Leu Pro Lys Asp<br>145                     150                    155 | 483 |
| ggt aag ttt gat ata gta tgc cac tgg aat aga aca gaa gag cca tta<br>Gly Lys Phe Asp Ile Val Cys His Trp Asn Arg Thr Glu Glu Pro Leu<br>               160                    165                   170 | 531 |
| gaa ctt tta gga aca cca aag ttt gag ttg gtc gga gaa gct gaa aag<br>Glu Leu Leu Gly Thr Pro Lys Phe Glu Leu Val Gly Glu Ala Glu Lys<br>175                     180                    185 | 579 |
| aat act ggc gag gat gct tca gca tct gta act ttt gca cct gaa aaa<br>Asn Thr Gly Glu Asp Ala Ser Ala Ser Val Thr Phe Ala Pro Glu Lys<br>190                     195                    200                205 | 627 |
| gtt caa gat att tca gtt gtt gag aat ggt gat cca gca cca gag gcc<br>Val Gln Asp Ile Ser Val Val Glu Asn Gly Asp Pro Ala Pro Glu Ala<br>                      210                    215                   220 | 675 |
| gag tca agc aaa ttt ggt ggg caa tgg caa gga agt aaa act gtt ttc<br>Glu Ser Ser Lys Phe Gly Gly Gln Trp Gln Gly Ser Lys Thr Val Phe<br>225                     230                    235 | 723 |
| atg aga tca aat gag cat ctg aat aag gag gct gat agg atg tgg gat<br>Met Arg Ser Asn Glu His Leu Asn Lys Glu Ala Asp Arg Met Trp Asp<br>               240                    245                   250 | 771 |
| aca act ggg ctt gat gga ata gca ctg aaa ctg gtg gag ggc gat aaa<br>Thr Thr Gly Leu Asp Gly Ile Ala Leu Lys Leu Val Glu Gly Asp Lys<br>255                     260                    265 | 819 |
| gca tcc agg aac tgg tgg cgg aag tta gag gtt gtt cgc ggg ata ttg<br>Ala Ser Arg Asn Trp Trp Arg Lys Leu Glu Val Val Arg Gly Ile Leu<br>270                     275                    280                285 | 867 |
| tca gaa tct ttt gat gac cag agt cgt ctg ggg gcc ctt gta tac tca<br>Ser Glu Ser Phe Asp Asp Gln Ser Arg Leu Gly Ala Leu Val Tyr Ser<br>                      290                    295                   300 | 915 |
| gct att tat ctg aag tgg att tat aca ggt cag ata tcg tgc ttt gaa<br>Ala Ile Tyr Leu Lys Trp Ile Tyr Thr Gly Gln Ile Ser Cys Phe Glu<br>305                     310                    315 | 963 |
| gat ggt ggc cac cat cgg cct aac aaa cat gct gag ata tcg agg caa<br>Asp Gly Gly His His Arg Pro Asn Lys His Ala Glu Ile Ser Arg Gln<br>               320                    325                   330 | 1011 |
| ata ttc cgt gaa ctt gaa atg atg tat tat ggg aaa acc aca tca gcc<br>Ile Phe Arg Glu Leu Glu Met Met Tyr Tyr Gly Lys Thr Thr Ser Ala<br>335                     340                    345 | 1059 |

```
aag gat gtt ctc gtg att cgc aaa att cat ccc ttt tta cct tca ttt    1107
Lys Asp Val Leu Val Ile Arg Lys Ile His Pro Phe Leu Pro Ser Phe
350                 355                 360                 365 aag tca gag ttt aca gcc tct gtc cct cta aca cga att cgt gat att    1155
Lys Ser Glu Phe Thr Ala Ser Val Pro Leu Thr Arg Ile Arg Asp Ile
                370                 375                 380 gct cac cgg aat gac atc cca cat gat ctc aag caa gaa atc aag cat    1203
Ala His Arg Asn Asp Ile Pro His Asp Leu Lys Gln Glu Ile Lys His
            385                 390                 395 act ata caa aac aaa ctt cat cgt aat gct gga cct gag gat ctt att    1251
Thr Ile Gln Asn Lys Leu His Arg Asn Ala Gly Pro Glu Asp Leu Ile
        400                 405                 410 gct aca gaa gtc atg ctt gct agg att act aag acc cct gga gaa tac    1299
Ala Thr Glu Val Met Leu Ala Arg Ile Thr Lys Thr Pro Gly Glu Tyr
    415                 420                 425 agt gaa aca ttt gtt gaa caa ttc acg ata ttt tat agc gaa cta aaa    1347
Ser Glu Thr Phe Val Glu Gln Phe Thr Ile Phe Tyr Ser Glu Leu Lys
430                 435                 440                 445 gat ttc ttc aat gct ggc agc cta ttt gag caa ctg gag tcc atc aag    1395
Asp Phe Phe Asn Ala Gly Ser Leu Phe Glu Gln Leu Glu Ser Ile Lys
                450                 455                 460 gaa tct ctg aac gag tca ggc tta gaa gtt ctc tca tcc ttt gtg gaa    1443
Glu Ser Leu Asn Glu Ser Gly Leu Glu Val Leu Ser Ser Phe Val Glu
            465                 470                 475 acc aaa agg agt ttg gac caa gtg gat cat gca gaa gat ttg gat aaa    1491
Thr Lys Arg Ser Leu Asp Gln Val Asp His Ala Glu Asp Leu Asp Lys
        480                 485                 490 aat gat acc att caa att ttg atg act acc ttg caa tca tta tct tct    1539
Asn Asp Thr Ile Gln Ile Leu Met Thr Thr Leu Gln Ser Leu Ser Ser
    495                 500                 505 cta aga tcg gtt cta atg aag ggc ctt gaa agt ggc ctt aga aat gat    1587
Leu Arg Ser Val Leu Met Lys Gly Leu Glu Ser Gly Leu Arg Asn Asp
510                 515                 520                 525 gcg cct gat aat gct ata gca atg cga caa aag tgg cgc ctt tgt gaa    1635
Ala Pro Asp Asn Ala Ile Ala Met Arg Gln Lys Trp Arg Leu Cys Glu
                530                 535                 540 att agt ctt gag gat tat tca ttt gtt ctg tta agc aga ttc atc aat    1683
Ile Ser Leu Glu Asp Tyr Ser Phe Val Leu Leu Ser Arg Phe Ile Asn
            545                 550                 555 act ctt gaa gcc tta ggt gga tca gct tca ctt gca aag gat gta gct    1731
Thr Leu Glu Ala Leu Gly Gly Ser Ala Ser Leu Ala Lys Asp Val Ala
        560                 565                 570 aga aat act act cta tgg gat act act ctt gat gcc ctt gtc att ggc    1779
Arg Asn Thr Thr Leu Trp Asp Thr Thr Leu Asp Ala Leu Val Ile Gly
    575                 580                 585 atc aat caa gtt agc ttt tca ggt tgg aaa aca gat gaa tgt att gcc    1827
Ile Asn Gln Val Ser Phe Ser Gly Trp Lys Thr Asp Glu Cys Ile Ala
590                 595                 600                 605 ata ggg aat gag att ctt tcc tgg aag caa aaa ggt cta tct gaa agt    1875
Ile Gly Asn Glu Ile Leu Ser Trp Lys Gln Lys Gly Leu Ser Glu Ser
                610                 615                 620 gaa ggt tgt gaa gat ggg aaa tat att tgg tca cta aga ctt aaa gct    1923
Glu Gly Cys Glu Asp Gly Lys Tyr Ile Trp Ser Leu Arg Leu Lys Ala
            625                 630                 635 aca ctg gac aga gca cgg aga tta acg gaa gag tac tct gaa gca ctt    1971
Thr Leu Asp Arg Ala Arg Arg Leu Thr Glu Glu Tyr Ser Glu Ala Leu
        640                 645                 650 ctt tct ata ttc cct gaa aaa gta atg gtt att ggg aaa gcc ctt gga    2019
Leu Ser Ile Phe Pro Glu Lys Val Met Val Ile Gly Lys Ala Leu Gly
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 655 |     |     |     |     | 660 |     |     |     |     | 665 |     |      |
| ata | cca | gat | aac | agt | gtg | aga | act | tac | aca | gag | gca | gaa | att | cgt | gct | 2067 |
| Ile | Pro | Asp | Asn | Ser | Val | Arg | Thr | Tyr | Thr | Glu | Ala | Glu | Ile | Arg | Ala |      |
| 670 |     |     |     | 675 |     |     |     |     | 680 |     |     |     |     | 685 |     |      |
| ggc | att | gtt | ttt | cag | gta | tct | aaa | cta | tgc | aca | gta | ctt | cag | aaa | gca | 2115 |
| Gly | Ile | Val | Phe | Gln | Val | Ser | Lys | Leu | Cys | Thr | Val | Leu | Gln | Lys | Ala |      |
|     |     | 690 |     |     |     |     | 695 |     |     |     |     | 700 |     |     |     |      |
| att | cga | gaa | gta | ctt | gga | tca | act | ggc | tgg | gat | gtt | ctt | gtt | cct | gga | 2163 |
| Ile | Arg | Glu | Val | Leu | Gly | Ser | Thr | Gly | Trp | Asp | Val | Leu | Val | Pro | Gly |      |
|     |     | 705 |     |     |     |     | 710 |     |     |     |     | 715 |     |     |     |      |
| gtg | gcc | cat | gga | act | ctg | atg | cgg | gtg | gaa | aga | att | ctt | cct | gga | tca | 2211 |
| Val | Ala | His | Gly | Thr | Leu | Met | Arg | Val | Glu | Arg | Ile | Leu | Pro | Gly | Ser |      |
|     |     | 720 |     |     |     |     | 725 |     |     |     |     | 730 |     |     |     |      |
| tta | cct | tca | tct | gtc | aaa | gaa | cct | gtg | gtt | cta | att | gta | gat | aag | gct | 2259 |
| Leu | Pro | Ser | Ser | Val | Lys | Glu | Pro | Val | Val | Leu | Ile | Val | Asp | Lys | Ala |      |
| 735 |     |     |     | 740 |     |     |     |     | 745 |     |     |     |     |     |     |      |
| gat | gga | gat | gaa | gag | gtc | aaa | gct | gct | ggg | gat | aat | ata | gtt | ggt | gtt | 2307 |
| Asp | Gly | Asp | Glu | Glu | Val | Lys | Ala | Ala | Gly | Asp | Asn | Ile | Val | Gly | Val |      |
| 750 |     |     |     | 755 |     |     |     |     | 760 |     |     |     |     | 765 |     |      |
| att | ctt | ctt | cag | gaa | cta | cct | cac | ctt | tca | cat | ctt | ggt | gtt | aga | gct | 2355 |
| Ile | Leu | Leu | Gln | Glu | Leu | Pro | His | Leu | Ser | His | Leu | Gly | Val | Arg | Ala |      |
|     |     |     |     | 770 |     |     |     |     | 775 |     |     |     |     | 780 |     |      |
| cgt | caa | gag | aat | gtt | gta | ttt | gta | act | tgt | gaa | tat | gat | gac | aca | gtt | 2403 |
| Arg | Gln | Glu | Asn | Val | Val | Phe | Val | Thr | Cys | Glu | Tyr | Asp | Asp | Thr | Val |      |
|     |     |     | 785 |     |     |     |     | 790 |     |     |     |     | 795 |     |     |      |
| aca | gat | gtg | tat | ttg | ctt | gag | gga | aaa | tat | atc | aga | tta | gaa | gca | tca | 2451 |
| Thr | Asp | Val | Tyr | Leu | Leu | Glu | Gly | Lys | Tyr | Ile | Arg | Leu | Glu | Ala | Ser |      |
|     |     | 800 |     |     |     |     | 805 |     |     |     |     | 810 |     |     |     |      |
| tcc | atc | aat | gtc | aat | ctc | tca | ata | gtt | tca | gaa | aaa | aat | gac | aat | gct | 2499 |
| Ser | Ile | Asn | Val | Asn | Leu | Ser | Ile | Val | Ser | Glu | Lys | Asn | Asp | Asn | Ala |      |
|     | 815 |     |     |     |     | 820 |     |     |     |     | 825 |     |     |     |     |      |
| gtc | tct | aca | gaa | cca | aat | agt | aca | ggg | aat | cca | ttt | caa | cag | aaa | ctc | 2547 |
| Val | Ser | Thr | Glu | Pro | Asn | Ser | Thr | Gly | Asn | Pro | Phe | Gln | Gln | Lys | Leu |      |
| 830 |     |     |     |     | 835 |     |     |     |     | 840 |     |     |     |     | 845 |      |
| caa | aat | gaa | ttc | tct | cta | cca | tcg | gat | atc | gag | atg | cca | ctg | caa | atg | 2595 |
| Gln | Asn | Glu | Phe | Ser | Leu | Pro | Ser | Asp | Ile | Glu | Met | Pro | Leu | Gln | Met |      |
|     |     |     |     | 850 |     |     |     |     | 855 |     |     |     |     | 860 |     |      |
| tct | aag | caa | aaa | agc | aaa | tca | gga | gtg | aat | ggt | agt | ttt | gct | gct | ctt | 2643 |
| Ser | Lys | Gln | Lys | Ser | Lys | Ser | Gly | Val | Asn | Gly | Ser | Phe | Ala | Ala | Leu |      |
|     | 865 |     |     |     |     | 870 |     |     |     |     | 875 |     |     |     |     |      |
| gag | ctt | tca | gaa | gct | tca | gtg | gaa | tca | gct | ggt | gca | aaa | gct | gct | gca | 2691 |
| Glu | Leu | Ser | Glu | Ala | Ser | Val | Glu | Ser | Ala | Gly | Ala | Lys | Ala | Ala | Ala |      |
|     |     | 880 |     |     |     |     | 885 |     |     |     |     | 890 |     |     |     |      |
| tgc | aga | act | ctt | tct | gtt | ctt | gct | tca | ttg | tct | aat | aaa | gtc | tat | agt | 2739 |
| Cys | Arg | Thr | Leu | Ser | Val | Leu | Ala | Ser | Leu | Ser | Asn | Lys | Val | Tyr | Ser |      |
| 895 |     |     |     |     | 900 |     |     |     |     | 905 |     |     |     |     |     |      |
| gat | caa | gga | gtt | cca | gca | gcc | ttt | aga | gtc | cct | tct | ggt | gct | gtg | ata | 2787 |
| Asp | Gln | Gly | Val | Pro | Ala | Ala | Phe | Arg | Val | Pro | Ser | Gly | Ala | Val | Ile |      |
| 910 |     |     |     | 915 |     |     |     |     | 920 |     |     |     |     | 925 |     |      |
| cca | ttt | gga | tca | atg | gag | gat | gcg | ctc | aag | aaa | agt | gga | tca | ctg | gaa | 2835 |
| Pro | Phe | Gly | Ser | Met | Glu | Asp | Ala | Leu | Lys | Lys | Ser | Gly | Ser | Leu | Glu |      |
|     |     |     |     | 930 |     |     |     |     | 935 |     |     |     |     | 940 |     |      |
| tcc | ttt | aca | agc | ctt | cta | gaa | aag | att | gaa | aca | gcc | aaa | gtc | gaa | aat | 2883 |
| Ser | Phe | Thr | Ser | Leu | Leu | Glu | Lys | Ile | Glu | Thr | Ala | Lys | Val | Glu | Asn |      |
|     | 945 |     |     |     |     | 950 |     |     |     |     | 955 |     |     |     |     |      |
| ggt | gaa | gtt | gat | agc | ctg | gcg | ttg | gag | cta | caa | gca | ata | att | tca | cat | 2931 |
| Gly | Glu | Val | Asp | Ser | Leu | Ala | Leu | Glu | Leu | Gln | Ala | Ile | Ile | Ser | His |      |
|     |     | 960 |     |     |     |     | 965 |     |     |     |     | 970 |     |     |     |      |
| ctt | tcc | cca | ccg | gag | gag | act | att | ata | ttt | ctc | aaa | aga | atc | ttc | cca | 2979 |

```
                                                                              -continued
Leu Ser Pro Pro Glu Glu Thr Ile Ile Phe Leu Lys Arg Ile Phe Pro
        975                 980                 985 cag gat gtc cgg ttg att gtt aga tct agt gct  aat gtg gag gat ttg             3027
Gln Asp Val Arg Leu Ile Val Arg Ser Ser Ala  Asn Val Glu Asp Leu
990                 995                 1000                 1005 gct ggt atg tca gct gct ggt ctc tat gat tca att ccc aat gtc                  3072
Ala Gly Met Ser Ala Ala Gly Leu Tyr Asp Ser Ile Pro Asn Val
                1010                 1015                 1020 agt ctc atg gac cca tgt gcc ttt gga gct gcg gtt ggg aag gtt                  3117
Ser Leu Met Asp Pro Cys Ala Phe Gly Ala Ala Val Gly Lys Val
                1025                 1030                 1035 tgg gct tct tta tac aca agg aga gcc atc cta agc cgt cga gcc                  3162
Trp Ala Ser Leu Tyr Thr Arg Arg Ala Ile Leu Ser Arg Arg Ala
                1040                 1045                 1050 gct ggt gtt tat cag aga gac gcg aca atg gct gtt ctt gtc caa                  3207
Ala Gly Val Tyr Gln Arg Asp Ala Thr Met Ala Val Leu Val Gln
                1055                 1060                 1065 gaa ata ctg cag cca gat ctc tcc ttc gtg ctt cat act gtt tgc                  3252
Glu Ile Leu Gln Pro Asp Leu Ser Phe Val Leu His Thr Val Cys
                1070                 1075                 1080 ccc gct gac cat gac ccc aag gtt gtc cag gct gag gtc gcc cct                  3297
Pro Ala Asp His Asp Pro Lys Val Val Gln Ala Glu Val Ala Pro
                1085                 1090                 1095 ggg ctg ggt gaa acg ctt gct tca gga acc cgt ggc acc ccg tgg                  3342
Gly Leu Gly Glu Thr Leu Ala Ser Gly Thr Arg Gly Thr Pro Trp
                1100                 1105                 1110 agg ctg tca tgt aac aaa ttc gat gga aaa gtt gcc act ctt gcc                  3387
Arg Leu Ser Cys Asn Lys Phe Asp Gly Lys Val Ala Thr Leu Ala
                1115                 1120                 1125 ttt tca aat ttc agt gag gag atg gtg gtg cac aac tct ggt cct                  3432
Phe Ser Asn Phe Ser Glu Glu Met Val Val His Asn Ser Gly Pro
                1130                 1135                 1140 gcc aat gga gaa gta att cgt ctt act gtt gat tac agc aag aag                  3477
Ala Asn Gly Glu Val Ile Arg Leu Thr Val Asp Tyr Ser Lys Lys
                1145                 1150                 1155 cca ttg tcg gtt gat aca acc ttt agg aag cag ttt ggt cag cga                  3522
Pro Leu Ser Val Asp Thr Thr Phe Arg Lys Gln Phe Gly Gln Arg
                1160                 1165                 1170 ctg gct gcg att ggc cag tat ctg gag cag aag ttc ggg agt gca                  3567
Leu Ala Ala Ile Gly Gln Tyr Leu Glu Gln Lys Phe Gly Ser Ala
                1175                 1180                 1185 cag gat gtg gaa ggt tgc ctg gtt ggg aaa gat att ttt ata gtg                  3612
Gln Asp Val Glu Gly Cys Leu Val Gly Lys Asp Ile Phe Ile Val
                1190                 1195                 1200 caa agc agg cca cag cca tag aagccgaatt c                                     3644
Gln Ser Arg Pro Gln Pro
                1205

<210> SEQ ID NO 4
<211> LENGTH: 1206
<212> TYPE: PRT
<213> ORGANISM: Oryza sativa

<400> SEQUENCE: 4

Met Thr Ser Leu Arg Pro Leu Glu Thr Ser Leu Ser Ile Gly Gly Arg
1               5                   10                  15

Pro Arg Arg Gly Leu Val Leu Pro Pro Gly Val Gly Ala Gly Val
            20                  25                  30

Leu Leu Arg Arg Gly Ala Met Ala Leu Pro Gly Arg Arg Gly Phe Ala
        35                  40                  45
```

```
Cys Arg Gly Arg Ser Ala Ala Ser Ala Ala Glu Arg Thr Lys Glu Lys
 50                  55                  60

Lys Arg Arg Asp Ser Ser Lys Gln Pro Leu Val His Leu Gln Val Cys
 65                  70                  75                  80

Leu Glu His Gln Val Lys Phe Gly Glu His Val Gly Ile Ile Gly Ser
                 85                  90                  95

Thr Lys Glu Leu Gly Ser Trp Glu Gln Val Glu Leu Glu Trp Thr
                100                 105                 110

Thr Asn Gly Trp Val Cys Gln Leu Lys Leu Pro Gly Glu Thr Leu Val
                115                 120                 125

Glu Phe Lys Phe Val Ile Phe Leu Val Gly Gly Lys Asp Lys Ile Trp
            130                 135                 140

Glu Asp Gly Asn Asn Arg Val Val Glu Leu Pro Lys Asp Gly Lys Phe
145                 150                 155                 160

Asp Ile Val Cys His Trp Asn Arg Thr Glu Glu Pro Leu Glu Leu Leu
                165                 170                 175

Gly Thr Pro Lys Phe Glu Leu Val Gly Glu Ala Glu Lys Asn Thr Gly
                180                 185                 190

Glu Asp Ala Ser Ala Ser Val Thr Phe Ala Pro Glu Lys Val Gln Asp
                195                 200                 205

Ile Ser Val Val Glu Asn Gly Asp Pro Ala Pro Glu Ala Glu Ser Ser
            210                 215                 220

Lys Phe Gly Gly Gln Trp Gln Gly Ser Lys Thr Val Phe Met Arg Ser
225                 230                 235                 240

Asn Glu His Leu Asn Lys Glu Ala Asp Arg Met Trp Asp Thr Thr Gly
                245                 250                 255

Leu Asp Gly Ile Ala Leu Lys Leu Val Glu Gly Asp Lys Ala Ser Arg
                260                 265                 270

Asn Trp Trp Arg Lys Leu Glu Val Val Arg Gly Ile Leu Ser Glu Ser
            275                 280                 285

Phe Asp Asp Gln Ser Arg Leu Gly Ala Leu Val Tyr Ser Ala Ile Tyr
            290                 295                 300

Leu Lys Trp Ile Tyr Thr Gly Gln Ile Ser Cys Phe Glu Asp Gly Gly
305                 310                 315                 320

His His Arg Pro Asn Lys His Ala Glu Ile Ser Arg Gln Ile Phe Arg
                325                 330                 335

Glu Leu Glu Met Met Tyr Tyr Gly Lys Thr Thr Ser Ala Lys Asp Val
                340                 345                 350

Leu Val Ile Arg Lys Ile His Pro Phe Leu Pro Ser Phe Lys Ser Glu
            355                 360                 365

Phe Thr Ala Ser Val Pro Leu Thr Arg Ile Arg Asp Ile Ala His Arg
            370                 375                 380

Asn Asp Ile Pro His Asp Leu Lys Gln Glu Ile Lys His Thr Ile Gln
385                 390                 395                 400

Asn Lys Leu His Arg Asn Ala Gly Pro Glu Asp Leu Ile Ala Thr Glu
                405                 410                 415

Val Met Leu Ala Arg Ile Thr Lys Thr Pro Gly Glu Tyr Ser Glu Thr
                420                 425                 430

Phe Val Glu Gln Phe Thr Ile Phe Tyr Ser Glu Leu Lys Asp Phe Phe
            435                 440                 445

Asn Ala Gly Ser Leu Phe Glu Gln Leu Glu Ser Ile Lys Glu Ser Leu
450                 455                 460
```

-continued

```
Asn Glu Ser Gly Leu Glu Val Leu Ser Ser Phe Val Glu Thr Lys Arg
465                 470                 475                 480

Ser Leu Asp Gln Val Asp His Ala Glu Asp Leu Asp Lys Asn Asp Thr
            485                 490                 495

Ile Gln Ile Leu Met Thr Thr Leu Gln Ser Leu Ser Ser Leu Arg Ser
        500                 505                 510

Val Leu Met Lys Gly Leu Glu Ser Gly Leu Arg Asn Asp Ala Pro Asp
    515                 520                 525

Asn Ala Ile Ala Met Arg Gln Lys Trp Arg Leu Cys Glu Ile Ser Leu
530                 535                 540

Glu Asp Tyr Ser Phe Val Leu Leu Ser Arg Phe Ile Asn Thr Leu Glu
545                 550                 555                 560

Ala Leu Gly Gly Ser Ala Ser Leu Ala Lys Asp Val Ala Arg Asn Thr
            565                 570                 575

Thr Leu Trp Asp Thr Thr Leu Asp Ala Leu Val Ile Gly Ile Asn Gln
        580                 585                 590

Val Ser Phe Ser Gly Trp Lys Thr Asp Glu Cys Ile Ala Ile Gly Asn
    595                 600                 605

Glu Ile Leu Ser Trp Lys Gln Lys Gly Leu Ser Glu Ser Glu Gly Cys
610                 615                 620

Glu Asp Gly Lys Tyr Ile Trp Ser Leu Arg Leu Lys Ala Thr Leu Asp
625                 630                 635                 640

Arg Ala Arg Arg Leu Thr Glu Glu Tyr Ser Glu Ala Leu Leu Ser Ile
            645                 650                 655

Phe Pro Glu Lys Val Met Val Ile Gly Lys Ala Leu Gly Ile Pro Asp
        660                 665                 670

Asn Ser Val Arg Thr Tyr Thr Glu Ala Glu Ile Arg Ala Gly Ile Val
    675                 680                 685

Phe Gln Val Ser Lys Leu Cys Thr Val Leu Gln Lys Ala Ile Arg Glu
690                 695                 700

Val Leu Gly Ser Thr Gly Trp Asp Val Leu Val Pro Gly Val Ala His
705                 710                 715                 720

Gly Thr Leu Met Arg Val Glu Arg Ile Leu Pro Gly Ser Leu Pro Ser
            725                 730                 735

Ser Val Lys Glu Pro Val Val Leu Ile Val Asp Lys Ala Asp Gly Asp
        740                 745                 750

Glu Glu Val Lys Ala Ala Gly Asp Asn Ile Val Gly Val Ile Leu Leu
    755                 760                 765

Gln Glu Leu Pro His Leu Ser His Leu Gly Val Arg Ala Arg Gln Glu
770                 775                 780

Asn Val Val Phe Val Thr Cys Glu Tyr Asp Asp Thr Val Thr Asp Val
785                 790                 795                 800

Tyr Leu Leu Glu Gly Lys Tyr Ile Arg Leu Glu Ala Ser Ser Ile Asn
            805                 810                 815

Val Asn Leu Ser Ile Val Ser Glu Lys Asn Asp Asn Ala Val Ser Thr
        820                 825                 830

Glu Pro Asn Ser Thr Gly Asn Pro Phe Gln Gln Lys Leu Gln Asn Glu
    835                 840                 845

Phe Ser Leu Pro Ser Asp Ile Glu Met Pro Leu Gln Met Ser Lys Gln
850                 855                 860

Lys Ser Lys Ser Gly Val Asn Gly Ser Phe Ala Ala Leu Glu Leu Ser
865                 870                 875                 880

Glu Ala Ser Val Glu Ser Ala Gly Ala Lys Ala Ala Ala Cys Arg Thr
```

```
                  885                 890                 895

Leu Ser Val Leu Ala Ser Leu Ser Asn Lys Val Tyr Ser Asp Gln Gly
            900                 905                 910

Val Pro Ala Ala Phe Arg Val Pro Ser Gly Ala Val Ile Pro Phe Gly
            915                 920                 925

Ser Met Glu Asp Ala Leu Lys Lys Ser Gly Ser Leu Glu Ser Phe Thr
       930                 935                 940

Ser Leu Leu Glu Lys Ile Glu Thr Ala Lys Val Glu Asn Gly Glu Val
945                 950                 955                 960

Asp Ser Leu Ala Leu Glu Leu Gln Ala Ile Ile Ser His Leu Ser Pro
                965                 970                 975

Pro Glu Glu Thr Ile Ile Phe Leu Lys Arg Ile Phe Pro Gln Asp Val
            980                 985                 990

Arg Leu Ile Val Arg Ser Ser Ala Asn Val Glu Asp Leu Ala Gly Met
            995                1000                1005

Ser Ala Ala Gly Leu Tyr Asp Ser Ile Pro Asn Val Ser Leu Met
       1010                1015                1020

Asp Pro Cys Ala Phe Gly Ala Ala Val Gly Lys Val Trp Ala Ser
       1025                1030                1035

Leu Tyr Thr Arg Arg Ala Ile Leu Ser Arg Arg Ala Ala Gly Val
       1040                1045                1050

Tyr Gln Arg Asp Ala Thr Met Ala Val Leu Val Gln Glu Ile Leu
       1055                1060                1065

Gln Pro Asp Leu Ser Phe Val Leu His Thr Val Cys Pro Ala Asp
       1070                1075                1080

His Asp Pro Lys Val Val Gln Ala Glu Val Ala Pro Gly Leu Gly
       1085                1090                1095

Glu Thr Leu Ala Ser Gly Thr Arg Gly Thr Pro Trp Arg Leu Ser
       1100                1105                1110

Cys Asn Lys Phe Asp Gly Lys Val Ala Thr Leu Ala Phe Ser Asn
       1115                1120                1125

Phe Ser Glu Glu Met Val Val His Asn Ser Gly Pro Ala Asn Gly
       1130                1135                1140

Glu Val Ile Arg Leu Thr Val Asp Tyr Ser Lys Lys Pro Leu Ser
       1145                1150                1155

Val Asp Thr Thr Phe Arg Lys Gln Phe Gly Gln Arg Leu Ala Ala
       1160                1165                1170

Ile Gly Gln Tyr Leu Glu Gln Lys Phe Gly Ser Ala Gln Asp Val
       1175                1180                1185

Glu Gly Cys Leu Val Gly Lys Asp Ile Phe Ile Val Gln Ser Arg
       1190                1195                1200

Pro Gln Pro
       1205

<210> SEQ ID NO 5
<211> LENGTH: 12
<212> TYPE: PRT
<213> ORGANISM: Arabidopsis thaliana, Oryza sativa

<400> SEQUENCE: 5

Leu Pro His Leu Ser His Leu Gly Val Arg Ala Arg
1               5                   10

<210> SEQ ID NO 6
<211> LENGTH: 27
```

```
<212> TYPE: DNA
<213> ORGANISM: Artificial Sequence
<220> FEATURE:
<223> OTHER INFORMATION: Chemically Synthesized

<400> SEQUENCE: 6
gactcaacca cataacacac aaagatc                                       27

<210> SEQ ID NO 7
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 7
tggtaacgag gcaaatgcag a                                             21

<210> SEQ ID NO 8
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 8
atctcttatc acaccacctc caatg                                         25

<210> SEQ ID NO 9
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 9
ggaaccgata atgcctacat gctc                                          24

<210> SEQ ID NO 10
<211> LENGTH: 39
<212> TYPE: DNA
<213> ORGANISM: Artificial Sequence
<220> FEATURE:
<223> OTHER INFORMATION: Chemically Synthesized

<400> SEQUENCE: 10
aaaactcgag gaggatcaat gacgtcgctg cggcccctc                          39

<210> SEQ ID NO 11
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 11
ccaggttaag tttggtgagc a                                             21

<210> SEQ ID NO 12
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 12
```
caaagcacga tatctgacct gt                                              22

<210> SEQ ID NO 13
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 13
ttgttcgcgg gatattgtca ga                                              22

<210> SEQ ID NO 14
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 14
gacaagggca tcaagagtag tatc                                            24

<210> SEQ ID NO 15
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 15
atgatgcgcc tgataatgct                                                 20

<210> SEQ ID NO 16
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 16
ggcaaacagt atgaagcacg a                                               21

<210> SEQ ID NO 17
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 17
catttggatc aatggaggat g                                               21

<210> SEQ ID NO 18
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 18
ctatggctgt ggcctgcttt gca                                             23

<210> SEQ ID NO 19
<211> LENGTH: 33
<212> TYPE: DNA
<213> ORGANISM: Artificial Sequence

```
<220> FEATURE:
<223> OTHER INFORMATION: Chemically Synthesized

<400> SEQUENCE: 19
aaaactcgag ctatggctgt ggcctgcttt gca                                33

<210> SEQ ID NO 20
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 20
aaaacaattg gcgcctggag ggaggaga                                      28

<210> SEQ ID NO 21
<211> LENGTH: 35
<212> TYPE: DNA
<213> ORGANISM: Artificial Sequence
<220> FEATURE:
<223> OTHER INFORMATION: Chemically Synthesized

<400> SEQUENCE: 21
aaaacaattg atgatcaatc agacaatcac tagaa                              35

<210> SEQ ID NO 22
<211> LENGTH: 63
<212> TYPE: DNA
<213> ORGANISM: Artificial Sequence
<220> FEATURE:
<223> OTHER INFORMATION: Chemically Synthesized

<400> SEQUENCE: 22
tgcaggctgc agagctccta ggctcgagtt aacactagta agcttaatta agatatcatt   60
tac                                                                 63

<210> SEQ ID NO 23
<211> LENGTH: 67
<212> TYPE: DNA
<213> ORGANISM: Artificial Sequence
<220> FEATURE:
<223> OTHER INFORMATION: Chemically Synthesized

<400> SEQUENCE: 23
aattgtaaat gatatcttaa ttaagcttac tagtgttaac tcgagcctag gagctctgca   60
gcctgca                                                             67

<210> SEQ ID NO 24
<211> LENGTH: 47
<212> TYPE: DNA
<213> ORGANISM: Artificial Sequence
<220> FEATURE:
<223> OTHER INFORMATION: Chemically Synthesized

<400> SEQUENCE: 24
acttctgcag cggccgcgat cgttcaaaca tttggcaata aagtttc                 47

<210> SEQ ID NO 25
<211> LENGTH: 50
<212> TYPE: DNA
<213> ORGANISM: Artificial Sequence
<220> FEATURE:
<223> OTHER INFORMATION: Chemically Synthesized
```

```
<400> SEQUENCE: 25
tctaagcttg gcgccgctag cagatctgat ctagtaacat agatgacacc         50
```

PLANTS WITH INCREASED ACTIVITY OF A STARCH PHOSPHORYLATING ENZYME

This application is a divisional of U.S. patent application Ser. No. 12/774,420, filed May 5, 2010, which is a divisional of U.S. patent application Ser. No. 10/591,428, filed Sep. 1, 2006, which is the U.S. National Stage of International Application PCT/EP05/002449, filed Mar. 4, 2005, which claims priority to U.S. Provisional Patent Application 60/549,945, filed Mar. 5, 2004, EP 04090086.2, filed Mar. 5, 2004, and EP 04090121.7, filed Mar. 29, 2004, the contents of each are hereby incorporated by reference in their entirety.

The present invention relates to plant cells and plants that are genetically modified, whereby the genetic modification leads to an increase in the activity of a starch phosphorylating OK1 protein in comparison to corresponding wild type plant cells or wild type plants that have not been genetically modified. The present invention also relates to means and methods for the manufacture of such plant cells and plants. These types of plant cells and plants synthesise a modified starch. Therefore, the present invention also concerns the starch synthesised from the plant cells and plants according to the invention, methods for the manufacture of this starch, and the manufacture of starch derivatives of this modified starch, as well as flours containing starches according to the invention.

In addition, the present invention relates to nucleic acids, coding starch phosphorylating OK1 proteins, vectors, host cells, plant cells, and plants containing such nucleic acid molecules. The present addition also involves OK1 proteins, which exhibit starch-phosphorylating activity.

With regard to the increasing importance currently attributed to plant constituents as renewable raw material sources, one of the tasks of biotechnological research is to endeavour to adapt these plant raw materials to suit the requirements of the processing industry. Furthermore, in order to enable regenerating raw materials to be used in as many areas of application as possible, it is necessary to achieve a large variety of materials.

Polysaccharide starch is made up of chemically uniform base components, the glucose molecules, but constitutes a complex mixture of different molecule forms, which exhibit differences with regard to the degree of polymerisation and branching, and therefore differ strongly from one another in their physical-chemical characteristics. Discrimination is made between amylose starch, an essentially unbranched polymer made from alpha-1,4-glycosidically linked glucose units, and the amylopectin starch, a branched polymer, in which the branches come about by the occurrence of additional alpha-1,6-glycosidic links. A further essential difference between amylose and amylopectin lies in the molecular weight. While amylose, depending on the origin of the starch, has a molecular weight of $5 \times 10^5$-$10^6$ Da, that of the amylopectin lies between $10^7$ and $10^6$ The two macromolecules can be differentiated by their molecular weight and their different physical-chemical characteristics, which can most easily be made visible by their different iodine bonding characteristics.

Amylose has long been looked upon as a linear polymer, consisting of alpha-1,4-glycosidically linked alpha-D-glucose monomers. In more recent studies, however, the presence of alpha-1,6-glycosidic branching points (ca. 0.1%) has been shown (Hizukuri and Takagi, Carbohydr. Res. 134, (1984), 1-10; Takeda et al., Carbohydr. Res. 132, (1984), 83-92).

The functional characteristics of starches, such as for example the solubility, the retrogradation behaviour, the water binding capacity, the film-forming characteristics, the viscosity, the gelatinisation characteristics, the freezing-thawing stability, the acid stability, the gel strength and the size of the starch grain, are affected amongst other things by the amylose/amylopectin ratio, the molecular weight, the pattern of the side chain distribution, the ion concentration, the lipid and protein content, the average grain size of the starch, the grain morphology of the starch etc. The functional characteristics of starch are also affected by the phosphate content, a non-carbon component of starch. Here, differentiation is made between phosphate, which is bonded covalently in the form of monoesters to the glucose molecules of the starch (described in the following as starch phosphate), and phosphate in the form of phospholipids associated with the starch.

The starch phosphate content varies depending on the type of plant. Therefore, certain maize mutants, for example, synthesise a starch with increased starch phosphate content (waxy maize 0.002% and high-amylose maize 0.013%), while conventional types of maize only have traces of starch phosphate. Similarly small amounts of starch phosphate are found in wheat (0.001%), while no evidence of starch phosphate has been found in oats and sorghum. Small amounts of starch phosphate have also been fount in rice mutants (waxy rice 0.003%), and in conventional types, of rice (0.013%). Significant amounts of starch phosphate have been shown in plants, which synthesise tuber or root storage starch, such as tapioca (0.008%), sweet potato (0.011%), arrowroot (0.021%) or potato (0.089%) for example. The percentage values for the starch phosphate content quoted above refer to the dry weight of starch in each case, and have been determined by Jane et al. (1996, Cereal Foods World 41 (11), 827-832).

Starch phosphate can be present in the form of monoesters at the C-2, C-3 or C-6 position of polymerised glucose monomers (Takeda and Hizukuri, 1971, Starch/Stärke 23, 267-272). The phosphate distribution of phosphate in starch synthesised by plants is generally characterised in that approximately 30% to 40% of residual phosphate at the C-3 position, and approximately 60% to 70% of the residual phosphate at the C-6 position, of the glucose molecule are covalently bonded (Blennow et al., 2000, Int. J. of Biological Macromolecules 27, 211-218). Blennow et al. (2000, Carbohydrate Polymers 41, 163-174) have determined a starch phosphate content, which is bonded in the C-6 position of the glucose molecules, for different starches such as, for example, potato starch (between 7.8 and 33.5 nMol per mg of starch, depending on the variety), starch from different *Curcuma* species (between 1.8 and 63 nMol per mg), tapioca starch (2.5 nMol per mg of starch), rice starch (1.0 nMol per mg of starch), mung bean starch (3.5 nMol per mg of starch) and sorghum starch (0.9 nMol per mg of starch). These authors have been unable to show any starch phosphate bonded at the C-6 position in barley starch and starches from different waxy mutants of maize. Up to now, it has not been possible to establish a connection between the genotype of a plant and the starch phosphate content (Jane et al., 1996, Cereal Foods World 41 (11), 827-832). It is therefore currently not possible to affect the starch phosphate content in plants by means of breeding measures.

Previously, only one protein has been described, which facilitates the introduction of covalent bonds of phosphate residues to the glucose molecules of starch. This protein has the enzymatic activity of an alpha-glucan-water dikinase (GWD, E.C.: 2.7.9.4) (Ritte et al., 2002, PNAS 99, 7166-7171), is frequently described in the literature as R1, and is bonded to the starch grains of the storage starch in potato tubers (Lorberth et al., 1998, Nature Biotechnology 16, 473-477). In the reaction catalysed by R1, the educts alpha-1,4- glucan (starch), adenosintriphosphate (ATP) and water are converted to the products glucan-phosphate (starch phosphate), monophosphate and adenosine monophosphate. In doing so, the residual gamma phosphate of the ATP is transferred to water, and the residual beta phosphate of the ATP is transferred to the glucan (starch). R1 transfers the residual beta phosphate of ATP to the C-6 and the C-3 position of the glucose molecules of alpha-1,4-glucans in vitro. The ratio of C-6 phosphate to C-3 phosphate, which is obtained in the in vitro reaction, is the same as the ratio, which is present in starch isolated from plants (Ritte et al., 2002, PNAS 99, 7166-7171). As about 70% of the starch phosphate present in potato starch is bonded to the glucose monomers of the starch in the C-6 position and about 30% in the C-3 position, this means that R1 preferably phosphorylates the C-6 position of the glucose molecules. Furthermore, it has been shown that by the use of amylopectin from maize, amongst other things, R1 can phosphorylate alpha-1,4-glucans, which do not yet contain covalently bonded phosphate (Ritte et al., 2002, PNAS 99, 7166-7171), i.e. R1 is able to introduce phosphate de novo into alpha-1,4-glucans.

Nucleic acid sequences, and the amino acid sequences corresponding to them, coding an R1 protein, are described from different species, such as, for example, potato (WO 97 11188, GenBank Acc.: AY027522, Y09533), wheat (WO 00 77229, U.S. Pat. No. 6,462,256, GenBank Acc.: AAN93923, GenBank Acc.: AR236165), rice (GenBank Acc.: AAR61445, GenBank Acc.: AR400814), maize (GenBank Acc.: AAR61444, GenBank Acc.: AR400813), soya bean (GenBank Acc.: AAR61446, GenBank Acc.: AR400815), citrus (GenBank Acc.: AY094062) and *Arabidopsis* (GenBank Acc.: AF312027).

Wheat plants, which exhibit increased activity of an R1 protein due to overexpression of an R1 potato gene, are described in WO 02 34923. These plants synthesise a starch with significant quantities of starch phosphate at the C-6 position of the glucose molecules in comparison to corresponding wild type plants, in which no starch phosphate could be detected.

Further proteins, which catalyse a reaction, which introduce covalently bonded phosphate groups into the starch, have not previously been described. Enzymes, which preferably introduce phosphate groups in the C-3 position and/or the C-2 position of the glucose molecules of starch, are also unknown. Apart from the increase of the starch phosphate content in plants, there are therefore also no available ways of specifically influencing the phosphorylation of starch in plants, of modifying the phosphate distribution within the starch synthesised by plants and/or of further increasing the starch phosphate content.

The object of the present invention is therefore based on providing modified starches with increased phosphate content and/or modified phosphate distribution, as well as plant cells and/or plants, which synthesise such a modified starch, as well as means and methods for producing said plants and/or plant cells.

This problem is solved by the embodiments described in the claims.

The present invention therefore relates to genetically modified plant cells and genetically modified plants, characterised in that the plant cells or plants have an increased activity of at least one OK1 protein in comparison with corresponding wild type plant cells or wild type plants that have not been genetically modified.

A first aspect of the present invention relates to a plant cell or plant, which is genetically modified, wherein the genetic modification leads to an increase in the activity of at least one OK1 protein in comparison with corresponding wild type plant cells or wild type plants that have not been genetically modified.

At the same time, the genetic modification can be any genetic modification, which leads to an increase in the activity of at least one OK1 protein in comparison with corresponding wild type plant cells or wild type plants that have not been genetically modified.

In conjunction with the present invention, the term "wild type plant cell" means that the plant cells concerned were used as starting material for the manufacture of the plant cells according to the invention, i.e. their genetic information, apart from the introduced genetic modification, corresponds to that of a plant cell according to the invention.

In conjunction with the present invention, the term "wild type plant" means that the plants concerned were used as starting material for the manufacture of the plants according to the invention, i.e. their genetic information, apart from the introduced genetic modification, corresponds to that of a plant according to the invention.

In conjunction with the present invention, the term "corresponding" means that, in the comparison of several objects, the objects concerned that are compared with one another have been kept under the same conditions. In conjunction with the present invention, the term "corresponding" in conjunction with wild type plant cell or wild type plant means that the plant cells or plants, which are compared with one another, have been raised under the same cultivation conditions and that they have the same (cultivation) age.

The term "increased activity of at least one OK1 protein" within the framework of the present invention means an increase in the expression of endogenous genes, which code the OK1 proteins, and/or an increase in the quantity of OK1 proteins in the cells, and/or an increase in the enzymatic activity of OK1 proteins in the cells.

The increase in the expression can be determined by measuring the quantity of OK1 proteins coding transcripts, for example; e.g. by way of Northern Blot analysis or RT-PCR. An increase preferably means an increase in the quantity of transcripts of at least 50%, preferably at least 70%, more preferably at least 85%, and most preferably at least 100%, in comparison to corresponding cells that have not been genetically modified. An increase in the quantity of transcripts coding an OK1 protein also means that plants or plant cells, which do not exhibit any detectable quantities of transcripts coding an OK1 protein, show detectable quantities of transcripts coding an OK1 protein following genetic modification according to the invention.

The increase in the amount of protein of an OK1 protein, which results in increased activity of this protein in the plant cells concerned, can, for example, be determined by immunological methods such as Western blot analysis, ELISA (Enzyme Linked Immuno Sorbent Assay) or RIA (Radio Immune Assay). Here, an increase preferably means an increase in the amount of OK1 protein in comparison with corresponding plant cells that have not been genetically modified by at least 50%, in particular by at least 70%, preferably by at least 85% and particularly preferably by at least 100%. An increase in the amount of OK1 protein also means that plants or plant cells that do not have any detectable OK1 protein activity exhibit a detectable quantity of OK1 protein following genetic modification according to the invention.

Methods for manufacturing antibodies, which react specifically with a certain protein, i.e. which bond specifically to said protein, are known to the person skilled in the art (see, for example, Lottspeich and Zorbas (Eds.), 1998, Bioanalytik, Spektrum akad, Verlag, Heidelberg, Berlin, ISBN 3-8274-

0041-4). The manufacture of such antibodies is offered by some companies (e.g. Eurogentec, Belgium) as a contract service. A possible way of manufacturing antibodies, which specifically react with an OK1 protein, is described below (see Example 10).

Within the framework of the present invention, the term "OK1 protein" is to be understood to mean a protein, which transfers a phosphate residue of ATP onto already phosphorylated starch (P-starch). Starches isolated from leaves of an *Arabisopsis thaliana* sex1-3 mutant have no detectable amounts of covalently bonded phosphate residues and are not phosphorylated by an OK1 protein, i.e. an OK1 protein according to the invention requires already phosphorylated starch as a substrate for transferring further phosphate residues.

Preferably, the residual beta phosphate of the ATP is transferred from an OK1 protein to the starch, and the residual gamma phosphate of the ATP is transferred to water. A further reaction product produced by a phosphorylating reaction of P-starch carried out using an OK1 protein is AMP (adenosine monophosphate). An OK1 protein is therefore described as [phosphorylated-alpha-glucan]-water-dikinase ([P-glucan]-water-dikinase) or as [phosphorylated-starch]-water-dikinase.

Preferably, an additional phosphate monoester bond is produced in the C-6 position and/or in the C-3 position of a glucose molecule of the P-starch, which is phosphorylated by an OK1 protein. In the phosphorylation of P-starch catalysed by an OK1 protein, it is particularly preferred if more additional phosphate monoester bonds are produced in the C-3 position in comparison with phosphate monoester bonds in the C-6 position of the glucose molecules of the P-starch concerned.

Amino acid sequences, which code OK1 proteins, contain a phosphohistidine domain. Phosphohistidine domains are described, for example, by Tien-Shin Yu et al. (2001, Plant Cell 13, 1907-1918). Phosphohistidine domains of OK1 proteins coding amino acids preferably contain two histidines.

In the catalysis of a phosphorylating reaction of a P-starch by means of an OK1 protein, a phosphorylated OK1 protein is produced as an intermediate product, in which a phosphate residue of ATP is covalently bonded to an amino acid of the OK1 protein. The intermediate product is produced by autophosphorylation of the OK1 protein, i.e. the OK1 protein itself catalyses the reaction, which leads to the intermediate product. Preferably, a histidine residue of the amino acid sequence coding an OK1 protein is phosphorylated as a result of the autophosphorylation process, particularly preferably a histidine residue, which is part of a phosphohistidine domain.

Furthermore, OK1 proteins according to the invention have an increased bonding activity to P-starch in comparison with non-phosphorylated starches.

As no enzymes have previously been described, which require P-starch as a substrate in order to phosphorylate them further, it has also previously not been possible to increase the starch phosphate content of already phosphorylated starch in plants above a certain quantity. This is now possible with the utilisation of a protein according to the invention or a nucleic acid molecule according to the invention for the genetic modification of plants. The clarification of the function of an OK1 protein, and thus the provision of an OK1 protein, leads to the fact that plants can now be genetically modified in such a way that they synthesise a starch with modified characteristics. The modification of the phosphate distribution in starch synthesised by plants was previously not possible due to the lack of available means. Due to the provision by the present invention of proteins and nucleic acids according to the invention, it is now also possible to modify the phosphate ratio in native starches.

In conjunction with the present invention, the term "increased bonding activity" is to be understood to mean an increased affinity of a protein to a first substrate in comparison with a second substrate. That is to say, the amount of protein, which, under the same incubation conditions, bonds to a first substrate to a greater extent in comparison with a second substrate, exhibits increased bonding activity to the first substrate.

In conjunction with the present invention, the term "starch phosphate" is to be understood to mean phosphate groups covalently bonded to the glucose molecules of starch.

In conjunction with the present invention, the term "non-phosphorylated starch" is to be understood to mean a starch, which does not contain any detectable amounts of starch phosphate. Different methods of determining the amount of starch phosphate are described. Preferably, the method of determining the amount of starch phosphate described by Ritte et al. (2000, Starch/Stärke 52, 179-185) can be used. Particularly preferably, the determination of the amount of starch phosphate by means of $^{31}$P-NMR is carried out according to the method described by Kasemusuwan and Jane (1996, Cereal Chemistry 73, 702-707).

In conjunction with the present invention, the term "phosphorylated starch" or "P-starch" is to be understood to mean a starch, which contains starch phosphate.

The activity of an OK1 protein can be demonstrated, for example, by in vitro incubation of an OK1 protein using ATP, which contains a phosphate residue labeled in the beta position (labeled ATP). Preferably ATP is used, in which the phosphate residue is specifically labeled in the beta position, i.e. in which only the phosphate residue in the beta position has a marking. Preferably radioactively labeled ATP, particularly preferably ATP, in which the phosphate residue is specifically radioactively labeled in the beta position, and especially preferably ATP, in which the phosphate residue in the beta position is specifically labeled with $^{33}$P, is used. If an OK1 protein with labeled ATP and starches, which are not phosphorylated, are incubated, no phosphate is transferred to the starch due to OK1. Preferably, leaf starch of *Arabidopsis thaliana* mutant sex1-3 (Tien-Shin Yu et al., 2001, Plant Cell 13, 1907-1918) is used.

If, on the other hand, an OK1 protein with P-starch is incubated in the presence of labeled ATP, then labeled phosphate covalently bonded to the P-starch can subsequently be shown. Preferably, starch from leaves of *Arabidopsis thaliana*, particularly preferably starch from *Arabidopsis thaliana* sex1-3 mutants enzymatically phosphorylated by means of an R1 protein (Ritte et al., 2002, PNAS 99, 7166-7171) is used.

Labeled phosphate residues, which have been incorporated in P-starch due to an OK1 protein, e.g. by separating the labeled P-starch (e.g. by precipitation with ethanol, filtration, chromatographic methods etc.) from the rest of the reaction mixture and subsequently detecting the labeled phosphate residue in the P-starch fraction, can be shown. At the same time, the labeled phosphate residues bonded in the P-starch fraction can be demonstrated, for example, by determining the amount of radioactivity present in the P-starch fraction (e.g. by means of scintillation counters). Possible methods for demonstrating a protein, which requires P-starch as a substrate for a phosphorylating reaction, are described below under General Methods, Item 11 and in Example 6.

Which positions of the carbon atoms (C-2, C-3 or C-6) of the glucose monomers in P-starch are preferably phosphorylated by an OK1 protein can be determined, for example, by analysing the P-starches phosphorylated by a protein, as described by Ritte et al. (2002, PNAS 99, 7166-7171). For this purpose, a P-starch phosphorylated by a protein is hydrolysed using an acid, and subsequently analysed by means of anion exchange chromatography.

Preferably, the P-starch phosphorylated by an OK1 protein is analysed by means of NMR in order to establish which positions of the carbon atoms (C-2, C-3 or C-6) of the glucose monomers in the P-starch are phosphorylated. A particularly preferred method for identifying the C-atom positions of a glucose molecule of a starch, which are phosphorylated by a reaction catalysed by an OK1 protein, is described below under General Methods, Item 13.

A phosphorylated protein, which is produced as an intermediate product in the phosphorylation of P-starch facilitated by an OK1 protein, can be demonstrated as described, for example, by Ritte et al. (2002, PNAS 99, 7166-7171) for an R1 protein.

To demonstrate the presence of an autophosphorylated intermediate product, an OK1 protein is first incubated in the absence of starch with labeled ATP, preferably with ATP specifically labeled in the beta phosphate position, particularly preferably with ATP specifically labeled with $^{33}$P in the beta phosphate position. In parallel with this, a reaction preparation 2, which instead of labeled ATP contains corresponding amounts of non-labeled ATP however, is incubated under otherwise identical conditions. Subsequently, an excess of unlabeled ATP is added to reaction mixture 1 and a mixture of unlabeled ATP and labeled ATP (the same quantity of labeled ATP as was used previously in reaction mixture 1, and the same quantity of the excess of unlabeled ATP that was added to reaction mixture 1) is added to reaction mixture 2, and this is further incubated before adding P-starch to Part A of reaction mixture 1 (Part 1A) and to Part A of reaction mixture 2 (Part 2A). The reaction in the remaining Part 1B and Part 2B of the reaction mixture is stopped by denaturing the protein. Part B of the reaction mixture can be stopped by the methods known to the person skilled in the art, which lead to the denaturing of proteins, preferably by adding sodium lauryl sulphate (SDS). Part 1A and Part 2A of the reaction mixture are incubated for at least a further 10 minutes before these reactions are also stopped. The starch present in Part A and Part B of the respective reaction mixture is separated from the remainder of the reaction mixture. If the respective starch is separated by centrifugation, for example, then, on completion of centrifugation, the starch of the respective Part A or Part B of the reaction mixture is to be found in the sedimented pellet, and the proteins in the respective reaction mixture are to be found in the supernatant of the respective centrifugation. The supernatant of Part 1A or 2A respectively and Part 1B or 2B respectively of the reaction mixture can subsequently be analysed by denaturing acrylamide gel electrophoresis, for example, followed by autoradiography of the acrylamide gel obtained. To quantify the amount of radioactively labeled proteins, which have been separated by means of acrylamide gel electrophoresis, the so-called "phospho-imaging" method, for example, known to the person skilled in the art, can be used. If the autoradiography or the analysis by means of the "phospho-imager" of proteins in the centrifugation supernatant of Part B of reaction mixture 1 shows a significantly increased signal compared with the centrifugation excess of Part A of reaction mixture 1, then this shows that a protein facilitating a phosphorylation of starch occurs as an autophosphorylated intermediate product. Parts A and B of reaction mixture 2 serve as a control and should therefore not exhibit a significantly increased signal in the centrifugation supernatant in the autoradiography or in the analysis by means of the "phospho-imager".

In addition, the starch of the respective Part A of reaction mixture 1 and 2 remaining in the respective sedimented pellet can be investigated, if necessary after subsequent washing of the respective starches, for the presence of starch phosphate, which has a mark corresponding to the labeled ATP used. If the starches of Part A of reaction mixture 1 contain labeled phosphate residues, and if the autoradiography of the centrifugation supernatant of Part B of reaction mixture 1 shows a significantly increased signal in the autoradiography compared with the centrifugation supernatant of Part A of reaction mixture 1, then this shows that a phosphorylation of starch-facilitating protein is present as an autophosphorylated intermediate product. Parts A and B of reaction mixture 2 serve as a control and should therefore not exhibit a significantly increased signal for alpha-1,4-glucans labeled with $^{33}$P in the sedimented pellet containing alpha-1,4-glucans. Possible methods for demonstrating a phosphorylated OK1 protein intermediate product are described below under General Methods, Item 12 and in Example 7.

That an OK1 protein has an increased bonding activity to a P-starch compared with non-phosphorylated starch can be demonstrated by incubating the OK1 protein with P-starch and non-phosphorylated starch in separate preparations.

All non-phosphorylated starches are basically suitable for incubating OK1 proteins with non-phosphorylated starch. Preferably, a non-phosphorylated plant starch, particularly preferably wheat starch, and especially preferably granular leaf starch of an *Arabidopsis thaliana* mutant sex1-3 is used.

Methods for isolating starch from plants, for example, are known to the person skilled in the art. All methods known to the person skilled in the art are basically suitable for isolating non-phosphorylated starch from appropriate plant species. Preferably, the methods for isolating non-phosphorylated alpha-1,4-glucans described below are used (see General Methods Item 2).

All starches, which contain starch phosphate, are basically suitable for incubating OK1 proteins with P-starch. Chemically phosphorylated starches can also be used for this purpose. Preferably, P-starches are used for the incubation with OK1 proteins, particularly preferably a retrospectively enzymatically phosphorylated plant starch, especially preferably a retrospectively enzymatically phosphorylated plant granular starch, which has been isolated from a sex-1 mutant of *Arabidopsis thaliana*.

To demonstrate an increased bonding activity of OK1 proteins to P-starch compared with non-phosphorylated starch, OK1 proteins are incubated in separate preparations with P-starch (Preparation A) and with non-phosphorylated starch (Preparation B). After successful incubation, the proteins, which are not bonded to the relevant starches of preparations A and B, are separated from the starches and the proteins to which they are bonded. The bond between the proteins and the P-starch in Preparation A and the bond between the proteins and non-phosphorylated starch in Preparation B are Subsequently Removed, i.e. the Respective Proteins are Dissolved. The dissolved proteins of Preparation A and Preparation B can then be separated from the starches concerned, which are present in the respective preparations. Following this, the isolated P-starch bonding proteins of Preparation A and the isolated non-phosphorylated starch bonding proteins of Preparation B can be separated with the help of methods known to the person skilled in the art such as, for example, gel filtration, chromatographic methods, electrophoresis, SDS acrylamide gel electrophoresis etc. By comparing the amounts of separated proteins of Preparation A with the amounts of corresponding separated proteins of Preparation B, it can be determined whether a protein has an increased bonding activity with respect to P-starch compared with non-phosphorylated starch. Methods, which can be used to demonstrate a preferred bonding of proteins to P-starch compared with non-phosphorylated starch, are described below in (General Methods, Item 8 and Example 1).

The amino acid sequence shown in SEQ ID NO 2 codes an OK1 protein from *Arabidopsis thaliana* and the amino acid sequence shown under SEQ ID NO 4 codes an OK1 protein from *Oryza sativa*.

In a further embodiment of the present invention, amino acid sequences coding an OK1 protein have an identity of at least 60% with the sequence specified in SEQ ID NO 2 or SEQ ID NO 4, in particular of at least 70%, preferably of at least 80% and particularly preferably of at least 90% and especially preferably of at least 95%.

In a further embodiment of the present invention, the OK1 protein exhibits a phosphohistidine domain (Tien-Shin Yu et al., 2001, Plant Cell 13, 1907-1918). Amino acid sequences coding OK1 proteins contain a phosphohistidine domain, which exhibits an identity of at least 50%, in particular of at least 60%, preferably of at least 70%, particularly preferably of at least 80%, and more particularly preferably of at least 90% of the amino acid sequence of the phosphohistidine domain of the OK1 protein from *Arabidopsis thaliana* and *Oryza sativa*, specified under SEQ ID NO 5. The phosphohistidine domain preferably contains two histidines residues.

A further embodiment of the present invention relates to a genetically modified plant cell according to the invention or a genetically modified plant according to the invention, wherein the genetic modification consists in the introduction of at least one foreign nucleic acid molecule into the genome of the plant.

In this context, the term "genetic modification" means the introduction of homologous and/or heterologous foreign nucleic acid molecules into the genome of a plant cell or into the genome of a plant, wherein said introduction of these molecules leads to an increase in the activity of an OK1 protein.

The plant cells according to the invention or plants according to the invention are modified with regard to their genetic information by the introduction of a foreign nucleic acid molecule. The presence or the expression of the foreign nucleic acid molecule leads to a phenotypic change. Here, "phenotypic" change means preferably a measurable change of one or more functions of the cells. For example, the genetically modified plant cells according to the invention and the genetically modified plants according to the invention exhibit an increase in the activity of an OK1 protein due to the presence of or in the expression of the introduced nucleic acid molecule.

In conjunction with the present invention, the term "foreign nucleic acid molecule" is understood to mean such a molecule that either does not occur naturally in the corresponding wild type plant cells, or that does not occur naturally in the concrete spatial arrangement in wild type plant cells, or that is localised at a place in the genome of the plant cell at which it does not occur naturally in wild type plant cells. Preferably, the foreign nucleic acid molecule is a recombinant molecule, which consists of different elements, the combination or specific spatial arrangement of which does not occur naturally in plant cells.

In principle, the foreign nucleic acid molecule can be any nucleic acid molecule, which causes an increase in the activity of an OK1 protein in the plant cell or plant.

In conjunction with the present invention, the term "genome" is to be understood to mean the totality of the genetic material present in a plant cell. It is known to the person skilled in the art that, in addition to the cell nucleus, other compartments (e.g. plastids, mitochondria) also contain genetic material.

In a further embodiment, the plant cells according to the invention and the plants according to the invention are characterised in that the foreign nucleic acid molecule codes an OK1 protein, preferably an OK1 protein from *Arabidopsis thaliana* or an OK1 protein from *Oryza sativa*.

In a further embodiment, the foreign nucleic acid molecule codes an OK1 protein with the amino acid sequence specified in SEQ ID NO 2 or SEQ ID NO 4.

A large number of techniques are available for the introduction of DNA into a plant host cell. These techniques include the transformation of plant cells with T-DNA using *Agrobacterium tumefaciens* or *Agrobacterium rhizogenes* as the transformation medium, the fusion of protoplasts, injection, the electroporation of DNA, the introduction of DNA by means of the biolistic approach as well as other possibilities. The use of agrobacteria-mediated transformation of plant cells has been intensively investigated and adequately described in EP 120516; Hoekema, Ind.: The Binary Plant Vector System Offsetdrukkerij Kanters B. V., Alblasserdam (1985), Chapter V; Fraley et al., Crit. Rev. Plant Sci. 4, 1-46 and by An et al. EMBO J. 4, (1985), 277-287. For the potato transformation, see Rocha-Sosa et al., EMBO J. 8, (1989), 29-33, for example.

The transformation of monocotyledonous plants by means of vectors based on *Agrobacterium* transformation has also been described (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Bio/Technology 13, (1995), 486-492; Conner and Domisse, Int. J. Plant Sci. 153 (1992), 550-555; Ritchie et al, Transgenic Res. 2, (1993), 252-265). An alternative system to the transformation of monocotyledonous plants is transformation by means of the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), protoplast transformation, electroporation of partially permeabilised cells and the introduction of DNA by means of glass fibres. In particular, the transformation of maize has been described in the literature many times (cf. e.g. WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726).

The successful transformation of other types of cereal has also already been described, for example for barley (Wan and Lemaux, see above; Ritala et al., see above; Krens et al., Nature 296, (1982), 72-74) and for wheat (Nehra et al., Plant J. 5, (1994), 285-297; Becker et al., 1994, Plant Journal 5, 299-307). All the above methods are suitable within the framework of the present invention.

Amongst other things, plant cells and plants, which have been genetically modified by the introduction of an OK1 protein, can be differentiated from wild type plant cells and wild type plants respectively in that they contain a foreign nucleic acid molecule, which does not occur naturally in wild type plant cells or wild type plants, or in that such a molecule is present integrated at a place in the genome of the plant cell according to the invention or in the genome of the plant according to the invention at which it does not occur in wild type plant cells or wild type plants, i.e. in a different genomic environment. Furthermore, plant cells according to the invention and plants according to the invention of this type differ from wild type plant cells and wild type plants respectively in that they contain at least one copy of the foreign nucleic acid molecule stably integrated within their genome, possibly in addition to naturally occurring copies of such a molecule in the wild type plant cells or wild type plants. If the foreign nucleic acid molecule(s) introduced into the plant cells according to the invention or into the plants according to the invention is (are) additional copies of molecules already occurring naturally in the wild type plant cells or wild type plants respectively, then the plant cells according to the invention and the plants according to the invention can be differentiated from wild type plant cells or wild type plants respectively in particular in that this additional copy or these additional copies is (are) localised at places in the genome at which it does not occur (or they do not occur) in wild type plant cells or wild type plants. This can be verified, for example, with the help of a Southern blot analysis.

Furthermore, the plant cells according to the invention and the plants according to the invention can preferably be differentiated from wild type plant cells or wild type plants respectively by at least one of the following characteristics: If the foreign nucleic acid molecule that has been introduced is heterologous with respect to the plant cell or plant, then the plant cells according to the invention or plants according to the invention have transcripts of the introduced nucleic acid molecules. These can be verified, for example, by Northern blot analysis or by RT-PCR (Reverse Transcription Polymerase Chain Reaction). Plant cells according to the invention and plants according to the invention, which express an antisense and/or an RNAi transcript, can be verified, for example, with the help of specific nucleic acid probes, which are complimentary to the RNA (occurring naturally in the plant cell), which is coding for the protein. Preferably, the plant cells according to the invention and the plants according to the invention contain a protein, which is coded by an introduced nucleic acid molecule. This can be demonstrated by immunological methods, for example, in particular by a Western blot analysis.

If the foreign nucleic acid molecule that has been introduced is homologous with respect to the plant cell or plant, the plant cells according to the invention or plants according to the invention can be differentiated from wild type plant cells or wild type plants respectively due to the additional expression of the introduced foreign nucleic acid molecule, for example. The plant cells according to the invention and the plants according to the invention preferably contain transcripts of the foreign nucleic acid molecules. This can be demonstrated by Northern blot analysis, for example, or with the help of so-called quantitative PCR.

In a further embodiment, the plant cells according to the invention and the plants according to the invention are transgenic plant cells or transgenic plants respectively.

In a further embodiment, the present invention relates to plant cells according to the invention and plants according to the invention wherein the foreign nucleic acid molecule is chosen from the group consisting of:

a) Nucleic acid molecules, which code a protein with the amino acid sequence given under SEQ ID NO 2 or SEQ ID NO 4;
b) Nucleic acid molecules, which code a protein, which includes the amino acid sequence, which is coded by the insertion in plasmid A.t.-OK1-pGEM or the insertion in plasmid pMI50;
c) Nucleic acid molecules, which code a protein, the sequence of which has an identity of at least 60% with the amino acid sequence given under SEQ ID NO 2 or SEQ ID NO 4;
d) Nucleic acid molecules, which code a protein, the sequence of which has an identity of at least 60% with the amino acid sequence, which is coded by the coding region of the insertion in plasmid A.t.-OK1-pGEM or by the coding region of the insertion in plasmid pMI50;
e) Nucleic acid molecules, which include the nucleotide sequence shown under SEQ ID NO 1 or SEQ ID NO 3 or a complimentary sequence;
f) Nucleic acid molecules, which include the nucleotide sequence of the insertion contained in plasmid A.t.-OK1-pGEM or plasmid pMI50;
g) Nucleic acid molecules, which have an identity of at least 60% with the nucleic acid sequences described under a), b), e) or f);
h) Nucleic acid molecules, which hybridise with at least one strand of the nucleic acid molecules described under a), b), d), e) or f) under stringent conditions;
i) Nucleic acid molecules, the nucleotide sequence of which deviates from the sequence of the nucleic acid molecules identified under a), b), e) or f) due to the degeneration of the genetic code; and
j) Nucleic acid molecules, which represent fragments, allelic variants and/or derivatives of the nucleic acid molecules identified under a), b), c), d), e), f), g), h) or i).

The amino acid sequence shown in SEQ ID NO 2 codes an OK1 protein from *Arabidopsis thaliana* and the amino acid sequence shown in SEQ ID NO 4 codes an OK1 protein from *Oryza sativa*.

The proteins coded from the different varieties of nucleic acid molecules according to the invention have certain common characteristics. These can include, for example, biological activity, molecular weight, immunological reactivity, conformation etc, as well as physical characteristics such as, for example, the running behaviour in gel electrophoresis, chromatographic behaviour, sedimentation coefficients, solubility, spectroscopic characteristics, stability; optimum pH, optimum temperature etc. The molecular weight of the OK1 protein from *Arabidopsis thaliana* derived from the amino acid sequence shown under SEQ ID NO 2 is ca. 131 kDa and the molecular weight of the OK1 protein from *Oryza sativa* derived from the amino acid sequence shown under SEQ ID NO 4 is ca. 132 kDa. The derived molecular weight of a protein according to the invention therefore preferably lies in the range from 120 kDa to 145 kDa, preferably in the range from 120 kDa to 140 kDa, particularly preferably from 125 kDa to 140 kDa and especially preferably from 130 kDa to 135 kDa.

The amino acid sequences shown in SEQ ID NO 2 and SEQ ID NO 4 coding OK1 proteins from *Arabidopsis thaliana* and *Oryza sativa* respectively each contain a phosphohistidine domain. Preferably, an OK1 protein according to the invention therefore contains a phosphohistidine domain, which has an identity of at least 50%, preferably of at least 60%, particularly preferably of at least 80% and especially preferably of 90% with the phosphohistidine domain shown under SEQ ID NO 5.

The present invention relates to nucleic acid molecules, which code a protein with the enzymatic activity according to the invention of an OK1 protein, wherein the coded OK1 protein has an identity of at least 70%, preferably of at least 80%, particularly preferably of at least 90% and especially preferably of 95% with the amino acid sequence specified under SEQ ID NO 2 or SEQ ID NO 4.

A plasmid (A.t.-OK1-pGEM) containing a cDNA which codes for a protein according to the invention (A.t.-OK1) from *Arabidopsis thaliana* was deposited on 8 Mar. 2004 under the number DSM16264 and a plasmid (pM150) containing a cDNA which codes for further protein according to the invention (O.s.-OK1) from *Oryza sativa* was deposited on 24 Mar. 2004 under the number DSM16302 under the Budapest Treaty at the German Collection of Microorganisms and Cell Cultures GmbH, Mascheroder Weg 1b, 38124 Braunschweig, Germany.

The amino acid sequence shown in SEQ ID NO 2 can be derived from the coding region of the cDNA sequence integrated in plasmid A.t.-OK1-pGEM and codes for an OK1 protein from *Arabidopsis thaliana*. The amino acid sequence shown in SEQ ID NO 4 can be derived from the coding region of the cDNA sequence integrated in plasmid pMI50 and codes for an OK1 protein from *Oryza sativa*. The present invention therefore also relates to nucleic acid molecules, which code a protein with the enzymatic activity of an OK1 protein, which includes the amino acid sequence, which is coded by the insertion in plasmid A.t.-OK1-pGEM or by the insertion in plasmid pMI50, wherein the coded protein has an identity of at least 70%, preferably of at least 80%, particularly preferably of at least 90% and especially preferably of 95% with the amino acid sequence, which can be derived from the insertion in A.t.-OK1-pGEM or pMI50.

The nucleic acid sequence shown in SEQ ID NO 1 is a cDNA sequence, which includes the coding region for an OK1 protein from *Arabidopsis thaliana* and the nucleic acid sequence shown in SEQ ID NO 3 is a cDNA sequence, which includes the coding region for an OK1 protein from *Oryza sativa*.

The present invention therefore also relates to nucleic acid molecules, which code an OK1 protein and the coding region of the nucleotide sequences shown under SEQ ID NO 1 or SEQ ID NO 3 or sequences, which are complimentary thereto, nucleic acid molecules, which include the coding region of the nucleotide sequence of the insertion contained in plasmid A.t.-OK1-pGEM or in plasmid pMI50 and nucleic acid molecules, which have an identity of at least 70%, preferably of at least 80%, particularly preferably of at least 90% and especially preferably of at least 95% with the said nucleic acid molecules.

With the help of the sequence information of nucleic acid molecules according to the invention or with the help of a nucleic acid molecule according to the invention, it is possible for the person skilled in the art to isolate homologous sequences from other plant species, preferably from starch-storing plants, preferably from plant species of the genus *Oryza*, in particular *Oryza sativa* or from *Arabidopsis thaliana*. This can be carried out, for example, with the help of conventional methods such as the examination of cDNA or genomic libraries with suitable hybridisation samples. The person skilled in the art knows that homologous sequences can also be isolated with the help of (degenerated) oligonucleotides and the use of PCR-based methods. The examination of databases, such as are made available, for example, by EMBL (http://www.ebi.ac.uk/Tools/index.htm) or NCBI (National Center for Biotechnology Information, http://www.ncbi.nlm.nih.gov/), can also be used for identifying homologous sequences, which code for OK1 protein. In this case, one or more sequences are specified as a so-called query. This query sequence is then compared by means of statistical computer programs with sequences, which are contained in the selected databases. Such database queries (e.g. blast or fasta searches) are known to the person skilled in the art and can be carried out by various providers.

If such a database query is carried out, e.g. at the NCBI (National Center for Biotechnology Information, http://www.ncbi.nlm.nih.gov/), then the standard settings, which are specified for the particular comparison inquiry, should be used. For protein sequence comparisons (blastp), these are the following settings: Limit entrez=not activated; Filter=low complexity activated; Expect value=10; word size=3; Matrix=BLOSUM62; Gap costs: Existence=11, Extension=1.

For nucleic acid sequence comparisons (blastn), the following parameters must be set: Limit entrez=not activated; Filter=low complexity activated; Expect value=10; word size=11.

With such a database search, the sequences described in the present invention can be used as a query sequence in order to identify further nucleic acid molecules and/or proteins, which code an OK1 protein.

With the help of the described methods, it is also possible to identify and/or isolate nucleic acid molecules according to the invention, which hybridise with the sequence specified under SEQ ID NO 1 or under SEQ ID NO 3 and which code an OK1 protein.

Within the framework of the present invention, the term "hybridising" means hybridisation under conventional hybridisation conditions, preferably under stringent conditions such as, for example, are described in Sambrock et al., Molecular Cloning, A Laboratory Manual, 3rd edition (2001) Cold Spring Harbor Laboratory Press, Cold Spring Harbor, N.Y. ISBN: 0879695773, Ausubel et al., Short Protocols in Molecular Biology, John Wiley & Sons; 5th edition (2002), ISBN: 0471250929). Particularly preferably, "hybridising" means hybridisation under the following conditions:

Hybridisation buffer:
2×SSC; 10×Denhardt solution (Ficoll 400+PEG+BSA; Ratio 1:1:1); 0.1% SDS; 5 mM EDTA; 50 mM Na2HPO4; 250 µg/ml herring sperm DNA; 50 µg/ml tRNA; or 25 M sodium phosphate buffer pH 7.2; 1 mM EDTA; 7% SDS Hybridisation temperature:
T=65 to 68° C.
Wash buffer: 0.1×SSC; 0.1% SDS
Wash temperature: T=65 to 68° C.

In principle, nucleic acid molecules, which hybridise with the nucleic acid molecules according to the invention, can originate from any plant species, which codes an appropriate protein, preferably they originate from starch-storing plants, preferably from species of the (systematic) family Poacea, particularly preferably from *Oryza sativa*. Nucleic acid molecules, which hybridise with the molecules according to the invention, can, for example, be isolated from genomic or from cDNA libraries. The identification and isolation of nucleic acid molecules of this type can be carried out using the nucleic acid molecules according to the invention or parts of these molecules or the reverse complements of these molecules, e.g. by means of hybridisation according to standard methods (see, for example, Sambrook et al., Molecular Cloning, A Laboratory Manual, 3rd edition (2001) Cold Spring Harbor Laboratory Press, Cold Spring Harbor, N.Y. ISBN: 0879695773, Ausubel et al., Short Protocols in Molecular Biology, John Wiley & Sons; 5th edition (2002), ISBN: 0471250929) or by amplification using PCR.

Nucleic acid molecules, which exactly or essentially have the nucleotide sequence specified under SEQ ID NO 1 or SEQ ID NO 3 or parts of these sequences, can be used as hybridisation samples. The fragments used as hybridisation samples can also be synthetic fragments or oligonucleotides, which have been manufactured using established synthesising techniques and the sequence of which corresponds essentially with that of a nucleic acid molecule according to the invention. If genes have been identified and isolated, which hybridise with the nucleic acid sequences according to the invention, then a determination of this sequence and an analysis of the characteristics of the proteins coded by this sequence should be carried out in order to establish whether an OK1 protein is involved. Homology comparisons on the level of the nucleic acid or amino acid sequence and a determination of the enzymatic activity are particularly suitable for this purpose. The activity of an OK1 protein can take place, for example, as described above under General Methods, Item 11. A preferred bonding affinity to P-starch in comparison with non-phosphorylated starch and autophosphorylation of an OK1 protein can be demonstrated using the methods already described above and under General Methods, Items 8 and 12.

The molecules hybridising with the nucleic acid molecules according to the invention particularly include fragments, derivatives and allelic variants of the nucleic acid molecules according to the invention, which code an OK1 protein from plants, preferably from starch-storing plants, preferably from plant species of the genus *Oryza*, particularly preferably from *Oryza sativa* or *Arabidopsis thaliana*. In conjunction with the present invention, the term "derivative" means that the sequences of these molecules differ at one or more positions from the sequences of the nucleic acid molecules described above and have a high degree of identity with these sequences. Here, the deviation from the nucleic acid molecules described above can have come about, for example, due to deletion, addition, substitution, insertion or recombination.

In conjunction with the present invention, the term "identity" means a sequence identity over the whole length of the coding region of at least 60%, in particular an identity of at least 70%, preferably greater than 80%, particularly preferably greater than 90% and especially of at least 95%. In conjunction with the present invention, the term "identity" is to be understood to mean the number of amino acids/nucleotides (identity) corresponding with other proteins/nucleic acids, expressed as a percentage. Identity is preferably determined by comparing SEQ ID NO 2 or SEQ ID NO 4 for amino acids or SEQ. ID NO 1 or SEQ ID NO 3 for nucleic acids with other proteins/nucleic acids with the help of computer programs. If sequences that are compared with one another have different lengths, the identity is to be determined in such a way that the number of amino acids, which have the shorter sequence in common with the longer sequence, determines the percentage quotient of the identity. Preferably, identity is determined by means of the computer program ClustalW, which is well known and available to the public (Thompson et al., Nucleic Acids Research 22 (1994), 4673-4680). ClustalW is made publicly available by Julie Thompson (Thompson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW can also be downloaded from different Internet sites, including the IGBMC (Institut de Génétique et de Biologie Moléculaire et Cellulaire, B. P. 163, 67404 Illkirch Cedex, France; ftp://ftp-igbmc.u-strasbg.fr/pub/) and the EBI (ftp://ftp.ebi.ac.uk/pub/software/) as well as from all mirrored Internet sites of the EBI (European Bioinformatics Institute, Wellcome Trust Genome Campus, Hinxton, Cambridge CB10 1SD, UK). Preferably, Version 1.8 of the ClustalW computer program is used to determine the identity between proteins according to the invention and other proteins. In doing so, the following parameters must be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

Preferably, Version 1.8 of the ClustalW computer program is used to determine the identity between the nucleotide sequence of the nucleic acid molecules according to the invention, for example, and the nucleotide sequence of other nucleic acid molecules. In doing so, the following parameters must be set:
KTUPLE=2, TOPDIAGS=4, PAIRGAP=5, DNAMATRIX: IUB, GAPOPEN=10, GAPEXT=5, MAXDIV=40, TRANSITIONS: unweighted.

Furthermore, identity means that functional and/or structural equivalence exists between the nucleic acid molecules concerned or the proteins coded by them. The nucleic acid molecules, which are homologous to the molecules described above and constitute derivatives of these molecules, are generally variations of these molecules, which constitute modifications, which execute the same biological function. At the same time, the variations can occur naturally, for example they can be sequences from other plant species, or they can be mutants, wherein these mutants may have occurred in a natural manner or have been introduced by objective mutagenesis. The variations can also be synthetically manufactured sequences. The allelic variants can be both naturally occurring variants and also synthetically manufactured variants or variants produced by recombinant DNA techniques. Nucleic acid molecules, which deviate from nucleic acid molecules according to the invention due to degeneration of the genetic code, constitute a special form of derivatives.

The proteins coded from the different derivatives of nucleic acid molecules according to the invention have certain common characteristics. These can include, for example, biological activity, substrate specificity, molecular weight, immunological reactivity, conformation etc, as well as physical characteristics such as, for example, the running behaviour in gel electrophoresis, chromatographic behaviour, sedimentation coefficients, solubility, spectroscopic characteristics, stability; optimum pH, optimum temperature etc. Preferred characteristics of an OK1 protein have already been described in detail above and are to be applied here accordingly.

The nucleic acid molecules according to the invention can be any nucleic acid molecules, in particular DNA or RNA molecules, for example cDNA, genomic DNA, mRNA etc. They can be naturally occurring molecules or molecules manufactured by genetic or chemical synthesis methods. They can be single-stranded molecules, which either contain the coding or the non-coding strand, or double-stranded molecules.

A further embodiment of the present invention relates to plant cells according to the invention and plants according to the invention wherein the foreign nucleic acid molecule is chosen from the group consisting of a) T-DNA molecules, which, due, to integration into the plant genome, lead to an increase in the expression of at least one OK1 gene (T-DNA activation tagging);

b) DNA molecules that contain transposons, which lead to an increase in the expression of an OK1 gene by way of integration into the plant genome. (transposon activation tagging);

c) DNA molecules that code an OK1 protein, and that are linked with regulatory sequences, which provide the transcriptions in plant cells, and which lead to an increase in the OK1 protein activity in the cell.

d) Nucleic acid molecules introduced by means of in vivo mutagenesis, which lead to a mutation or an insertion of a heterologous sequence in at least one endogenous gene coding an OK1 protein, wherein the mutation or insertion causes an increase in the expression of a gene coding an OK1 protein.

In conjunction with the present invention, plant cells and plants according to the invention can also be manufactured by the use of so-called insertion mutagenesis (overview article: Thorneycroft et al., 2001, Journal of experimental Botany 52 (361), 1593-1601). Insertion mutagenesis is to be understood to mean particularly the insertion of transposons or so-called transfer DNA (T-DNA) into a gene or near a gene coding for an OK1 protein, whereby, as a result of which, the activity of an OK1 protein in the cell concerned is increased.

The transposons can be both those that occur naturally in the cell (endogenous transposons) and also those that do not occur naturally in said cell but are introduced into the cell (heterologous transposons) by means of genetic engineering methods, such as transformation of the cell, for example. Changing the expression of genes by means of transposons is known to the person skilled in the art. An overview of the use of endogenous and heterologous transposons as tools in plant biotechnology is presented in Ramachandran and Sundaresan (2001, Plant Physiology and Biochemistry 39, 234-252).

T-DNA insertion mutagenesis is based on the fact that certain sections (T-DNA) of Ti plasmids from *Agrobacterium* can integrate into the genome of plant cells. The place of integration in the plant chromosome is not defined, but can take place at any point. If the T-DNA integrates into a part of the chromosome or near a part of the chromosome, which constitutes a gene function, then this can lead to an increase in the gene expression and thus also to a change in the activity of a protein coded by the gene concerned.

Here, the sequences inserted into the genome (in particular transposons or T-DNA) are distinguished by the fact that they contain sequences, which lead to an activation of regulatory sequences of an OK1 gene ("activation tagging").

Plant cells and plants according to the invention can be produced by means of the so-called "activation tagging" method (see, for example, Walden et al., Plant J. (1991), 281-288; Walden et al., Plant Mol. Biol. 26 (1994), 1521-1528). These methods are based on activating endogenous promoters by means of "enhancer" sequences, such as the enhancer of the 35S RNA promoter of the cauliflower mosaic virus, or the octopine synthase enhancer.

In conjunction with the present invention, the term "T-DNA activation tagging" is to be understood to mean a T-DNA fragment, which contains "enhancer" sequences and which leads to an increase in the activity of at least one OK1 protein by integration into the genome of a plant cell.

In conjunction with the present invention, the term "transposon activation tagging" is to be understood to mean a transposon, which contains "enhancer" sequences and which leads to an increase in the activity of at least one OK1 protein by integration into the genome of a plant cell.

In another embodiment, the DNA molecules according to the invention, which code an OK1 protein, are linked with regulatory sequences, which initiate transcription in plant cells (promoters) and lead to an increase in OK1 protein activity in the cell. In this case, the nucleic acid molecules according to the invention are present in "sense" orientation to the regulatory sequences.

For expressing nucleic acid molecules according to the invention, which code an OK1 protein, these are preferably linked with regulatory DNA sequences, which guarantee transcription in plant cells. In particular, these include promoters. In general, any promoter that is active in plant cells is eligible for expression.

The promoter can be chosen so that expression takes place constitutively or only in a certain tissue, at a certain stage of the plant development or at a time determined by external influences. The promoter can be homologous or heterologous both with respect to the plant and with respect to the nucleic acid molecule.

Suitable promoters are, for example, the promoter of the 35S RNA of the cauliflower mosaic virus and the ubiquitin promoter from maize for constitutive expression, the patatin promoter B33 (Rocha-Sosa et al., EMBO J. 8 (1989), 23-29) for tuber-specific expression in potatoes or a promoter, which only ensures expression in photosynthetically active tissues, e.g. the ST-LS1 promoter (Stockhaus et al., Proc. Natl. Acad. Sci. USA 84 (1987), 7943-7947; Stockhaus et al., EMBO J. 8 (1989), 2445-2451) or, for endosperm-specific expression of the HMG promoter from wheat, the USP promoter, the phaseolin promoter, promoters of zein genes from maize (Pedersen et al., Cell 29 (1982), 1015-1026; Quatroccio et al., Plant Mol. Biol. 15 (1990), 81-93), glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218) or shrunken-1 promoter (Werr et al., EMBO J. 4 (1985), 1373-1380). However, promoters can also be used, which are only activated at a time determined by external influences (see for example WO 9307279). Promoters of heat-shock proteins, which allow simple induction, can be of particular interest here. Furthermore, seed-specific promoters can be used, such as the USP promoter from *Vicia faba*, which guarantees seed-specific expression in *Vicia faba* and other plants (Fiedler et al., Plant Mol. Biol. 22 (1993), 669-679; Baumlein et al., Mol. Gen. Genet. 225 (1991), 459-467).

Furthermore, a termination sequence (polyadenylation signal) can be present, which is used for adding a poly-A tail to the transcript. A function in the stabilisation of the transcripts is ascribed to the poly-A tail. Elements of this type are described in the literature (cf. Gielen et al., EMBO J. 8 (1989), 23-29) and can be exchanged at will.

Intron sequences can also be present between the promoter and the coding region. Such intron sequences can lead to stability of expression and to increased expression in plants (Callis et al., 1987, Genes Devel. 1, 1183-1200; Luehrsen, and Walbot, 1991, Mol. Gen. Genet. 225, 81-93; Rethmeier, et al., 1997; Plant Journal. 12(4):895-899; Rose and Beliakoff, 2000, Plant Physiol. 122 (2), 535-542; Vasil et al., 1989, Plant Physiol. 91, 1575-1579; XU et al., 2003, Science in China Series. C Vol. 46 No. 6, 561-569). Suitable intron sequences are, for example, the first intron of the sh1 gene from maize, the first intron of the polyubiquitin gene 1 from maize, the first intron of the EPSPS gene from rice or one of the two first introns of the PAT1 gene from *Arabidopsis*.

Furthermore, plant cells according to the invention and plants according to the invention can be manufactured by means of so-called "in situ activation". In this case, the introduced genetic modification effects a change in the regulatory sequences of endogenous OK1 genes, which leads to an increased expression of OK1 genes. Preferably, the activation of an OK1 gene takes place by "in vivo" mutagenesis of a promoter or of "enhancer" sequences of an endogenous OK1 gene. In doing so, a promoter or an "enhancer" sequence, for example, can be changed in such a way that the mutation produced leads to an increased expression of an OK1 gene in plant cells according to the invention or plants according to the invention in comparison with the expression of an OK1 gene in wild type plant cells or wild type plants. The mutation in a promoter or an "enhancer" sequence can also lead to OK1 genes in plant cells according to the invention or plants according to the invention being expressed at a time at which they would not be expressed in wild type plant cells or wild type plants.

In conjunction with the present invention, the term "OK1 gene" is understood to mean a nucleic acid molecule (cDNA, DNA), which codes an OK1 protein, preferably an OK1 protein from starch-storing plants, more preferably from *Arabidopsis thaliana*, and most preferably from rice.

During so-called "in vivo" mutagenesis, a hybrid RNA-DNA oligonucleotide ("chimeroplast") is introduced into plant cells by way of transformation (Kipp, P. B. et al., Poster Session at the "5th International Congress of Plant Molecular Biology, Sep. 21-27, 1997, Singapore; R. A. Dixon and C. J. Arntzen, Meeting report on "Metabolic Engineering in Transgenic Plants", Keystone Symposia, Copper Mountain, Colo., USA, TIBTECH 15, (1997), 441-447; international patent WO 9515972; Kren et al., Hepatology 25, (1997), 1462-1468; Cole-Strauss et al., Science 273, (1996), 1386-1389; Beetham et al., 1999, PNAS 96, 8774-8778).

A part of the DNA components of the RNA-DNA oligonucleotide is homologous to a nucleic acid sequence of an endogenous OK1 gene, but, in comparison with the nucleic acid sequence of an endogenous OK1 gene, it has a mutation or contains a heterologous region, which is surrounded by the homologous regions.

By way of base pairing of the homologous regions of the RNA-DNA oligonucleotide and of the endogenous nucleic acid molecule, followed by homologous recombination, the mutation contained in the DNA component of the RNA-DNA oligonucleotide or heterologous region can be transferred into the genome of a plant cell. This leads to an increase in the activity of one or more OK1 proteins.

All these methods are based on the introduction of a foreign nucleic acid molecule into the genome of a plant cell or plant and are therefore basically suitable for the manufacture of plant cells according to the invention and plants according to the invention.

Surprisingly, it has been found that plant cells according to the invention and plants according to the invention synthesise a modified starch in comparison with starch of corresponding wild type plant cells or wild type plants that have not been genetically modified.

The plant cells according to the invention and plants according to the invention synthesise a modified starch, which in its physical-chemical characteristics, in particular the starch phosphate content or the phosphate distribution, is changed in comparison with the synthesised starch in wild type plant cells or plants, so that this is better suited for special applications.

As no enzymes have previously been described, which exclusively phosphorylate P-starch, it has also previously not been possible to increase the starch phosphate content of already phosphorylated starch in plants over a certain level. This is now possible through the use of a protein according to the invention or a nucleic acid according to the invention for the genetic modification of plants.

It was not possible to distribute phosphates in starch synthesised from plants either, due to a lack of means available. Due to the provision of proteins and nucleic acids according to the present invention, it is now possible to alter the phosphate ratio in native starches as well.

Therefore, the present invention also includes plant cells and plants according to the invention, which synthesise a modified starch in comparison with corresponding wild type plant cells and wild type plants that have not been genetically modified.

In conjunction with the present invention, the term "modified starch" should be understood to mean that the starch exhibits changed physical-chemical characteristics in comparison to unmodified starch, which is obtainable from corresponding wild type plant cells or wild type plants.

In an additional embodiment of the present invention, plant cells or plants according to the invention synthesise a starch, which contains a high content of starch phosphate and/or an altered phosphate distribution in comparison to starch that has been isolated from corresponding wild type plant cells and wild type plants.

In conjunction with the current invention, the term "phosphate distribution" should be understood to mean the proportion of starch phosphate bonded to a glucose molecule in the C-2 position, C-3 position, or C-6 position, with respect to the total starch phosphate content in the starch.

In an additional embodiment of the present invention, plant cells or plants according to the invention synthesise a starch, which exhibits an altered ratio of C-3 phosphate to C-6 phosphate in comparison to starch from wild type plants that have not been genetically modified. Preferred here are starches, which have an increased proportion of starch phosphate bonded in the C-3 position compared with starch phosphate bonded in the C-6 position in comparison with starches from wild type plant cells and wild type plants that have not been genetically modified.

In conjunction with the present invention, the term "ratio of C-3 phosphate to C-6 phosphate" should be understood to mean the amount of starch phosphate, of which starch phosphate bonded to an alpha-1,4-glucan in the C-3 position or C-6 position, respectively, contributes to the sum of the starch phosphate bonded to the alpha-1,4-glucan in the C-3 position and C-6 position (C-3 position+C-6 position).

Different methods of determining the amount of starch phosphate are described. Preferably, the method of determining the amount of starch phosphate described by Ritte et al. (2000, Starch/Stärke 52, 179-185) can be used. Particularly preferably, the determination of the amount of starch phosphate by means of 31 P-NMR is carried out according to the method described by Kasemusuwan and Jane (1996, Cereal Chemistry 73, 702-707).

Furthermore, an object of the invention is genetically modified plants, which contain plant cells according to the invention. These types of plants can be produced from plant cells according to the invention by regeneration.

In principle, the plants according to the invention can be plants of any plant species, i.e. both monocotyledonous and dicotyledonous plants. Preferably they are useful plants, i.e. plants, which are cultivated by people for the purposes of food or for technical, in particular industrial purposes.

In a further embodiment, the plant according to the invention is a starch-storing plant.

In conjunction with the present invention, the term "starch-storing plants" means all plants with plant parts, which contain a storage starch, such as, for example, maize, rice, wheat, rye, oats, barley, cassava, potato, sago, mung bean, pea or sorghum.

In conjunction with the present invention, the term "potato plant" or "potato" means the plant species of the genus *Solanum*, particularly tuber-producing species of the genus *Solanum*, and in particular *Solanum tuberosum*.

In conjunction with the present invention, the term "wheat plant" means plant species of the genus *Triticum* or plants resulting from crosses with plants of the genus *Triticum*, particularly plant species of the genus *Triticum* or plants resulting from crosses with plants of the genus *Triticum*, which are used in agriculture for commercial purposes, and particularly preferably *Triticum aestivum*.

In conjunction with the present invention, the term "maize plant" means plant species of the genus *Zea*, particularly plant species of the genus *Zea*, which are used in agriculture for commercial purposes, particularly preferably *Zea mais*.

In an additional embodiment, the present invention relates to starch-storing plants according to the invention of the (systematic) family Poaceae. These are preferably maize or wheat plants.

The present invention also relates to propagation material of plants according to the invention containing a plant cell according to the invention.

Here, the term "propagation material" includes those constituents of the plant that are suitable for producing offspring by vegetative or sexual means. Cuttings, callus cultures, rhizomes or tubers, for example, are suitable for vegetative propagation. Other propagation material includes, for example, fruits, seeds, seedlings, protoplasts, cell cultures, etc. Preferably, the propagation material is tubers and particularly preferably grains, which contain endosperms.

In a further embodiment, the present invention relates to harvestable plant parts of plants according to the invention such as fruits, storage roots, roots, blooms, buds, shoots or stems, preferably seeds, grains or tubers, wherein these harvestable parts contain plant cells according to the invention.

Furthermore, the present invention also relates to a method for the manufacture of a genetically modified plant according to the invention, wherein
a) a plant cell is genetically modified, whereby the genetic modification leads to an increase in the activity of an OK1 protein in comparison with corresponding wild type plant cells that have not been genetically modified;
b) a plant is regenerated from plant cells from Step a); and
c) if necessary, further plants are produced with the help of the plants according to Step b).

The genetic modification introduced into the plant cell according to Step a) can basically be any type of genetic modification, which leads to an increase in the activity of an OK1 protein.

The regeneration of the plants according to Step (b) can be carried out using methods known to the person skilled in the art (e.g. described in "Plant Cell Culture Protocols", 1999, edt. by R. D. Hall, Humana Press, ISBN 0-89603-549-2).

The production of further plants according to Step (c) of the method according to the invention can be carried out, for example, by vegetative propagation (for example using cuttings, tubers or by means of callus culture and regeneration of whole plants) or by sexual propagation. Here, sexual propagation preferably takes place under controlled conditions, i.e. selected plants with particular characteristics are crossed and propagated with one another. In this case, the selection is preferably carried out in such a way that further plants, which are obtained in accordance with Step c), exhibit the genetic modification, which was introduced in Step a).

In a further embodiment of the method according to the invention, the genetic modification consists in the introduction of a foreign nucleic acid molecule according to the invention into the genome of the plant cell, wherein the presence or the expression of said foreign nucleic acid molecule leads to increased activity of an OK1 protein in the cell.

In a further embodiment of the method according to the invention, the genetic modification consists in the introduction of a foreign nucleic acid molecule into the genome of the plant cell, wherein the foreign nucleic acid molecule codes an OK1 protein.

In a further embodiment, the method according to the invention is used for manufacturing a genetically modified plant according to the invention for producing starch-storing plants.

In a further embodiment, the method according to the invention is used for producing maize or wheat plants according to the invention.

In a further embodiment of the method according to the invention, the foreign nucleic acid molecule is chosen from the group consisting of
a) Nucleic acid molecules, which code a protein with the amino acid sequence specified under SEQ ID NO 2 or SEQ ID NO 4;
b) Nucleic acid molecules, which code a protein that includes the amino acid sequence, which is coded by insertion into plasmid A.t.-OK1-pGE or insertion into plasmid pMI50;
c) Nucleic acid molecules, which code a protein, the amino acid sequence of which has an identity of at least 60% with the amino acid sequence specified under SEQ ID NO 2 or SEQ ID NO 4;
d) Nucleic acid molecules, which code a protein, the sequence of which has an identity of at least 60% of the amino acid sequence that is coded by insertion into plasmid A.t.-OK1-pGEM or insertion into plasmid pMI50;
e) Nucleic acid molecules, which include the nucleotide sequence shown under SEQ ID NO 1 or SEQ ID NO 3 or a complimentary sequence;
f) Nucleic acid molecules, which include the nucleotide sequence of insertion contained in the plasmid A.t.-OK1-pGEM or plasmid pMI50;
g) Nucleic acid molecules, the nucleic acid sequence of which has an identity of at least 70% with the nucleic acid sequences described under a), b), e), or f);
h) Nucleic acid molecules, which hybridise with at least one strand of the nucleic acid molecules described under a), b), e), or f) under stringent conditions;
i) Nucleic acid molecules, the nucleotide sequence of which deviates from the sequence of the nucleic acid molecules identified under a), b), e), or f) due to the degeneration of the genetic code, and
j) Nucleic acid molecules, which represent fragments, allelic variants and/or derivatives of the nucleic acid molecules identified under a), b), c), d), e), f), g), h) or i).

In a further embodiment of the method according to the invention, the foreign nucleic acid molecule is chosen from the group consisting of
a) T-DNA molecules, which lead to an increase in the expression of an OK1 gene through integration into the plant genome (T-DNA activation tagging);
b) DNA molecules, which contain transposons that lead to an increase in the expression of an OK1 gene through integration into the plant genome (transposon activation tagging);
c) DNA molecules, which code an OK1 protein and are linked to regulatory sequences that guarantee (initiate) the transcriptions in plant cells, and which lead to an increase in the activity of an OK1 protein in the cell;
d) Nucleic acid molecules introduced by way of in vivo mutagenesis, which lead to a mutation or an insertion in a heterologous sequence in at least one endogenous OK1 gene, wherein the mutation or insertion causes an increase in the expression of an OK1 gene.

In a further embodiment, the present invention relates to a method according to the invention, wherein the genetically modified plant synthesises a modified starch in comparison with starch from wild type plants that have not been genetically modified.

In a further embodiment of the method according to the invention, the plants according to the invention synthesise a modified starch, which has a higher starch phosphate content and/or a modified phosphate distribution in comparison with starch isolated from corresponding wild type plants.

In a further embodiment of the method according to the invention, the plants according to the invention synthesise a modified starch, which has a modified ratio of C-3 phosphate to C-6 phosphate in comparison with starch from wild type plants that have not been genetically modified. Particularly preferred here are starches, which have an increased proportion of starch phosphate bonded in the C-3 position compared with starch phosphate bonded in the C-6 position in comparison with starches from wild type plants that have not been genetically modified.

The present invention also relates to the plants obtainable by the method according to the invention.

Surprisingly, it has been found that starch isolated from plant cells according to the invention and plants according to the invention, which have an increased activity of an OK1 protein, synthesise a modified starch.

In particular, the increased quantities of starch phosphate in starches according to the invention provide the starches with surprising and advantageous properties. Starches according to the invention have an increased proportion of loaded groups due to the increased proportion of starch phosphate, which considerably affect the functional properties. Starch that contains loaded functional groups is particularly usable in the paper industry, where it is utilised for paper coating. Paper, which is coated with loaded molecules that also exhibit good adhesive properties, is particularly suitable for absorbing pigments, such as dye, printing inks, etc., for example.

The present invention also relates to modified starches obtainable from plant cells according to the invention or plants according to the invention, from propagation material according to the invention or from harvestable plant parts according to the invention.

In a further embodiment, the present invention relates to modified starch according to the invention from starch-storing plants, preferably from starch-storing plants of the (systematic) family Poaceae, particularly preferably from maize or wheat plants.

Furthermore the present invention relates to a method for the manufacture of a modified starch including the step of extracting the starch from a plant cell according to the invention or from a plant according to the invention, from propagation material according to the invention of such a plant and/or from harvestable plant parts according to the invention of such a plant, preferably from starch-storing parts according to the invention of such a plant. Preferably, such a method also includes the step of harvesting the cultivated plants or plant parts and/or the propagation material of these plants before the extraction of the starch and, further, particularly preferably the step of cultivating plants according to the invention before harvesting.

Methods for extracting starches from plants or from starch-storing parts of plants are known to the person skilled in the art. Furthermore, methods for extracting starch from different starch-storing plants are described, e.g. in Starch: Chemistry and Technology (Publisher: Whistler, BeMiller and Paschall (1994), 2nd Edition, Academic Press Inc. London Ltd; ISBN 0-12-746270-8; see e.g. Chapter XII, Page 412-468: Maize and Sorghum Starches: Manufacture; by Watson; Chapter XIII, Page 469-479: Tapioca, Arrowroot and Sago Starches: Manufacture; by Corbishley and Miller; Chapter XIV, Page 479-490: Potato starch: Manufacture and Uses; by Mitch; Chapter XV, Page 491 to 506: Wheat starch: Manufacture, Modification and Uses; by Knight and Oson; and Chapter XVI, Page 507 to 528: Rice starch: Manufacture and Uses; by Rohmer and Klem; Maize starch: Eckhoff et al., Cereal Chem. 73 (1996), 54-57, the extraction of maize starch on an industrial scale is generally achieved by so-called "wet milling".). Devices, which are in common use in methods for extracting starch from plant material are separators, decanters, hydrocyclones, spray dryers and fluid bed dryers.

In conjunction with the present invention, the term "starch-storing parts" is to be understood to mean such parts of a plant in which, in contrast to transitory leaf starch, starch is stored as a deposit for surviving for longer periods. Preferred starch-storing plant parts are, for example, tubers, storage roots and grains, particularly preferred are grains containing an endosperm, especially particularly preferred are grains containing an endosperm of maize or wheat plants.

Modified starch obtainable by a method according to the invention for manufacturing modified starch is also the subject matter of the present invention.

In a further embodiment of the present invention, the modified starch according to the invention is native starch.

In conjunction with the present invention, the term "native starch" means that the starch is isolated from plants according to the invention, harvestable plant plants according to the invention, starch-storing parts according to the invention or propagation material of plants according to the invention by methods known to the person skilled in the art.

Furthermore, the use of plant cells according to the invention or plants according to the invention for manufacturing a modified starch are the subject matter of the present invention.

The person skilled in the art knows that the characteristics of starch can be changed by thermal, chemical, enzymatic or mechanical derivation, for example. Derived starches are particularly suitable for different applications in the foodstuffs and/or non-foodstuffs sector. The starches according to the invention are better suited to be an initial substance for the manufacture of derived starches than for conventional starches, since they exhibit a higher proportion of reactive functional groups due to the higher starch phosphate content.

The present invention therefore also relates to the manufacture of a derived starch, wherein modified starch according to the invention is derived retrospectively.

In conjunction with the present invention, the term "derived starch" is to be understood to mean a modified starch according to the invention, the characteristics of which have been changed after isolation from plant cells with the help of chemical, enzymatic, thermal or mechanical methods.

In a further embodiment of the present invention, the derived starch according to the invention is starch that has been treated with heat and/or acid.

In a further embodiment, the derived starches are starch ethers, in particular starch alkyl ethers, O-allyl ethers, hydroxylalkyl ethers, O-carboxylmethyl ethers, nitrogen-containing starch ethers, phosphate-containing starch ethers or sulphur-containing starch ethers.

In a further embodiment, the derived starches are cross-linked starches.

In a further embodiment, the derived starches are starch graft polymers.

In a further embodiment, the derived starches are oxidised starches.

In a further embodiment, the derived starches are starch esters, in particular starch esters, which have been introduced into the starch using organic acids. Particularly preferably these are phosphate, nitrate, sulphate, xanthate, acetate or citrate starches.

The derived starches according to the invention are suitable for different applications in the pharmaceutical industry and in the foodstuffs and/or non-foodstuffs sector. Methods for manufacturing derived starches according to the invention are known to the person skilled in the art and are adequately described in the general literature. An overview on the manufacture of derived starches can be found, for example, in Orthoefer (in Corn, Chemistry and Technology, 1987, eds. Watson and Ramstad, Chapter 16, 479-499).

Derived starch obtainable by the method according to the invention for manufacturing a derived starch is also the subject matter of the present invention.

Furthermore, the use of modified starches according to the invention for manufacturing derived starch is the subject matter of the present invention.

Starch-storing parts of plants are often processed into flours. Examples of parts of plants from which flours are produced, for example, are tubers of potato plants and grains of cereal plants. For the manufacture of flours from cereal plants, the endosperm-containing grains of these plants are ground and strained. Starch is a main constituent of the endosperm. In the case of other plants, which do not contain endosperm, and which contain other starch-storing parts instead such as tubers or roots, for example, flour is frequently produced by mincing, drying, and subsequently grinding the storing organs concerned. The starch of the endosperm or contained within starch-storing parts of plants is a fundamental part of the flour, which is produced from those plant parts, respectively. The characteristics of flours are therefore affected by the starch present in the respective flour. Plant cells according to the invention and plants according to the invention synthesise a modified starch in comparison with wild type plant cells and wild type plants that have not been genetically modified. Flours produced from plant cells according to the invention, plants according to the invention, propagation material according to the invention, or harvestable parts according to the invention, therefore exhibit modified properties. The properties of flours can also be affected by mixing starch with flours or by mixing flours with different properties.

Therefore, an additional subject of the invention relates to flours, which contain a starch according to the invention.

A further subject of the present invention relates to flours, which are produced from plant cells according to the invention, plants according to the invention, from starch-storing parts of plants according to the invention, from propagation material according to the invention, or from harvestable plant parts according to the invention. Preferred starch-storing parts of plants according to the invention are tubers, storage roots, and grains containing an endosperm. Tubers preferably come from potato plants, and grains preferably come from plants of the (systematic) family Poaceae, while grains particularly preferably come from maize or wheat plants.

In conjunction with the present invention, the term "flour" is to be understood to mean a powder obtained by grinding plant parts. Plant parts are possibly dried before grinding, and minced and/or strained after grinding.

Flours according to the invention are characterised in that they contain starch, which exhibits a modified phosphate content and/or a modified phosphate distribution particularly due to its increased water binding capacity. This is desirable in the processing of flours in the foodstuffs industry for many applications, and in particular in the manufacture of baked goods, for example.

A further subject of the present invention is a method for the manufacture of flours, including the step of grinding plant cells according to the invention, plants according to the invention, parts of plants according to the invention, starch-storing parts of plants according to the invention, propagation material according to the invention, or harvestable material according to the invention.

Flours can be produced by grinding starch-storing parts of plants according to the invention. Methods for the manufacture of flours are known to the person skilled in the art. A method for the manufacture of flours preferably includes the step of harvesting the cultivated plants or plant parts and/or the propagation material or the starch-storing parts of these plants before grinding, and particularly preferably includes the additional step of cultivating plants according to the invention before harvesting.

In conjunction with the present invention, the term "parts of plants" should be understood to mean all parts of the plants that, as constituents, constitute a complete plant in their entirety. Parts of plants are scions, leaves, rhizomes, roots, knobs, tubers, pods, seeds, or grains.

In a further embodiment of the present invention, the method for the of flours includes processing plants according to the invention, starch-storing plants according to the invention, propagation material according to the invention, or harvestable material according to the invention before grinding.

In this case, processing can be heat treatment and/or drying, for example. Heat treatment followed by a drying of the heat-treated material is used in the manufacture of flours from storage roots or tubers such as potato tubers, for example, before grinding. The mincing of plants according to the invention, starch-storing parts of plants according to the invention, propagation material according to the invention, or harvestable material according to the invention before grinding can also represent processing in the sense of the present invention. The removal of plant tissue before grinding, such as e.g. grain husks, also represents processing before grinding in the sense of the present invention.

In a further embodiment of the present invention, the method for the manufacture of flours includes processing the ground product after grinding.

In this case, the ground product can be strained after grinding, for example, in order to produce various types of flours, for example.

A further subject of the present invention is the use of genetically modified plant cells according to the invention or plants according to the invention for the manufacture of flours.

It is also an object of the present invention to provide means such as DNA molecules, for example, for the production of plant cells according to the invention and plants according to the invention, which synthesise a modified starch in comparison with modified wild type plant cells or wild type plants that have not been genetically modified.

The present invention therefore also relates to nucleic acid molecules, which code for a protein with the enzymatic activity of an OK1 protein, chosen from the group consisting of a) Nucleic acid molecules, which code a protein with the amino acid sequence specified under SEQ ID NO 2 or SEQ ID NO 4;

Nucleic acid molecules, which code a protein that includes the amino acid sequence, which is coded by insertion into the plasmid A.t.-OK1-pGEM or insertion into the plasmid pMI50;

c) Nucleic acid molecules, which code a protein, the sequence of which has an identity of at least 60% with the amino acid sequence specified under SEQ ID NO 2 or SEQ ID NO 4;

d) Nucleic acid molecules, which code a protein, the sequence of which has an identity of at least 60% of the amino acid sequence, which is coded by insertion into the plasmid A.t.-OK1-pGEM or insertion into the plasmid DSM pMI50;
e) Nucleic acid molecules, which include the nucleotide sequence specified under SEQ ID NO 1 or SEQ ID NO 3 or a complimentary sequence;
f) Nucleic acid molecules, which include the nucleotide sequence of the insertion contained in the plasmid A.t.-OK1-pGEM or the plasmid pMI50;
g) Nucleic acid molecules, which have an identity of at least 70% with the nucleic acid sequences described under a), b), e), or f);
i) Nucleic acid molecules, which hybridise with at least one strand of the nucleic acid molecules described under a), b), e), or f) under stringent conditions;
h) Nucleic acid molecules, the nucleotide sequence of which deviates from the sequence of the nucleic acid molecules specified under a), b), e), or f) due to degeneration of the genetic code; and
j) Nucleic acid molecule, which represent fragments, allelic variants, and/or derivatives of the nucleic acid molecules specified under a), b), c), d), e), f), g), h), or i).

Basically, nucleic acid molecules according to the invention, can originate from any plant, preferably they originate from starch-storing plants, preferably from potato, barley, sorghum, barley, wheat, or rice pants, particularly preferably from *Arabidopsis* plants or rice plants, and more particularly preferably from *Oryza sativa*.

Furthermore, the present invention relates to nucleic acid molecules of at least 21, preferably more than 50 and particularly preferably more than 200 nucleotides length, which specifically hybridise with at least one nucleic acid molecule according to the invention. Here, specifically hybridise means that these molecules hybridise with nucleic acid molecules, which code a protein according to the invention, but not with nucleic acid molecules, which code other proteins. In particular, the invention relates to such nucleic acid molecules, which hybridise with transcripts of nucleic acid molecules according to the invention and, as a result, can hinder their translation. Such nucleic acid molecules, which specifically hybridise with the nucleic acid molecules according to the invention, can, for example, be constituents of antisense, RNAi or co-suppression constructs or ribozymes, or can be used as primers for PCR amplification.

Furthermore, the invention relates to recombinant nucleic acid molecules containing a nucleic acid molecule according to the invention.

In conjunction with the present invention, the term "recombinant nucleic acid molecule" is to be understood to mean a nucleic acid molecule, which contains additional sequences in addition to nucleic acid molecules according to the invention, which do not naturally occur in the combination in which they occur in recombinant nucleic acids according to the invention. Here, the abovementioned additional sequences can be any sequences, preferably they are regulatory sequences (promoters, termination signals, enhancers), particularly preferably they are regulatory sequences that are active in plant tissue, and especially particularly preferably they are regulatory sequences that are active in plant tissue, in which storage starch is synthesised. Methods for the creation of recombinant nucleic acid molecules according to the invention are known to the person skilled in the art, and include genetic methods such as bonding nucleic acid molecules by way of ligation, genetic recombination, or new synthesis of nucleic acid molecules, for example (see e.g. Sambrok et al., Molecular Cloning, A Laboratory Manual, 3rd edition (2001) Cold Spring Harbour Laboratory Press, Cold Spring Harbour, N.Y. ISBN: 0879695773, Ausubel et al., Short Protocols in Molecular Biology, John Wiley & Sons; 5th edition (2002), ISBN: 0471250929).

A further embodiment of recombinant nucleic acid molecules of the present invention are vectors, in particular plasmids, cosmids, viruses, bacteriophages, and other customary vectors in gene technology, which contain the nucleic acid molecules according to the invention described above.

In a further embodiment, the nucleic acid molecules according to the invention contained in the vectors are linked with regulatory sequences, which initiate expression in prokaryotic or eukaryotic cells. Here, the term "expression" can mean both transcription and translation. The nucleic acid molecules according to the invention can have an in "sense" orientation and/or an "antisense" orientation with respect to the regulatory sequences.

Regulatory sequences for expression in prokaryotic organisms, e.g. *E. coli*, and in eukaryotic organisms are sufficiently described in literature, in particular such for expression in yeast are described, such as e.g. *Saccharomyces cerevisiae*. An overview of various systems for expression for proteins in various host organisms can be found, for example, in Methods in Enzymology 153 (1987), 383-516 and in Bitter et al. (Methods in Enzymology 153 (1987), 516-544).

A further subject of the present invention is a host cell, particularly a prokaryotic or eukaryotic cell, which is genetically modified with a nucleic acid molecule according to the invention and/or with a vector according to the invention, as well as cells that originate from these types of host cells, and which contain the genetic modification according to the invention.

In a further embodiment, the invention relates to host cells, particularly prokaryotic or eukaryotic cells, which were transformed with a nucleic acid molecule according to the invention or with a vector according to the invention, as well as host cells, which originate from these types of host cells, and which contain the described nucleic acid molecules according to the invention or vectors.

The host cells can be bacteria cells (e.g. *E. coli*, bacteria of the genus *Agrobacterium*, particularly *Agrobacterium tumefaciens* or *Agrobacterium rhizogenes*) or fungal cells (e.g. yeast, particularly *S. cerevisiae*, *Agaricus*, in particular *Agaricus bisporus*, *Aspergillus*, *Trichoderma*), as well as plant or animal cells. Here, the term "transforms" means that the cells according to the invention are genetically modified with a nucleic acid molecule according to the invention, inasmuch as they contain at least one nucleic acid molecule according to the invention in addition to their natural genome. This can occur in the cell freely, possibly as a self-replicating molecule, or it can be stably integrated into the genome of the host cell.

The host cells of microorganisms are preferable. Within the framework of the present patent application, this is understood to include all bacteria and all protists (e.g. fungi, particularly yeasts and algae), as they are defined in Schlegel "General Microbiology" (Georg Thieme Publishing House (1985), 1-2), for example.

Further host cells according to the invention are plant cells. In principle, these can be plant cells from any plant species, i.e. both monocotyledonous and dicotyledonous plants. These are preferably plant cells from agricultural useful plants, i.e. from plants, which are cultivated by humans for nutritional, technical, or particularly industrial purposes. The invention relates preferably to plant cells and plants from starch-storing plants (maize, rice, wheat, rye, oat, barley, cassava, potato, sago, mung bean, pea or sorghum); in particular, plant cells from plants of the (systematic) family Poacea, particularly preferably plant cells from maize or wheat plants.

Compositions containing a nucleic acid molecule according to the invention, recombinant nucleic acid molecule according to the invention or a vector according to the invention are also the subject matter of the present invention. Compositions containing a nucleic acid molecule according to the invention, a recombinant nucleic acid molecule according to the invention, or a vector according to the invention, and a host cell are preferred. Particularly preferably, the host cell is a plant cell, more particularly preferably a cell from maize or wheat plants.

A further aspect of Compositions according to the invention relates to compositions, which can be used for producing host cells according to the invention, preferably for producing plant cells according to the invention. Preferably, this is a composition containing a nucleic acid molecule according to the invention, a recombinant nucleic acid molecule according to the invention, or a vector according to the invention, and a biolistic carrier, which is suitable for the introduction of a nucleic acid molecule according to the invention into a host cell. Preferred biolistic carriers are particles of tungsten, gold or synthetic materials.

A further embodiment of compositions according to the invention relates to compositions containing a nucleic acid molecule according to the invention, a recombinant nucleic acid molecule according to the invention, or a vector according to the invention, and a plant cell and a synthetic cultivation medium. Preferably, such compositions also contain polyethylene glycol (PEG) in addition to nucleic acid molecules according to the invention, plant cells, and a synthetic cultivation medium. In the case of these compositions, the recombinant nucleic acid molecule according to the invention occurs outside of the plant cell, i.e. it is located outside of the cell interior of the plant cell, which is enclosed by a cytoplasmic membrane.

Synthetic culture media, which are suitable for the cultivation and/or transformation of plant cells, are known to the person skilled in the art, and are sufficiently described in literature, for example. Many different synthetic cultivation media are also available for purchase in the specialised trade (e.g. DUCHEFA Biochemie B.V., Belgium).

A further embodiment of compositions according to the invention relates to compositions, which are used for the identification of nucleic acids according to the invention. Preferably, such compositions contain additional nucleic acid molecules, in addition to a nucleic acid molecule according to the invention, a recombinant nucleic acid molecule according to the invention, or a vector according to the invention, particularly nucleic acid molecules of plant origination, which can occur in the form of genomic DNA, mRNA, or as clones in so-called DNA libraries. DNA libraries, which occur as cosmids, phagmids, plasmids, YACs or BACs are preferred. The DNA libraries can contain both genomic DNA and cDNA. The nucleic acid molecules according to the invention, recombinant nucleic acid molecules according to the invention, or a vector according to the invention are used in these compositions, preferably as a hybridisation sample.

A further embodiment of the present invention relates to a protein, which exhibits starch-phosphorylating activity, and which requires phosphorylated starch as a substrate. Preferably, this is a protein, which exhibits phosphorylated starch phosphorylating activity, and which requires phosphorylated starch as a substrate.

A further embodiment of the present invention relates to a protein according to the invention, which requires phosphorylated starch as a substrate, and transfers a residual phosphate of ATP to phosphorylated starch. Preferably, a protein according to the invention transfers the residual beta-phosphate of ATP to phosphorylated starch. Particularly preferably, a protein according to the invention transfers the residual beta-phosphate of the ATP to phosphorylated starch and the residual gamma-phosphate of ATP to water, and therefore possesses the activity of a [phosphorylated-alpha-1,4-glucan]-water-dikinase or a [phosphorylated-starch]-water-dikinase.

A further embodiment of the present invention relates to a protein according to the invention, which accumulates as a phosphorylated intermediate product when transferring residual phosphate to phosphorylated starch.

A further embodiment of the present invention relates to a protein according to the invention, which exhibits increased bonding activity to phosphorylated starch in comparison to non-phosphorylated starch.

A further embodiment of the present invention relates to a protein according to the invention, which introduces more additional phosphate monoester bonds in the C-3 position in comparison to phosphate monoester bonds in the C-6 position of the glucose molecules of a phosphorylated starch.

Preferably, at least 30%, more preferably at least 60%, particularly preferably at least 90%, and most preferably at least 120% more phosphate monoester bonds in the C-3 position of the glucose molecules of a phosphorylated starch are introduced in comparison with the phosphate monoester bonds in the C-6 position of the glucose molecules of a phosphorylated starch.

A further subject of the present invention relates to a protein according to the invention, which exhibits a molecular weight derived from the amino acid sequence of 120 kDa to 145 kDa, preferably from 120 kDa to 140 kDa, particularly preferably from 125 kDa to 140 kDa, and most particularly preferably from 130 kDa to 135 kDa.

A further embodiment of the present invention relates to a protein according to the invention, which exhibits a phosphohistidine domain. The phosphohistidine domain preferably contains two residual histidines.

A further subject of the present invention is proteins according to the invention chosen from the group consisting of
a) Proteins, which include the amino sequence specified under SEQ ID NO 2 or SEQ ID NO 4;
b) Proteins, which are coded by the coding region of the DNA inserted into the plasmid A.t.-OK1-pGEM or pMI50; or
c) Proteins, which exhibit an identity of at least 60% with the amino acid sequence of the proteins specified under a) or b).

In a further embodiment, the present invention relates to proteins with phosphorylated starch phosphorylating activity, wherein the coded protein exhibits an identity of at least 70%, preferably at least 80%, particularly preferably at least 90%, and more particularly preferably at least 95% with the amino acid sequence specified under SEQ ID NO 2 or SEQ ID NO 4, or with the amino acid sequence of an OK1 protein coded by the insertion into plasmid A.t.-OK1-pGEM or plasmid pMI50.

A further embodiment of the present invention relates to a protein according to the invention, characterised in that the amino acid sequence coding the protein exhibits a phosphohistidine domain. Preferably, the protein according to the invention exhibits a phosphohistidine domain, which has an identity of at least 50%, particularly at least 60%, preferably at least 70%, particularly preferably at least 80%, and more particularly preferably at least 90% with the amino acid sequence specified in SEQ ID NO 5.

In a further embodiment, the present invention relates to a protein according to the invention, wherein the protein originates from an *Arabidopsis* or a rice plant.

A further embodiment of the present invention relates to a protein, which exhibits increased bonding activity to phosphorylated starch in comparison with non-phosphorylated starch, wherein the bonding activity to phosphorylated starch is increased by at least three times, preferably at least four times, particularly preferably at least five times, and more particularly preferably at least six times, in comparison to the bonding activity of a non-phosphorylated starch.

In a further embodiment, the invention also relates to proteins, which are coded by nucleic acid molecules according to the invention.

Description of Sequences

SEQ ID NO 1: Nucleic acid sequence comprising the coding region of the A.t.-OK1 proteins from *Arabidopsis thaliana*. This sequence is inserted in the A.t.-OK1-pGEM and OK1-pDEST17 vectors.

SEQ ID NO 2: Amino acid sequence coding the A.t.-OK1 protein from *Arabidopsis thaliana*. This sequence can be derived from the nucleic acid sequence specified under SEQ ID NO 1.

SEQ ID NO 3: Nucleic acid sequence comprising the coding region of the O.s.-OK1 protein from *Oryza sativa*. This sequence is inserted in the pMI50 vector.

SEQ ID NO 4: Amino acid sequence coding the O.s.-OK1 protein from *Oryza sativa*. This sequence can be derived from the nucleic acid sequence specified under SEQ ID NO 3.

SEQ ID NO 5: Peptide sequence coding the phosphohistidine domain of the OK1 proteins from *Arabidopsis thaliana* and *Oryza sativa*.

DESCRIPTION OF FIGURES

FIG. 2 A) shows a denaturing (SDS) acrylamide gel on completion of electrophoresis stained with Coomassie Blue. FIG. 2 B) shows the autoradiography of a denaturing (SDS) acrylamide gel. The same amounts of the same samples were applied to each of the two gels. M: Standard protein molecular weight marker; R1: Sample from reaction vessel 1 according to Example 7 (after incubating an OK1 protein with ATP); R2: Sample from reaction vessel 2 according to Example 7 (after incubating an OK1 protein with ATP the protein was heated to 95° C.); R3: Sample from reaction vessel 3 according to Example 7 (after incubating an OK1 protein with ATP the protein was incubated in 0.5 M HCl); R4: Sample from reaction vessel 4 according to Example 7 (after incubating an OK1 protein with ATP the protein was incubated in 0.5 M NaOH).

FIG. 5 A) shows a Western blot. FIG. 5 B) shows the autoradiography of a denaturing (SDS) acrylamide gel. The same amounts of the same samples were applied to each of the two gels. The OK1 protein was incubated either with randomised radioactively labeled ATP or with ATP specifically radioactively labeled in the gamma position. On completion of incubation, the proteins were either heated to 30° C. or 95° C., or incubated in 0.5 M NaOH or 0.5 M HCl respectively.

FIG. 7 Western Blot analysis of protein extracts from plants using an antibody against the OK1 protein from *Arabidopsis thaliana*. Protein extracts from leaves of the following plants are shown: Ara *Arabidosis thaliana;* 51, 54, 55, 67, 72, 73, 79, 62, 63, 64, 65, 69, 66, 68 are independent lines of the transformation 385JH; D wildtype *Solanum tuberosum* cv Désirée.

GENERAL METHODS

Figure 1:
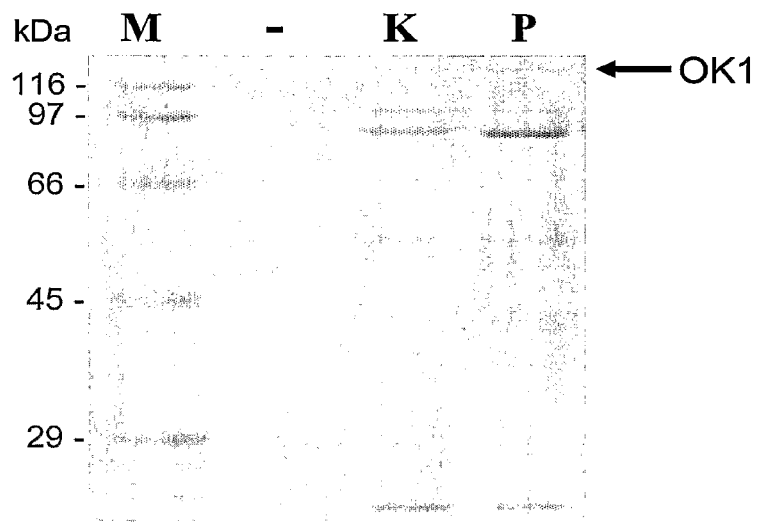
FIG. 1: Denaturing acrylamide gel for identifying proteins from *Arabidopsis thaliana*, which preferably bond to non-phosphorylated starch in comparison with phosphorylated starch. A standard protein molecular weight marker is shown in trace "M". Proteins obtained after incubating control preparation C from Example 1d) are shown in trace "-". Protein extracts of *Arabidopsis thaliana*, obtained after incubation with non-phosphorylated starch, isolated from leaves of an *Arabidopsis thaliana* sex1-3 mutant (Preparation B, example 1d), are shown in trace "K". Protein extracts of *Arabidopsis thaliana*, obtained after incubation with starch, isolated from leaves of an *Arabidopsis thaliana* sex1-3 mutant, which was phosphorylated retrospectively in vitro with an R1 protein (Preparation A, Example 1d), are shown in trace "P". On completion of electrophoresis, the acrylamide gel was stained with Coomassie Blue.

In the following, methods are described, which can be used for carrying out methods described in the invention. These methods constitute specific embodiments of the present invention but do not restrict the present invention to these methods. The person skilled in the art knows that he can implement the invention in the same way by modifying the methods described and/or by replacing individual parts of the methods by alternative parts of the methods.

1. Manufacture of Protein Extracts from Plant Tissue a) Manufacture of Protein Extracts from Plant Tissue Leaf material is frozen in liquid nitrogen immediately after harvesting, and subsequently homogenised in the mortar under liquid nitrogen. The reduced leaf material is mixed with ca. 3.5-times the volume (with respect to the weight of the leaf material used) of cold (4° C.) binding buffer and broken down for 2×10 s with an Ultraturrax (maximum speed). After the first treatment with an Ultraturrax, the reduced leaf material is cooled on ice before the second treatment is carried out. The treated leaf material is then passed through a 100-μm nylon mesh and centrifuged for 20 min (50 ml centrifuge vessel, 20.000×g, 4° C.).

b) Precipitation of the Proteins Contained in the Protein Extracts

The supernatant obtained following centrifugation according to Step a) is removed and its volume determined. To precipitate proteins, ammonium sulphate is added continuously to the supernatant over a period of 30 minutes while stirring on ice down to a final concentration of 75% (weight/volume). The supernatant is subsequently incubated for a further hour on ice while stirring. The proteins precipitated from the supernatant are pelletised at 20.000×g and 4° C. for 10 min and the pellets are, subsequently absorbed in 5 ml of binding buffer, i.e. the proteins present in the pellet are dissolved.

c) Desalting of the Precipitated Proteins

The dissolved proteins are desalted by means of a PD10 column filled with Sephadex G25 (Amersham Bioscience, Freiburg, Prod. No. columns: 17-0851-01, Prod. No. Sephadex G25-M: 17-0033-01) at a temperature of 4° C., i.e. the ammonium sulphate used under Step b) for precipitation is also separated from the dissolved protein. The PD10 column is equilibrated with binding buffer before the proteins dissolved in accordance with Step b) are applied. For this purpose, 5 ml of binding buffer are spread over the column in each case. Subsequently, 2.5 ml of the protein solution obtained in accordance with Step b) are added to each column before proteins are eluted from the column with 3.5 ml binding buffer.

d) Determination of the Protein Concentration

The protein concentration is determined with a Bradford assay (Biorad, Munich, Prod. No. 500-0006 (Bradford, 1976, Anal. Biochem. 72, 248-254)).

e) Composition of the Binding Buffer [

| Binding buffer: | 50 mM | HEPES/NaOH (or KOH), pH 7.2 |
|---|---|---|
| | 1 mM | EDTA |
| | 2 mM | Dithioerythritol (DTE) |
| | 2 mM | Benzamidine |
| | 2 mM | ε-Aminocapronic acid |
| | 0.5 mM | PMSF |
| | 0.02% | Triton X-100 |

2. Isolation of Leaf Starch a) Isolation of Starch Granules from Plant Tissues

Leaf material is frozen immediately after harvesting in liquid nitrogen. The leaf material is homogenised in portions in the mortar under liquid nitrogen and absorbed into a total of ca. 2.5-times the volume (weight/volume) of starch buffer. In addition, this suspension is again homogenised in the Waring blender for 20 s at maximum speed. The homogenate is passed through a nylon mesh (100 μm mesh width) and centrifuged for 5 minutes at 1.000×g. The supernatant with the soluble proteins is discarded.

b) Cleaning the Starch Isolated from the Plant Tissues

After removing the green material lying on top of the starch by rinsing off the green material with starch buffer, the pellet containing the starch obtained from Step a) is absorbed in starch buffer and successively passed through nylon meshes with different mesh widths (in the order of 60 μm, 30 μm, 20 μm). The filtrate is centrifuged using a 10 ml Percoll cushion (95% (v/v) Percoll (Pharmacia, Uppsala, Sweden), 5% (v/v) 0.5M HEPES-KOH pH7.2) (Correx tube, 15 min, 2.000×g). The sediment obtained after this centrifugation is re-suspended once in starch buffer and centrifuged again (5 min, 1.000×g).

c) Removal of the Proteins Bonded to the Starch

Following Step b), starch granules are obtained, which contain proteins bonded to the starch. The proteins bonded to the surface of the starch granules are removed by incubating four times with 0.5% SDS (sodium lauryl sulphate) for 10-15 minutes in each case at room temperature under agitation. Each washing step is followed by a centrifugation (5 min, 5.000×g), in order to separate the starch granules from the respective wash buffer.

d) Purification of Starch that has Been Freed of Proteins

The starch obtained from Step c), which has been freed from the proteins bonded to its surface, is subsequently removed by incubating four times with wash buffer for 10-15 minutes in each case at room temperature under agitation. Each washing step is followed by a centrifugation (5 min, 5.000×g), in order to separate the starch granules from the respective wash buffer. These cleaning steps serve mainly to remove the SDS used in the incubations in Step c).

e) Determination of the Concentration of Isolated Starch

The amount of starch isolated in Step d) is determined photometrically. After suitable dilution, the optical density of the starch suspension is measured against a calibration curve at a wavelength of 600 nm. The linear range of the calibration curve is located between 0 and 0.3 extinction units.

To produce the calibration curves, starch, for example isolated from leaves of an *Arabidopsis thaliana* sex1-3 mutant, is dried under vacuum, weighed and absorbed in a defined volume of water. The suspension so obtained is diluted with water in several steps in a ratio of 1 to 1 in each case until a suspension of ca. 5 μg starch per ml of water is obtained. The suspensions obtained by the individual dilution steps are measured in the photometer at a wavelength of 600 nm. The absorption values obtained for each suspension are plotted against the concentration of starch in the respective suspension. The calibration curve obtained should follow a linear mathematical function in the range from 0 μg starch per ml of water to 0.3 μg starch per ml of water.

f) Storage of Isolated Starch

The starch can either be used directly without further storage for further tests, or stored in aliquots in 1.5 mL Eppendorf vessels at −20° C. Both the frozen starch and the non-stored, freshly isolated starch can be used, if required, for the methods described in the present invention relating to in vitro phosphorylation and/or binding test, for example.

g) Composition of Buffers Used

| 1x starch buffer: | 20 mM | HEPES-KOH, pH 8.0 |
|---|---|---|
| | 0.2 mM | EDTA |
| | 0.5% | Triton X-100 |
| Wash buffer: | 50 mM | HEPES/KOH, pH 7.2 |

3. Recombinant Expression of an Identified Starch-Phosphorylating Protein a) Manufacture of a Bacterial Expression Vector Containing a cDNA, which Codes a Starch-Phosphorylating Protein The cDNA coding a starch-phosphorylating protein can be amplified, for example, using mRNA or poly-A-plus-mRNA from plant tissues as a "template", by means of a polymerase chain reaction (PCR). For this purpose, a reverse transcriptase is first used for the manufacture of a cDNA strand, which is complementary to an mRNA, which codes a starch-phosphorylating protein, before the cDNA strand concerned is amplified by means of DNA polymerase. So-called "kits" containing substances, enzymes and instructions for carrying out PCR reactions are available for purchase (e.g. SuperScript™ One-Step RT-PCR System, Invitrogen, Prod. No.: 10928-034). The amplified cDNA coding a starch-phosphorylating protein can subsequently be cloned in a bacterial expression vector, e.g. pDEST™ (17 (Invitrogen). pDEST™17 contains the T7 promoter, which is used to initiate the transcription of the T7-RNA-polymerase. Furthermore, the expression vector pDEST™17 contains a Shine Dalgarno sequence in the 5'-direction of the T7 promoter followed by a start codon (ATG) and by a so-called His tag. This His tag consists of six codons directly following one another, which each code the amino acid histidine and are located in the reading frame of the said start codon. The cloning of a cDNA coding a starch-phosphorylating protein in pDEST™17 is carried out in such a way that a translational fusion occurs between the codons for the start codon, the His tag and the cDNA coding a starch-phosphorylating protein. As a result of this, following transcription initiated on the T7 promoter, and subsequent translation, a starch-phosphorylating protein is obtained, which contains additional amino acids containing the His tag on its N-terminus.

However, other vectors, which are suitable for expression in microorganisms, can also be used for the expression of a starch-phosphorylating protein. Expression vectors and associated expression strains are known to the person skilled in the art and are also available for purchase from the appropriate dealer in suitable combinations.

b) Manufacture of Expression Clones in *Escherichia coli*

First of all, an appropriate transformation-competent *E. coli* strain, which chromosomally codes a T7-RNA polymerase, is transformed with the expression plasmid manufactured under Step a), and subsequently incubated overnight at 30° C. on culture medium solidified with agar. Suitable expression strains are, for example, BL21 strains (Invitrogen Prod. No.: C6010-03, which chromosomally code a T7-RNA polymerase under the control of an IPTG-inducible promoter (lacZ).

Bacteria colonies resulting from the transformation can be investigated using methods known to the person skilled in the art to see whether they contain the required expression plasmid containing a cDNA coding the starch-phosphorylating protein. At the same time, expression clones are obtained.

c) Expression of a Starch-Phosphorylating Protein in *Escherichia coli*

First, a preparatory culture is prepared. To do this, an expression clone obtained in accordance with Step b) is seeded in 30 ml Terrific Broth (TB medium) containing an antibiotic for selection on the presence of the expression plasmid, and incubated overnight at 30° C. under agitation (250 rpm).

Next, a main culture is prepared for the expression of a starch-phosphorylating protein. To do this, in each case, 1 liter Erlenmeyer flasks, each containing 300 ml of TB medium, pre-heated to 30° C., and an antibiotic for selection on the presence of the expression plasmid are each seeded with 10 ml of an appropriate preparatory culture and incubated at 30° C. under agitation (250 rpm) until an optical density (measured at a wavelength of 600 nm; $OD_{600}$) of ca. 0.8 is achieved.

If, for the expression of a starch-phosphorylating protein, an expression plasmid is used, in which the expression of the starch-phosphorylating protein is initiated by means of an inducible system (e.g. the expression vector pDEST™17 in BL21 *E. coli* strains, inducible by means of IPTG), then on reaching an $OD_{600}$ of ca. 0.8, the inductor concerned (e.g. IPTG) is added to the main culture. After adding the inductor, the main culture is incubated at 30° C. under agitation (250 rpm) until an $OD_{600}$ of ca. 1.8 is achieved. The main culture is then cooled for 30 minutes on ice before the cells of the main culture are separated from the culture medium by centrifugation (10 minutes at 4.000×g and 4° C.).

4. Purification of a Starch-Phosphorylating Protein a) Breaking Down of Cells Expressing a Starch-Phosphorylating Protein The cells obtained in Step c), General Methods, Item 3 are re-suspended in lysis buffer. In doing so, ca. 4 ml lysis buffer are added to about 1 g of cells. The re-suspended cells are then incubated for 30 minutes on ice before they are broken down with the help of an ultrasonic probe (Baudelin Sonoplus UW 2070, Baudelin electronic, Berlin, settings: Cycle 6, 70%, 1 minute) under continuous cooling by means of the ice. Care must be taken here to ensure that the cell suspension is not heated too much during the ultrasonic treatment. The suspension obtained after the ultrasonic treatment is centrifuged (12 minutes at 20.000×g, 4° C.) and the supernatant obtained after centrifugation is filtered using a filter with a pore size of 45 μm.

b) Purification of the Starch-Phosphorylating Protein

If the starch-phosphorylating protein expressed in *E. coli* cells is a fusion protein with a His tag, then cleaning can take place with the help of nickel ions, to which the His tag bonds with greater affinity. To do this, 25 ml of the filtrate obtained in Step d) is mixed with 1 ml Ni-agarose slurry (Qiagen, Prod. No.: 30210) and incubated for 1 hour on ice. The mixture of Ni-agarose slurry and filtrate is subsequently spread over a polystyrene column (Pierce, Prod. No.: 29920). The product, which runs through the column, is discarded. The column is next washed by adding 8 ml of lysis buffer, the product, which runs through the column, again being discarded. Elution of the starch-phosphorylating protein then takes place by fractionated addition to the column of 1 ml E1 buffer twice, followed by 1 ml E2 buffer once and subsequently 1 ml E3 buffer five times. The product, which runs through the column, which is produced by adding the individual fraction of the appropriate elution buffer (E1, E2, E3 buffer) to the column, is collected in separate fractions. Aliquots of these fractions are subsequently analysed by means of denaturing SDS acrylamide gel electrophoresis followed by Coomassie Blue colouring. The fractions, which contain the starch-phosphorylating protein in sufficient quantity and satisfactory purity, are cleaned and concentrated with the help of pressurised filtration at 4° C. Pressurised filtration can be carried out, for example, with the help of an Amicon cell (Amicon Ultrafiltration Cell, Model 8010, Prod. No.: 5121) using a Diaflo PM30 membrane (Millipore, Prod. No.: 13212) at 4° C. Other methods known to the person skilled in the art can also be used for concentration however.

c) Composition of Buffers Used

| Lysis buffer: | 50 mM | HEPES |
|---|---|---|
| | 300 mM | NaCl |
| | 10 mM | Imidazole |
| | pH 8.0 (adjust with NaOH) | |
| | 1 mg/ml | Lysozyme |
| | | (add immediately before using the buffer) |
| ¼ tablet per 10 ml protease inhibitors completely EDTA free, | | |
| (Roche product No.: 1873580, add immediately before using the buffer) | | |
| Elution buffer E1: | 50 mM | HEPES |
| | 300 mM | NaCl |
| | 50 mM | Imidazole |
| | pH 8.0 (adjust with NaOH) | |
| Elution buffer E2: | 50 mM | HEPES |
| | 300 mM | NaCl |
| | 75 mM | Imidazole |
| | pH 8.0 (adjust with NaOH) | |
| Elution buffer E3: | 50 mM | HEPES |
| | 300 mM | NaCl |
| | 250 mM | Imidazole |
| | pH 8.0 (adjust with NaOH) | |

5. Recombinant Expression of an R1Protein

The recombinant expression of an R1 protein is described in the literature (Ritte et al., 2002, PNAS 99, 7166-7171; Mikkelsen et al., 2004, Biochemical Journal 377, 525-532), but can also be carried out in accordance with the methods relating to the recombinant expression of a starch-phosphorylating protein described above under General Methods, Item 3.

6. Purification of an R1Protein

Purification of an R1 protein is described in the literature (Ritte et al., 2002, PNAS 99, 7166-7171; Mikkelsen et al., Mikkelsen et al., 2004, Biochemical Journal 377, 525-532), but can also be carried out in accordance with the methods relating to the cleaning of a starch-phosphorylaying protein described above under General Methods, Item 4 if an R1 fusion protein, which contains a His tag, is produced by expression of R1 in *E. coli* cells.

7. In-Vitro Manufacture of Phosphorylated Starch on the Basis of Non-Phosphorylated Starch a) In Vitro Phosphorylation of Non-Phosphorylated Starch Starch, which does not contain starch phosphate (e.g. isolated from leaves of *Arabidopsis thaliana* sex1-3 mutants with the help of the methods described above under General Methods, Item 2), is mixed with R1 buffer and with purified R1 protein (ca. 0.25 µg R1 protein per mg starch) in order to produce a starch content of 25 mg per ml. This reaction preparation is incubated overnight (approx. 15 hours) at room temperature under agitation. R1 bonded to the starch present in the reaction preparation is removed on completion of the reaction by washing four times with ca. 800 µl 0.5% SDS in each case. Subsequently, the SDS still present in the in vitro phosphorylated starch is removed by washing five times with 1 ml wash buffer in each case. All washing steps take place at room temperature for 10 to 15 minutes under agitation. Each washing step is followed by a centrifugation (2 min, 10.000× g), in order to separate the starch granules from the respective SDS buffer or wash buffer.

b) Composition of Buffers Used

| R1 buffer: | 50 | mM | HEPES/KOH, pH 7.5 |
|---|---|---|---|
| | 1 | mM | EDTA |
| | 6 | mM | $MgCl_2$ |
| | 0.5 | mM | ATP |
| Wash buffer: | 50 | mM | HEPES/KOH, pH 7.2 |

8. Bonding of Proteins to Phosphorylated Starch and Non-Phosphorylated Starch a) Isolation of P-Starch Protein Complexes or Non-Phosphorylated Starch Protein Complexes Ca. 50 mg P-starch or ca. 50 mg non-phosphorylated starch respectively are re-suspended in separate preparations in ca. 800 µl protein extract in each case. The protein concentration of the protein extracts should be ca. 4 mg to 5 mg per ml in each case. incubation is carried out on the P-starch or non-phosphorylated starch with protein extracts for 15 minutes under agitation at 4° C. On completion of the incubation, the reaction preparations are centrifuged out using a Percoll cushion (4 ml) (15 minutes, 3500 rpm, 4° C.). Proteins, which are not bonded to phosphorylated starch or to P-starch, are located in the supernatant after centrifugation, and they can be removed using a Pasteur pipette. The supernatant is discarded. The sedimented pellet containing P-starch and non-phosphorylated starch, including the proteins bonded to the respective starches (P-starch protein complexes or non-phosphorylated starch protein complexes respectively), obtained after centrifugation is washed twice with 1 ml of wash buffer in each case (see above, General Methods under Item 7b) by incubating for 3 minutes at 4° C. in each case under agitation. Every washing step is followed by a centrifugation (5 minutes, 8000 rpm, 4° C. in a table centrifuge, Hettich EBA 12R) in order to separate the P-starch or non-phosphorylated starch respectively from the wash buffer.

b) Dissolving the Proteins Bonded in the P-Starch Protein Complexes or Non-Phosphorylated Starch Protein Complexes Respectively The P-starch protein complexes or non-phosphorylated starch protein complexes obtained according to Step a) are re-suspended in approx. 150 µl SDS test buffer in each case, and incubated for 15 minutes under agitation at room temperature. The P-starch or non-phosphorylated starch respectively is subsequently removed from the dissolved proteins by centrifugation (1 minute, 13,000 rpm, room temperature, Eppendorf table centrifuge). The supernatant obtained after centrifugation is centrifuged again in order to remove all residue of P-starch or non-phosphorylated starch (1 minute, 13,000 rpm, room temperature, Eppendorf table centrifuge), and then it is removed. As a result, dissolved proteins, which bond to the P-starch or non-phosphorylated starch respectively, are obtained.

c) Composition of Buffers Used

| SDS test buffer: | 187.5 mM | Tris/HCl pH 6.8 |
|---|---|---|
| | 6% | SDS |
| | 30% | Glycerine |
| | ~0.015% | Bromphenol blue |
| | 60 mM | Dithioerythritol (DTE, add fresh!) |

Percoll: Percoll is dialysed overnight against a solution consisting of [missing word?] and 25 mM HEPES/KOH, pH 7.0

9. Separation of Proteins that Bond to P-Starch and/or Non-Phosphorylated Starch The dissolved proteins obtained in Step c) under General Methods, Item 8 relating to the bonding of proteins to P-starch or non-phosphorylated starch respectively are incubated for 5 minutes at 95° C. in each case and subsequently separated with the help of denaturing polyacrylamide gel electrophoresis. In doing so, an equal volume is applied to the acrylamide gel in each case for the dissolved proteins obtained by bonding to P-starch and for those obtained by bonding to non-phosphorylated starch. The gel obtained on completion of electrophoresis is stained at least overnight with colloidal Comassie (Roth, Karlsruhe, Roti-Blue Rod. No.: A152.1), and subsequently de-stained in 30% methanol, 5% acetic acid or in 25% methanol.

10. Identification and Isolation of Proteins Bonding to P-Starch and/or Non-Phosphorylated Starch a) Identification of Proteins with Increased Bonding Activity with Respect to P-Starch in Comparison with Non-Phosphorylated Starch Proteins, which, after separation by means of acrylamide gel electrophoresis and subsequent visualisation by colouration (see above, General Methods, Item 9), exhibit an increased signal after bonding to P-starch in comparison with a corresponding signal after bonding to non-phosphorylated starch, have increased bonding activity with respect to P-starch in comparison with non-phosphorylated starch. By this means, it is possible to identify proteins, which have increased bonding activity with respect to P-starch in comparison with non-phosphorylated starch. Proteins, which have increased bonding activity with respect to P-starch in comparison with non-phosphorylated starch, are excised from the acrylamide gel.

Identification of the amino acid sequence of proteins, which have increased bonding activity with respect to P-starch in comparison with non-phosphorylated starch Proteins identified in accordance with Step a) are digested with trypsin and the peptides obtained are analysed by means of MALDI-TOF to determine the masses of the peptides obtained. Trypsin is a sequence-specific protease, i.e. trypsin only splits proteins at a specified position when the proteins concerned contain certain amino acid sequences. Trypsin always splits peptide bonds when the amino acids arginine and lysine follow one another starting from the N-terminus. In this way, it is possible to theoretically determine all peptides that would be produced following the trypsin digestion of an amino acid sequence. From the knowledge of the amino acids coding the theoretically determined peptides, the masses of the peptides, which are obtained after theoretical trypsin digestion, can also be determined. Databases (e.g. NCBInr http://prospector.ucsf.edu/ucsfhtml4.0/msfit.htm; Swissprot http://cbrg.inf.ethz.ch/Server/MassSearch.html), which contain information concerning the masses of peptides after theoretical trypsin digestion, can therefore be compared with the real masses of peptides of unknown proteins obtained with MALDI-TOF-MS. Amino acid sequences, which have the same peptide masses after theoretical and/or real trypsin digestion, are to be looked upon as being identical. The databases concerned contain both peptide masses of proteins, the function of which has already been shown, and also peptide masses of proteins, which up to now only exist hypothetically by derivation from amino acid sequences starting from nucleic acid sequences obtained in sequencing projects. The actual existence and the function of such hypothetical proteins has therefore seldom been shown and, if there is a function at all, then this is usually based only on predictions and not on an actual demonstration of the function.

Bands containing proteins identified in accordance with Step a) are excised from the acrylamide gel; the excised acrylamide piece is reduced and destained by incubating for approximately half an hour at 37° C. in ca. 1 ml 60% 50 mM $NH_4HCO_3$, 40% acetonitrile. The decolourising solution is subsequently removed and the remaining gel dried under vacuum (e.g. Speedvac). After drying, trypsin solution is added to digest the proteins contained in the gel piece concerned. Digestion takes place overnight at 37° C. After digestion, a little acetonitrile is added (until the acrylamide gel is stained white) and the preparation is dried under vacuum (e.g. Speedvac). When drying is complete, just enough 5% formic acid is added to cover the dried constituents and they are incubated for a few minutes at 37° C. The acetonitrile treatment followed by drying is repeated once more. The dried constituents are subsequently absorbed in 0.1% TFA (trifluoroacetic acid, 5 μl to 10 μl) and dripped onto a carrier in ca. 0.5 μl portions. Equal amounts of matrix (ε-cyano-4-hydroxycinnamic acid) are also applied to the carrier. After crystallising out the matrix, the masses of peptides are determined by means of MALDI-TOF-MS-MS (e.g. Burker Reflex™ II, Bruker Daltonic, Bremen). With the masses obtained, databases are searched for amino acid sequences, which give the same masses after theoretical trypsin digestion. In this way, amino acid sequences can be identified, which code proteins, which preferably bond to phosphorylated alpha-1,4-glucans and/or which need P-alpha-1,4-glucans as a substrate.

11. Method for Demonstrating the Starch-Phosphorylating Activity of a Protein a) Incubation of Proteins with P-Starch and/or Non-Phosphorylated Starch In order to demonstrate whether a protein has starch-phosphorylating activity, proteins to be investigated can be incubated with starch and radioactively labeled ATP. To do this, ca. 5 mg of P-starch or ca. 5 mg of non-phosphorylated starch are incubated with the protein to be investigated (0.01 μg to 5.0 μg per mg of starch used) in 500 μl phosphorylation buffer for 10 minutes to 30 minutes at room temperature under agitation. The reaction is subsequently stopped by the addition of SDS up to a concentration of 2% (weight/volume). The starch granules in the respective reaction mixture are centrifuged out (1 minute, 13.000×g), and washed once with 900 μl of a 2% SDS solution and four times each with 900 μl of a 2 mM ATP solution. Every washing step is carried out for 15 minutes at room temperature under agitation. After each washing step, the starch granules are separated from the respective wash buffer by centrifugation (1 min, 13.000×g).

In addition, when carrying out an experiment to demonstrate starch-phosphorylating activity of a protein, further reaction preparations, which do not contain protein or contain inactivated protein, but which are otherwise treated in the same way as the reaction preparations described, should be processed as so-called controls.

b) Determination of the Amount of Phosphate Residues Incorporated in the P-Starch and/or Non-Phosphorylated Starch Due to Enzymatic Activity The starch granules obtained in accordance with Step a) can be investigated for the presence of radioactively labeled phosphate residues. To do this, the respective starch is resuspended in 100 μl of water and mixed with 3 ml of scintillation cocktail in each case (e.g. Ready Safe™, BECKMANN Coulter) and subsequently analysed with the help of a scintillation counter (e.g. LS 6500 Multi-Purpose Scintillation Counter, BECKMANN COULTER™).

c) Identification of Proteins, which Preferably Use P-Starch as a Substrate

If a protein is incubated in separate preparations, once with P-starch and once with non-phosphorylated starch, in accordance with the method described under a), then, by comparing the values for the presence of starch phosphate obtained according to Step b), it can be determined whether the protein concerned has incorporated more phosphate in P-starch in comparison with non-phosphorylated starch. In this way, proteins can also be identified, which can introduce phosphate into P-starch but not into non-phosphorylated starch. That means proteins can be identified, which require already phosphorylated starch as a substrate for an additional phosphorylation reaction.

d) Composition of Buffers Used

| Phosphorylation buffer: | 50 mM | HEPES/KOH, pH 7.5 |
|---|---|---|
| | 1 mM | EDTA |
| | 6 mM | MgCl$_2$ |
| | 0.01 to 0.5 mM | ATP |
| | 0.2 to 2 µCi per ml | randomised $^{33}$P-ATP (alternatively, ATP, which contains a phosphate residue, which is specifically labeled in the beta position, can also be used) |

In conjunction with the present invention, the term "randomised ATP" is to be understood to mean ATP, which contains labeled phosphate residues both in the gamma position and in the beta position (Ritte et al. 2002, PNAS 99, 7166-7171). Randomised ATP is also described in the scientific literature as beta/gamma ATP. A method for manufacturing randomised ATP is described in the following.

i) Manufacture of Randomised ATP

The method described here for manufacturing randomised ATP with the help of enzyme-catalysed reactions is based on the following reaction mechanisms:

1st Reaction step:

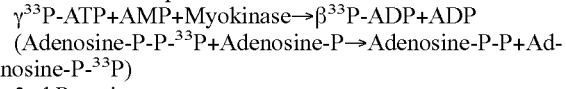
$\gamma^{33}$P-ATP+AMP+Myokinase→$\beta^{33}$P-ADP+ADP (Adenosine-P-P-$^{33}$P+Adenosine-P→Adenosine-P-P+Adenosine-P-$^{33}$P)

2nd Reaction step:

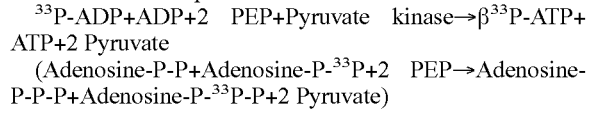
$^{33}$P-ADP+ADP+2 PEP+Pyruvate kinase→$\beta^{33}$P-ATP+ATP+2 Pyruvate (Adenosine-P-P+Adenosine-P-$^{33}$P+2 PEP→Adenosine-P-P-P+Adenosine-P-$^{33}$P-P+2 Pyruvate)

The reaction equilibriums lie on the product side but, in spite of this, this reaction produces a mixture consisting mainly of $\beta^{33}$P-ATP and some $\gamma^{33}$P-ATP.

ii) Performing the First Reaction Step

ATP (100 µCi, 3000 Ci per mmol), which contains a phosphate residue labeled with $^{33}$P in the gamma position (Hartmann Analytic, 10 µCi/µl), is incubated with 2 µl myokinase (AMP-phosphotransferase, from rabbit muscle; SIGMA, Prod. No.: M3003 3.8 mg/ml, 1,626 units/mg) in 90 µl randomising buffer for 1 hour at 37° C. The reaction is subsequently stopped by incubating for 12 minutes at 95° C. before the reaction preparation is cleaned up by means of centrifugal filtration using a Microcon YM 10 filter (Amicon, Millipore Prod. No. 42407) at 14.000×g for at least 10 minutes.

iii) Performing the Second Reaction Step

2 µl pyruvate kinase (see below for how to manufacture an appropriate solution) and 3 µl 50 mM PEP (phosphoenolpyruvate) are added to the filtrate obtained in Step ii). This reaction mixture is incubated for 45 minutes at 30° C. before the reaction is stopped by incubating at 95° C. for 12 minutes. The reaction mixture is subsequently centrifuged (2 minutes, 12,000 rpm in an Eppendorf table centrifuge). The supernatant containing randomised ATP obtained after centrifugation is removed, aliquoted and can be stored at −20° C.

Producing the Pyruvate Kinase Solution

15 µl pyruvate kinase (from rabbit muscle, Roche, Prod. No. 12815), 10 mg/ml, 200 units/mg at 25° C.) are centrifuged out, the supernatant is discarded and the pellet is absorbed in 27 µl pyruvate kinase buffer.

iv) Buffers Used

| Pyruvate kinase buffer: | 50 mM | HEPES/KOH pH 7.5 |
|---|---|---|
| | 1 mM | EDTA |
| Randomising buffer: | 100 mM | HEPES/KOH pH 7.5 |
| | 1 mM | EDTA |
| | 10% | Glycerol |
| | 5 mM | MgCl$_2$ |
| | 5 mM | KCl |
| | 0.1 mM | ATP |
| | 0.3 mM | AMP |

12. Demonstrating the Autophosphorylation of a Protein

In order to demonstrate whether a protein has auto-phosphorylating activity, proteins to be investigated can be incubated with radioactively labeled ATP. To do this, proteins to be investigated (50 µg to 100 µg) are incubated in 220 µl phosphorylation buffer (see above, Item 12 d), General Methods) for 30 minutes to 90 minutes at room temperature under agitation. The reaction is subsequently stopped by the addition of EDTA up to a final concentration of 0.11 M. Ca. 2 µg to 4 µg of protein are separated with the help of denaturing polyacrylamide gel electrophoresis (7.5% acrylamide gel). The gel obtained after polyacrylamide gel electrophoresis is subjected to autoradiography. Proteins, which exhibit a signal in the autoradiography, carry a radioactive phosphate residue.

13. Identification of the C-Atom Positions of the Glucose Molecules of an Alpha-1,4-Glucan, in which Residual Phosphates are Introduced Through a Starch-Phosphorylating Protein Which C-atom positions of the glucose molecules of an alpha-1,4-glucan are phosphorylated by a protein can be demonstrated by hydrolysis of the phosphorylated glucan obtained by means of an appropriate protein in vitro, subsequent separation of the glucose monomers obtained after hydrolysis, followed by measurement of the phosphate incorporated by an appropriate protein in certain fractions of the glucose molecules.

a) Total Hydrolysis of the Alpha-1,4-Glucans

Water suspensions containing alpha-1,4-glucan are centrifuged, the sedimented pellet subsequently re-suspended in 0.7 M HCl (Baker, for analysis) and incubated for 2 hours at 95° C. under agitation. On completion of incubation, the samples are briefly cooled and centrifuged (e.g. 2 minutes 10.000×g). The supernatant obtained is transferred to a new reaction vessel and neutralised by the addition of 2 M NaOH (Baker, for analysis). If a pellet remains, it is re-suspended in 100 µl of water and the quantity of labeled phosphate present therein is determined as a control. The neutralised supernatant is subsequently centrifuged over a 10-kDa filter. By measuring an aliquot of the filtrate obtained, the quantity of labeled phosphate in the filtrate is determined with the help of a scintillation counter, for example.

b) Fractionation of the Hydrolysis Products and Determination of the Phosphorylated C-Atom Positions The neutralised filtrates of the hydrolysis products obtained by means of Step a) can be separated (when using radioactively labeled ATP about 3000 cpm) with the help of high-pressure anion exchange chromatography (HPAE), for example. The neutralised filtrate can be diluted with H$_2$O to obtain the volume required for HPAE. In addition, glucose-6-phosphate (ca. 0.15 mM) and glucose-3-phosphate (ca. 0.3 mM) are added to the appropriate filtrates in each case as an internal control. Separation by means of HPAE can be carried out, for example, with the help of a Dionex DX 600 Bio Lc system using a CarboPac PA 100 column (with appropriate pre-column) and a pulsed amperometric detector (ED 50). In doing so, before injecting the sample, the column is first rinsed for 10 minutes with 99% eluent C and 1% eluent D. A sample volume of 60 µl is then injected. The elution of the sample takes place under the following conditions:

| Flow rate: | 1 ml per minute | | |
|---|---|---|---|
| Gradient: | linearly increasing from 0 minutes to 30 minutes | | |
| | | Eluent C | Eluent D |
| | 0 minutes | 99% | 1% |
| | 30 minutes | 0% | 100% |
| | 35 minutes | 0% | 100% |
| | Run terminated | | |

The hydrolysis products eluted from the column are collected in individual fractions of 1 ml each. As, in each case, non-labeled glucose-3-phosphate (Ritte et al. 2002, PNAS 99, 7166-7171) and non-labeled glucose-6-phosphate (Sigma, Prod. No.: G7879) have been added to the injected samples of hydrolysis products as internal standards, the fractions, which contain either glucose-3-phosphate or glucose-6-phosphate, can be determined by means of pulsed amperometric detection. By measuring the amount of labeled phosphates in the individual fractions and subsequently comparing with the fractions, which contain glucose-3-phosphate or glucose-6-phosphate, this can be used to determine those fractions, in which labeled glucose-6-phosphate or labeled glucose-3-phosphate is contained. The amount of labeled phosphate in the fraction concerned is determined. From the ratios of the amounts of glucose-3-phosphate to glucose-6-phosphate measured for labeled phosphate in the individual hydrolysis products, it can now be determined which C-atom position is preferably phosphorylated by an alpha-1,4-glucan phosphorylating enzyme.

c) Buffers Used:

| Eluent C: | 100 mM | NaOH |
|---|---|---|
| Eluent D: | 100 mM | NaOH |
| | 500 mM | sodium acetate |

14. Transformation of Rice Plants

Rice plants were transformed according to the method described by Hiei et al. (1994, Plant Journal 6(2), 271-282).

15. Transformation of Potato Plants

Potato plants were transferred with the help of *agrobacterium*, as described by Rocha-Sosa et al. (EMBO J. 8, (1989), 23-29).

16. Transformation of Wheat Plants

Wheat plants were transformed according to the method described by Becker et al. (1994, Plant Journal 5, 299-307).

17. Transformation of Maize Plants

Immature embryos of maize plants of line A188 were transformed according to the method described by Ishida et al. (1996, Nature Biotechnology 14, 745-750).

18. Determination of Starch Phosphate Content

Determination of the C-6 Phosphate Content

In the starch, the C2, C3, and C6 positions of the glucose units can be phosphorylated. For determination of the C6-P content of the starch, 50 mg of starch are hydrolysed in 500 µl 0.7 M HCl 4 h at 95° C. Subsequently, the preparations are centrifuged for 10 minutes at 15500 g, and the supernatant is removed. 7 µl of supernatant is mixed with 193 µl imidazole buffer (100 mM imidazole, pH 7.4; 5 mM MgCl$_2$, 1 mM EDTA, and 0.4 mM NAD). The measurement was taken in the photometer at 340 nm. After establishing a base absorption, the enzyme reaction is started by adding two units of glucose-6-phosphate dehydrogenase (of Leuconostoc mesenteroides, Boehringer Mannheim). The change in absorption is directly proportional to the concentration of the G-6-P content in the starch.

b) Determination of the Total Phosphate Content

The determination of the total phosphate content occurs according to the Ames method (Methods in Enzymology VIII, (1966), 115-118).

Approximately 50 mg starch is mixed with 30 µl of ethanolic magnesium nitrate solution, and incinerated for three hours at 500° C. in the muffle oven. The residue is mixed with 300 µl 0.5 M hydrochloric acid, and incubated for 30 minutes at 60° C. Subsequently, an aliquot is filled to 300 µl with 0.5 M hydrochloric acid, poured into a mixture of 100 µl 10% ascorbic acid and 600 µl 0.42% ammonium molybdate in 2 M sulphuric acid, and incubated for 20 minutes at 45° C.

c) Determination of the Content of C-6 Phosphate and C-3 Phosphate

For the determination of the phosphate content, which is bonded in the C-6 position and the C-3 position of the glucose molecules of an alpha-1,4-glucan, the respective glucans can be separated using total hydrolysis according to the HPAE methods listed under General Methods 13. The quantities of glucose-6-phosphate and glucose-3-phosphate can be determined through integration of the individual peak areas obtained after HPEA separation. By comparing the peak surfaces obtained for glucose-6-phosphate in unknown samples with peak surfaces that were obtained after HPEA separation, having known quantities of glucose-6-phosphate and glucose-3-phosphate, the quantity of glucose-6-phosphate and glucose-3-phosphate can be determined in the samples to be examined.

EXAMPLES

1. Isolation of a Protein from *Arabidopsis thaliana*, which Exhibits Increased Bonding Activity to P-Starch in Comparison to Non-Phosphorylated Starch a) Manufacture of Protein Extracts from *Arabidopsis thaliana*

Protein extracts were produced from approximately 7 g of leaves (fresh weight) of *Arabidopsis thaliana* (Okotyp Columbia, Col-O) according to General Methods, Item 1.

b) Isolation of Starch Granules from Leaves of Sex1-3 Mutants of *Arabidopsis thaliana*

Starch granules were isolated from about 20 g (fresh weight) of leaves of a sex1-3 mutant of *Arabidopsis thaliana* according to the method described under General Methods, Item 2.

c) In Vitro Phosphorylation of Starch, Isolated from a Sex1-3 Mutant of *Arabidopsis thaliana* with Purified R1 Protein Approximately 30 mg of non-phosphorylated starch, isolated from a sex1-3 mutant of *Arabidopsis thaliana*, was phosphorylated by way of an R1 protein recombinantly expressed and purified in *E. coli* according to the method described under General Methods, Item 7. For the expression of the R1 protein in *E. coli* and for subsequent purification, the method described by Ritte et al. (2002, PNAS 99, 7166-7171) was used.

d) Isolation of Proteins, which Bond to P-Starch and/or Non-Phosphorylated Starch Protein extracts of *Arabidopsis thaliana*, obtained in accordance with Step a), were incubated and washed in a Preparation A with 50 mg of the in vitro phosphorylated starch manufactured in accordance with Step c) using the method described under General Methods, Item 8a.

In a second Preparation B, protein extracts of *Arabidopsis thaliana*, obtained in accordance with Step a), were incubated and washed with 50 mg of the non-phosphorylated starch manufactured in accordance with Step b) using the method described under General Methods, Item 8a.

Subsequently, the proteins bonded to the P-starch of Preparation A and to the non-phosphorylated starch of Preparation B were dissolved in accordance with the method described under General Methods, Item 8b.

In a third Preparation C, 50 mg of the in vitro phosphorylated starch manufactured in accordance with Step c) were incubated and washed using the method described under General Methods, Item 8a. Preparation C contained no protein extracts however.

e) Separation of the Proteins Obtained in Accordance with Step D) by Means of Acrylamide Gel Electrophoresis The proteins of Preparations A, B and C obtained in Step d) were separated by means of a 9% acrylamide gel under denaturing conditions (SDS) using the method described under General Methods, Item 9, and subsequently stained with Coomassie Blue. The stained gel is shown in FIG. 1. It can be clearly seen that a protein, which has a molecular weight of ca. 130 kDa in denaturing acrylamide gel with regard to a protein standard marker (Trace M), preferably bonds to phosphorylated starch (Trace P) in comparison with non-phosphorylated starch (K).

f) Identification of the Protein, which Preferably Bonds to P-Starch in Comparison with Non-Phosphorylated Starch The band of the protein with a molecular weight of ca. 130 kDa identified in Step e) was excised from the gel. The protein was subsequently released from the acrylamide as described under General Methods, Item 10b, digested with trypsin and the peptide masses obtained were determined by means of MALD-TOF-MS. The so-called "fingerprint" obtained by MALDI-TOF-MS was compared with fingerprints of theoretically digested amino acid molecules in databases (Mascot: http://www.matrixscience.com/search_form_select.html; ProFound: http://129.85.19.192/profound_bin/WebProFound.exe; PepSea: http://195.41.108.38/PepSeaIntro.html). As such a fingerprint is very specific to a protein, it was possible to identify an amino acid molecule. With the help of the sequence of this amino acid molecule, it was possible to isolate a nucleic acid sequence from *Arabidopsis thaliana* coding an OK1 protein. The protein identified with this, method was designated as A.t.-OK1. Analysis of the amino acid sequence of the OK1 protein from *Arabidopsis thaliana* showed that this deviated from the sequence that was present in the database (NP 198009, NCBI). The amino acid sequence shown in SEQ ID No 2 codes the A.t.-OK1 protein. SEQ ID No 2 contains deviations when compared with the sequence in the database (Acc.: NP 198009.1, NCBI). The amino acids 519 to 523 (WRLCE) and 762 to 766 (VRARQ) contained in SEQ ID No 2 are not in the sequence, which is present in the database (ACC.: NP 198009.1). Compared with Version 2 of the database sequence (Acc.: NP 198009.2), the amino acid sequence shown in SEQ ID NO 2 also contains the additional amino acids 519 to 523 (WRLCE).

2. Cloning a cDNA, which Codes the Identified OK1 Protein

The A.t.-OK1 cDNA was isolated with the help of reverse PCR using mRNA isolated from leaves of *Arabidopsis thaliana*. To do this, a cDNA Strand was synthesised by means of reverse transcriptase (SuperScript™ First-Strand Synthesis System for RT PCR, Invitrogen Prod. No.: 11904-018), which was then amplified using DNA polymerase (Expand High Fidelity PCR Systems, Roche Prod. No.: 1732641). The amplified product obtained from this PCR reaction was cloned in the vector pGEM®-T (Invitrogen Prod. No.: A3600). The plasmid obtained is designated A.t.-OK1-pGEM, the cDNA sequence coding the A.t.-OK1 protein was determined and is shown under SEQ ID NO. 1.

The sequence shown under SEQ ID NO 1 is not the same as the sequence, which is contained in the database. This has already been discussed for the amino acid sequence coding an A.t.-OK1 protein.

Conditions used for the amplification of the cDNA coding the A.t.-OK1 protein First strand synthesis:

The conditions and buffer specified by the manufacturer were used. In addition, the reaction preparation for the first strand synthesis contained the following substances:

| | | |
|---|---|---|
| 3 µg | Total RNA | |
| 5 µM | 3'-Primer | (OK1rev1: 5'-GACTCAACCACATAACA CACAAAGATC) |
| 0.83 µM | dNTP Mix | |

The reaction preparation was incubated for 5 minutes at 75° C. and subsequently cooled to room temperature.

The 1$^{st}$ strand buffer, RNase inhibitor, and DTT were then added and incubated for 2 minutes at 42° C. before 1 µL Superscript RT DNA polymerase was added and the reaction preparation was incubated for 50 minutes at 42° C.

Conditions for the amplification of the first strand by means of PCR:

| | | |
|---|---|---|
| 1 µL | of the reaction preparation of the first strand synthesis | |
| 0.25 µM | 3'Primer | (OK1rev2: 5'-TGGTAACGAGGCAAATGC AGA) |
| 0.25 µM | 5'Primer | (OK1fwd2: 5'-ATCTCTTATCACACCACC TCCAATG) |

Reaction conditions:

| Step 1 | 95° C. | 2 min | |
|---|---|---|---|
| Step 2 | 94° C. | 20 sec | |
| Step 3 | 62° C. | 30 sec | (Temp. per cycle-0.67° C.) (30 s), 68° C. ( |
| Step 4 | 68° C. | 4 minutes | |
| Step 5 | 94° C. | 20 sec | |
| Step 6 | 56° C. | 30 sec | |
| Step 7 | 68° C. | 4 minutes | |
| Step 8 | 68° C. | 10 minutes | |

The reaction was first carried out in accordance with Steps 1 to 4. 10 repeats (cycles) were carried out between Step 4 and Step 2, the temperature of Step 3 being reduced by 0.67° C. after each cycle. This was subsequently followed by the reaction in accordance with the conditions specified in Steps 5 to 8. 25 repeats (cycles) were carried out between Step 7 and Step 5, the time of Step 7 being increased by 5 sec on each cycle. On completion of the reaction, the reaction was cooled to 4° C.

3. Creation of a Vector for Recombinant Expression of the cDNA of the OK1 Protein Following amplification by means of PCR by using the plasmid A.t.-OK1-pGEM as a template using Gateway Technology (Invitrogen), the sequence coding the OK1 protein from *Arabidopsis thaliana* was next cloned in the vector pDONOR™ 201 (Invitrogen Prod. No.: 11798-014). pDONOR™ 201. Subsequently, the coding region of the OK1 protein from the vector obtained was cloned by sequence-specific recombination in the expression vector pDEST17™ (Invitrogen Prod. No.: 11803-014). The expression vector obtained was designated as A.t.-OK1-pDEST™17. The cloning resulted in a translational fusion of the cDNA coding the A.t-OK1 protein with the nucleotides present in the expression vector pDEST™17. The nucleotides originating from the vector pDEST™17, which are translationally fused with the cDNA coding the A.t.-OK1 protein, code 21 amino acids. These 21 amino acids include, amongst others, the start codon (ATG) and a so-called His tag (6 histidine residues directly after one another). After translation of these translationally fused sequences, this results in an A.t.-OK1 protein, which has the additional 21 amino acids coded by nucleotides originating from the vector at its N-terminus. The recombinant A.t.-OK1 protein resulting from this vector therefore contains 21 additional amino acids originating from the vector pDEST™17 at its N-terminus.

4. Heterologous Expression of the OK1 Protein in *E. coli*

The expression vector A.t.-OK1-pDEST™17 obtained in accordance with Example 3 was transformed in the *E. coli* strain BL21 Star™ (DE3) (Invitrogen, Prod. No. C6010-03). A description of this expression system has already been given above (see General Methods, Item 3). Bacteria clones, containing the vector A.t.-OK1-pDEST™17, resulting from the transformation were next used to manufacture a preparatory culture, which was subsequently used for inoculating a main culture (see General Methods, Item 3c). The preliminary culture and the main culture were each incubated at 30° C. under agitation (250 rpm). When the main culture had reached an $OD_{600}$ of ca. 0.8, the expression of the recombinant A.t.-OK1 protein was induced by the addition of IPTG (isopropyl-beta-D-thiogalactopyranoside) until a final concentration of 1 mM was achieved. After the addition of IPTG, the main culture was incubated at 30° C. under agitation (250 rpm) until an $OD_{600}$ of ca. 1.8 was achieved. The main culture was then cooled for 30 minutes on ice before the cells of the main culture were separated from the culture medium by centrifugation (10 minutes at 4.000×g and 4° C.).

5. Purification of the Recombinantly Expressed OK1 Protein

The purification and concentration of the A.t.-OK1 protein from cells obtained in accordance with Example 4 was carried out using the method described under General Methods, Item 4.

6. Demonstration of Starch-Phosphorylating Activity of the OK1 Protein

The starch-phosphorylating activity of the A.t.-OK1 protein was demonstrated in accordance with the method described under General Methods, Item 11. In doing so, 5 µg of cleaned A.t.-OK1 Protein manufactured in accordance with Example 5 was in each case incubated in a Preparation A with 5 mg of starch isolated from a sex1-3 mutant of *Arabidopsis thaliana* in accordance with Example 1b) and in a Preparation B with 5 mg of starch obtained by enzymatic phosphorylation in accordance with Example 1c), in each case in 500 µl of phosphorylation buffer containing 0.05 mM radioactively ($^{33}$P) labeled, randomised ATP (in total 1,130, 00 cpm, ca. 0.55 µCi) for 30 minutes at room temperature under agitation. A Preparation C was used as a control, which was the same as Preparation B, except that it contained no OK1 protein, but was otherwise treated in the same way as Preparations A and B. Two tests, which were independent from one another, were carried out for all preparations (A, B, C).

Figure 3:
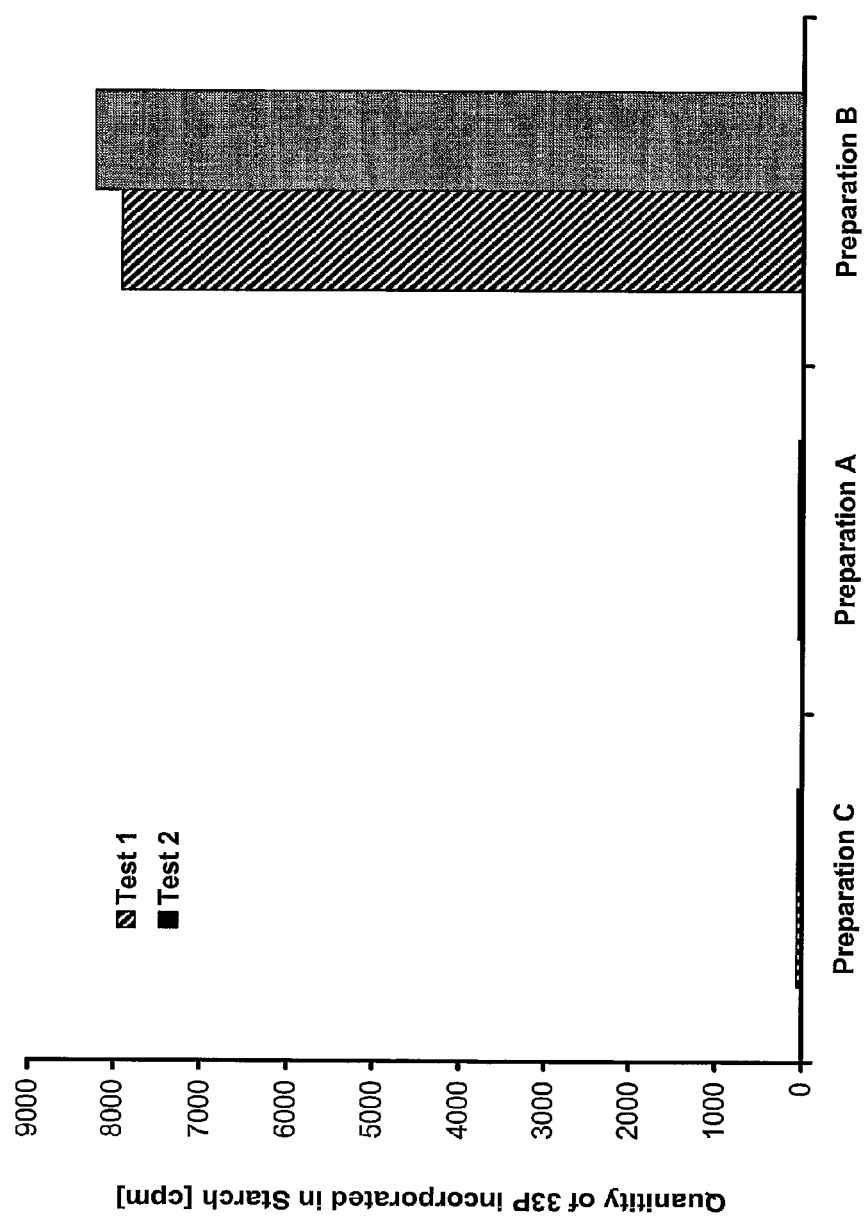
FIG. 3: Demonstration of the starch-phosphorylating activity of an OK1 protein (see Example 6). OK1 protein was incubated with non-phosphorylated starch isolated from leaves of an *Arabidopsis thaliana* sex1-3 mutant (Preparation A) and starch isolated from leaves of an *Arabidopsis thaliana* sex1-3 mutant, which was phosphorylated retrospectively in vitro with an R1 protein (Preparation B). Preparation C is the Same as Preparation B, Except that this Preparation C was incubated without OK1 protein. Two independent tests were carried out for each preparation (A, B, C) (Test 1 and Test 2). The respective amounts are shown graphically, measured in cpm (counts per minute), on $^{33}$P labeled phosphate, which were introduced into non-phosphorylated starch (Preparation A) and phosphorylated starch (Preparation B) by the OK1 protein
Figure 4:
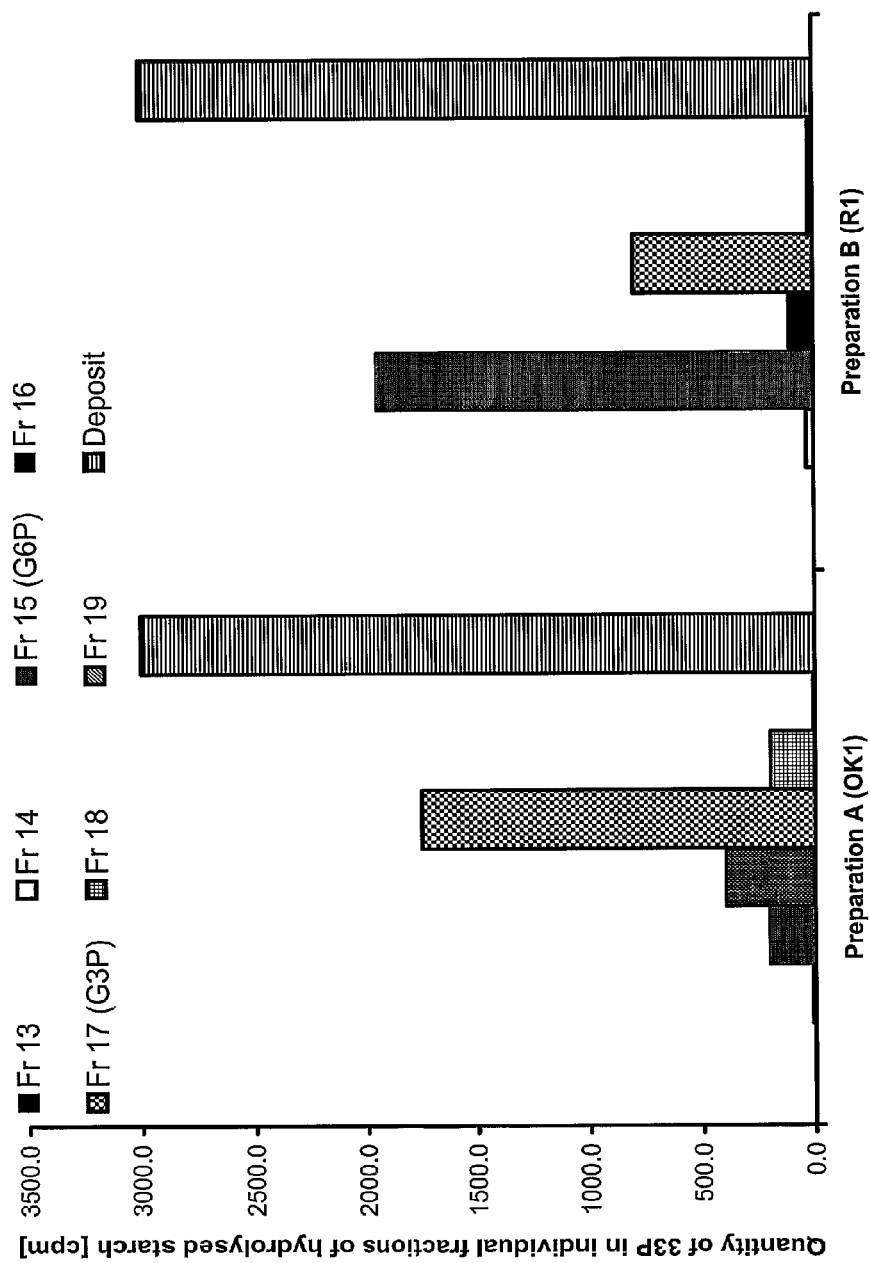
FIG. 4: Comparison of the C-atom positions of glucose molecules of the starch, which was phosphorylated from an R1 protein and an OK1 protein respectively (see Example 9). OK1 protein (Preparation A) was incubated in the presence of ATP labeled with $^{33}$P with starch isolated from leaves of an *Arabidopsis thaliana* sex1-3 mutant, which was phosphorylated retrospectively in vitro with an R1 protein. R1 protein (Preparation B) was incubated in the presence of ATP labeled with $^{33}$P with starch isolated from leaves of an *Arabidopsis thaliana* sex1-3 mutant. On completion of incubation, a total hydrolysis of the starch was carried out and the hydrolysis products were separated by means of HPAE chromatography. As standard, glucose-6-phosphate and glucose-3-phosphate were added to the hydrolysis products before separation. The hydrolysis products separated by means of HPAE chromatography were collected in individual fractions. The added glucose-6-phosphate eluted with fraction 15 and the added glucose-3-phosphate with fraction 17. The fractions obtained were subsequently investigated for the presence of radioactively labeled phosphate. The amount of $^{33}$P labeled phosphate measured in the individual fractions, measured in cpm (counts per minute), which was introduced into the hydrolysis products of the phosphorylated starch by the OK1 protein or the R1 protein, is shown graphically.

Using a scintillation counter, the starches from Preparations A, B, and C were investigated for the presence of radioactively labeled phosphate (see General Methods, Item 11b). The results are shown in Table 1 and in FIG. 3.

TABLE 1

Demonstration of starch-phosphorylating activity of the OK1 protein

| | Measured radioactivity [cpm] | |
|---|---|---|
| | Trial 1 | Trial 2 |
| Preparation A (non-phosphorylated starch + OK1) | 42 | 47 |
| Preparation B (phosphorylated starch + OK1) | 7921 | 8226 |
| Preparation C (phosphorylated starch without protein) | 56 | 53 |

From the results obtained, it can be seen that the OK1 protein does not transfer phosphate groups from ATP to starch when non-phosphorylated starch is provided as a substrate, as the proportion of phosphate groups transferred to non-phosphorylated starch by means of an OK1 protein, measured in cpm, does not exceed the proportion of radioactively labeled phosphate groups in Preparation C (control). If, on the other hand, P-starch is provided as a substrate, the proportion of radioactive phosphate groups, measured in cpm, which are transferred from ATP to P-starch, is significantly higher. From this, it can be seen that the OK1 protein requires P-starch as a substrate and that non-phosphorylated starch is not accepted as a substrate by the OK1 protein.

Figure 6:
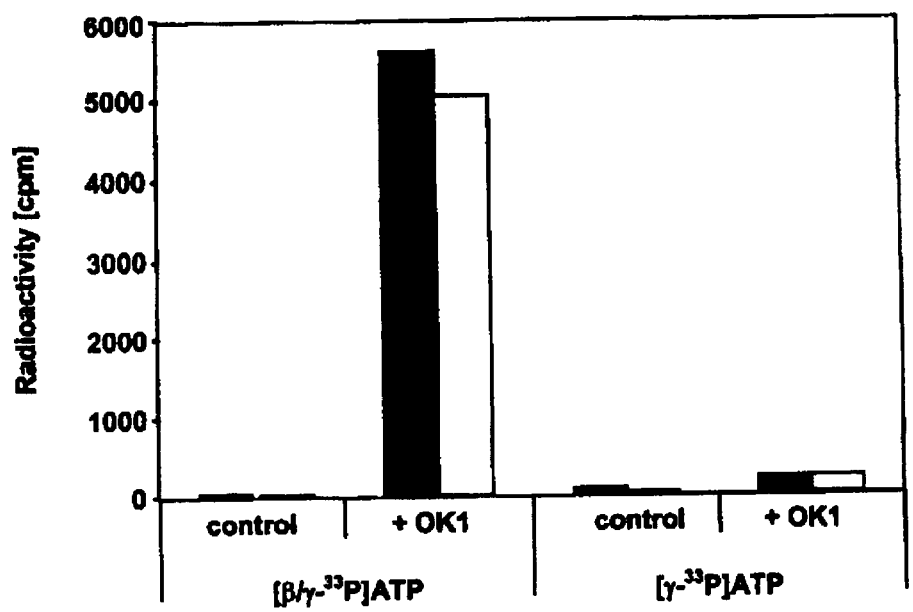
FIG. 6 Demonstration of the transfer of the beta-phosphate residue of ATP to starch in a reaction catalysed by an OK1 protein. Either ATP specifically labeled with $^{33}$P in the gamma position or randomised $^{33}$P ATP was used to phosphorylate starch, which had been phosphorylated in vitro by means of an R1 protein and isolated from leaves of an *Arabidopsis thaliana* sex1-3 mutant, by means of an OK1 protein. No OK1 protein was added in any of the experiments designated as "control". Each preparation was tested twice, independently from one another. The results of both tests are shown.

If the test described above is carried out with ATP specifically labeled in the gamma position with $^{33}$P, then it is not possible to establish an incorporation of radioactively labeled phosphate in the starch. From this, it can be seen that the beta phosphate residue of ATP is transferred from an OK1 protein to starch. The results of such a test are shown in FIG. 6.

7. Demonstration of Autophosphorylation

Autophosphorylation of the A.t.-OK1 protein was demonstrated by means of the methods described above (see General Methods, Item 12). Here, 50 µg of purified A.t.-OK1 protein were incubated with radioactively labeled, randomised ATP in 220 µl of phosphorylation buffer (see above, General Methods, Item 12d) at room temperature for 60 minutes under agitation. Subsequently, 100 µl in each case were removed from the incubation preparations and transferred to four fresh reaction vessels. In reaction vessel 1, the reaction was stopped by the addition of 40 µl 0.11 M EDTA. Reaction vessel 2 was incubated at 95° C. for 5 minutes. HCl was added to reaction vessel 3 up to a final concentration of 0.5 M, and NaOH was added to reaction vessel 4 up to a final concentration of 0.5 M. Reaction vessels 3 and 4 were each incubated for 25 minutes at 30° C. Subsequently, 50 µl in each case were removed from reaction vessels 1, 2, 3 and 4, mixed with SDS test buffer and separated by means of SDS acrylamide gel electrophoresis (7.5% acrylamide gel). For this purpose, samples from the reaction vessels were applied to each of two identical acrylamide gels. One of the gels obtained on completion of electrophoresis was subjected to autoradiography, while the second gel was stained with Coomassie Blue.

Figure 2:
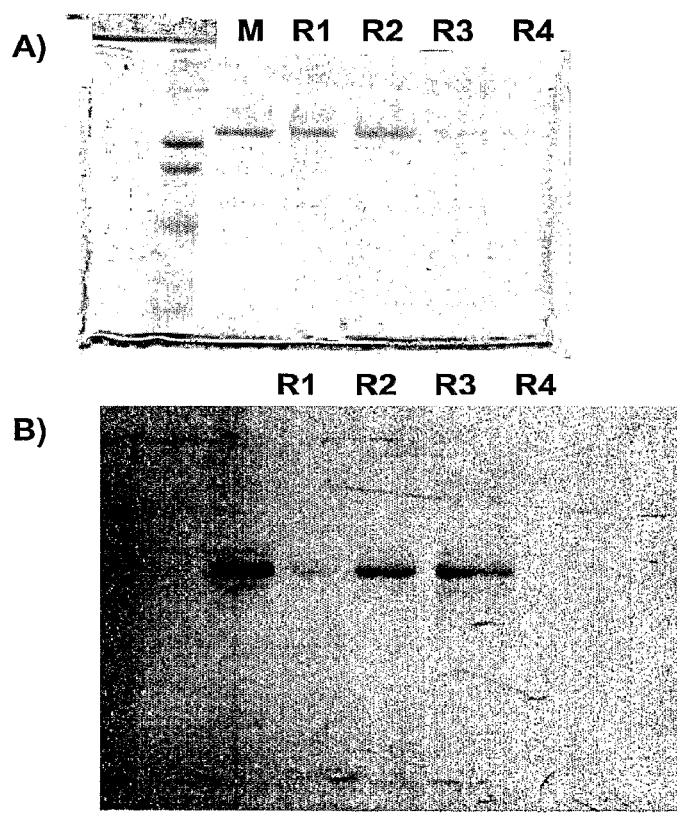
FIG. 2: Demonstration of autophosphorylation of the OK1 protein.

In the gel stained with Coomassie Blue (see FIG. 2A), it can be clearly seen that treatment with 0.5 M NaOH leads to a degradation of OK1 protein. The OK1 protein must therefore be described as unstable compared with NaOH. Incubations at 30° C., 95° C. and with 0.5 M HCl show that the OK1 protein is relatively stable under the stated incubation conditions. This can be concluded from the fact that, under these incubation conditions, in each case approximately the same amounts of OK1 protein can be demonstrated in the gel concerned after colouring with Coomassie Blue.

In the autoradiography (see FIG. 2B), it can be seen by comparison with the phosphorylated OK1 protein incubated at 30° C. that an incubation of the phosphorylated OK1 protein at 95° C. leads to a significant reduction in the phosphate, which has bonded to the OK1 protein. The bond between the phosphate residue and an amino acid of the OK1 protein must therefore be described as heat-unstable. Furthermore, a slight reduction of the phosphate bonded to the OK1 protein can also be seen for the incubation with 0.5 M HCl and 0.5 M NaOH in comparison with phosphorylated OK1 protein incubated at 30° C. If the fact is taken into account that the quantity of OK1 protein in the autoradiography after treatment with 0.5 M NaOH is significantly less than in the samples treated with heat and acid on account of the instability of the OK1 protein compared with NaOH, then it can be concluded that the bond between the phosphate residue and an amino acid of the OK1 protein will be relatively stable with respect to bases. As the sample treated with acid contains approximately the same amounts of protein as the sample incubated at 30° C. and at 95° C., and yet has a significantly lower signal in the autoradiography than the sample treated at 30° C., it must be assumed that acid incubation conditions also split the bond between a phosphate residue and an amino acid of the OK1 protein to a certain extent. An instability in the bond between a phosphate residue and an amino acid of the OK1 protein could therefore also be established in the tests carried out. At the same time, the instability with respect to acids is significantly less labeled than the instability with respect to heat.

Bonds between the amino acids histidine and phosphate are heat-unstable, acid-unstable but base-stable (Rosenberg, 1996, Protein Analysis and Purification, Birkhäuser, Boston, 242-244). The results described above are therefore an indication that a phosphohistidine is produced by the autophosphorylation of an OK1 protein.

If recombinantly expressed OK1 protein, as described above, is incubated with ATP specifically labeled with $^{33}$P in the gamma position, then no autophosphorylation can be detected. FIG. 5A shows the amount of protein in the respective reaction preparation that can still be demonstrated by means of Western blot analysis after the appropriate incubation steps. FIG. 5B shows an autoradiography of protein from the individual reaction preparations. It can be seen that, when ATP specifically labeled in the gamma position is used, no autophosphorylation of the OK1 protein takes place, whereas, when randomised ATP is used, autophosphorylation can be demonstrated. This means that when an OK1 protein is autophosphorylated, the phosphate residue of the beta position of the ATP is covalently bonded to an amino acid of the OK1 protein.

8. Demonstration of the C-Atom Positions of the Glucose Molecules of Starch Phosphorylated by an OK1 Protein a) Manufacture of Phosphorylated Starch Phosphorylated starch was manufactured in accordance with General Methods, Item 7. For this purpose, 5 mg non-phosphorylated starch, isolated from leaves of a sex1-3 mutant of *Arabidopsis thaliana* was reacted with 25 µg purified A.t.-OK1 protein in a Preparation A, and 5 mg in vitro phosphorylated starch, originally isolated from leaves of a sex1-3 mutant of *Arabidopsis thaliana*, was reacted with 5 µg purified R1 protein in a second Preparation B. In each case, the reaction occurred in 500 µl phosphorylation buffer, which contained $^{33}$P labeled ATP in each case (ca. $2.5 \times 10^6$ cpm), by way of incubation at room temperature for 1 hour under agitation. In addition, a control preparation was used, which contained 5 mg of starch isolated from leaves of a sex1-3 mutant of *Arabidopsis thaliana* and the said phosphorylation buffer, but no protein. The control preparation was treated in exactly the same way as Preparations A and B. The individual reactions were stopped by adding 125 µl 10% SDS in each case and washed with 900 µl in each case, once with 2% SDS, five times with 2 mM ATP and twice with $H_2O$. A centrifugation was carried out after each washing step (2 minutes in an Eppendorf table centrifuge at 13,000 rpm in each case). The starch pellets obtained were re-suspended in 1 ml $H_2O$ in each case, 100 µl of each preparation was mixed after adding 3 ml of scintillation cocktail (Ready Safe™, BECKMANN), and the preparations were subsequently measured with the aid of a scintillation counter (LS 6500 Multi-Purpose Scintillation Counter, BECKMANN COULTER™).

The measurement provided the following results:

| | | |
|---|---|---|
| Control: | 63 cpm/100 µL | 630 cpm/1000 µl |
| Preparation A (OK1): | 1351 cpm/100 µl | 13512 cpm/1000 µl |
| Preparation B (R1): | 3853 cpm/100 µl | 38526 cpm/1000 µl | b) Total Hydrolysis of the P-Starch

The suspensions of Preparations A, B and C obtained in accordance with Step a) were centrifuged again (5 minutes in an Eppendorf table centrifuge at 13,000 rpm), the pellets obtained re-suspended in 90 µl 0.7 M HCl (Baker, for analysis) and subsequently incubated for 2 hours at 95° C. Preparations A, B and C were then centrifuged again (5 minutes in an Eppendorf table centrifuge at 13,000 rpm), and the supernatant transferred to a new reaction vessel. Sedimented residues of the preparations were re-suspended in 100 ml $H_2O$ in each case and after the addition of 3 ml of scintillation cocktail (Ready Safe™, BECKMANN) were measured with the help of a scintillation counter (LS 6500 Multi-Purpose Scintillation Counter, BECKMANN COULTER™). Significant amounts of radioactivity could not be demonstrated in any of the residues, which mean that all the hydrolysis products labeled with radioactive phosphate were located in the supernatant.

This was followed by neutralisation of the individual supernatants containing the hydrolysis products by the addition in each case of 30 µl 2 M NaOH (the amount of NaOH required for neutralisation was tested out in advance on blind samples): The neutralised hydrolysis products were placed on a 10 kDa Microcon filter, which had previously been rinsed twice with 200 µl $H_2O$ in each case, and centrifuged for ca. 25 minutes at 12,000 rpm in an Eppendorf table centrifuge. 10 µl were taken from the filtrate obtained (ca. 120 µl in each case) and, after the addition of 3 ml of scintillation cocktail (Ready Safe™, BECKMANN), were measured with the help of a scintillation counter (LS 6500 Multi-Purpose Scintillation Counter, BECKMANN COULTER™). The determination of the activity present in the individual preparations gave the following results:

| | | | |
|---|---|---|---|
| Preparation A (OK1): | 934 cpm/10 µl | 11,208 cpm/120 µl | 93 cpm/µl |
| Preparation B (R1): | 2518 cpm/10 µl | 30,216 cpm/120 µl | 252 cpm/µl | c) Separation of the Hydrolysis Products

The hydrolysis products obtained in accordance with Step b) were separated by means of HPAE using a Dionex system under the conditions stated above (see General Methods, Item 13c). The samples for separating the filtered supernatants of Preparations A and B obtained in accordance with Step b) were composed as follows:

Preparation A (OK1): 43 μl of the supernatant of Preparation A obtained in accordance with Step b) (equivalent to ca. 4,000 cpm), 32 μl $H_2O$, 2.5 μl 2.5 mM glucose-6-phosphate and 2.5 μl 5 mM glucose-3-phosphate (Σ Volume=80 μl).

Preparation B (R1): 16 μl of the supernatant of Preparation B obtained in accordance with Step b) (equivalent to ca. 4,000 cpm), 59 μl $H_2O$, 2.5 μl 2.5 mM glucose-6-phosphate and 2.5 μl 5 mM glucose-3-phosphate (Σ Volume=80 μl).

In each case, 60 μl, containing ca. 3,000 cpm, of the appropriate samples were injected for separation by means of HPAE. The HPAE was carried out in accordance with the conditions specified under Item 23c. After passing through the HPAE column, the elution buffer was collected in fractions, each of 1 ml. Collection of the fractions was begun 10 minutes after injecting the sample. Based on the signal received from the PAD detector used, the elution of glucose-6-phosphate was assigned to fraction 15 and the elution of glucose-3-phosphate to fraction 17. In each case, 500 μl of the individual fractions were mixed with 3 ml of scintillation cocktail (Ready Safe™, BECKMANN) and subsequently measured with the help of a scintillation counter (LS 6500 Multi-Purpose Scintillation Counter, BECKMANN COULTER™). The following measurements were obtained for the individual fractions:

TABLE 4

Measured amounts of radioactivity [cpm] in individual fractions of hydrolysis products obtained by hydrolysis of starch phosphorylated by means of an OK1 protein or R1 protein.

| | Total cpm per Fraction | |
|---|---|---|
| | Preparation A (OK1) | Preparation B (R1) |
| Fr 13 | 8.7 | 3.3 |
| Fr 14 | 13.1 | 32.2 |
| Fr 15 (G6P) | 207.3 | 1952.8 |
| Fr 16 | 399.8 | 112.3 |
| Fr 17 (G3P) | 1749.2 | 801.6 |
| Fr 18 | 196.7 | 17.3 |
| Fr 19 | 6.7 | 18.9 |
| Total | 2581.5 | 2938.3 |
| Deposit | 3000.0 | 3000.0 |
| Recovery | 86.0% | 97.9% |

Figure 5:
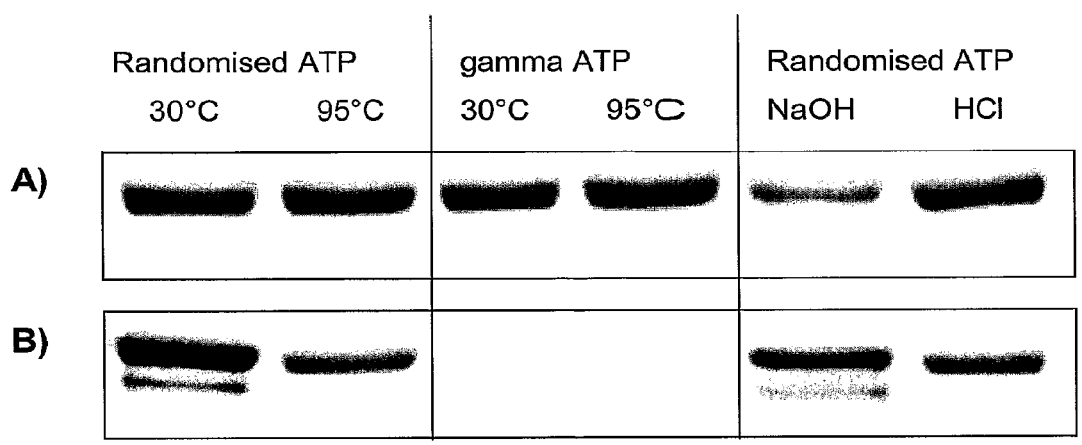
FIG. 5 Demonstration of the autophosphorylation of the OK1 protein.

The results are also shown graphically in FIG. 5.

After phosphorylation of starch catalysed by R1 protein, ca. 66% of the radioactively labeled phosphate, with respect to the total measured radioactive phosphate in the analysed fractions, eluted after hydrolysing the starch with the fraction, which contained glucose-6-phosphate as standard, and ca. 27% with the fraction, which contained glucose-3-phosphate as standard. After phosphorylation of starch catalysed by OK1 protein, ca. 67% of the radioactively labeled phosphate, with respect to the total measured radioactive phosphate in the analysed fractions, eluted after hydrolysing the starch with the fraction, which contained glucose-3-phosphate as standard, and ca. 8% with the fraction, which contained glucose-6-phosphate as standard. From this, it can be concluded that glucose molecules of the starch of R1 proteins are preferably phosphorylated in the C-6 position, whereas from OK1 proteins glucose molecules of the starch are preferably phosphorylated in the C-3 position.

9. Identification of an OK1 Protein in Rice

Using the methods described under General Methods, Items 1 to 13, it was also possible to identify a protein from *Oryza sativa* (variety M202), which transfers a phosphate residue from ATP to P-starch. The protein was designated as O.s.-OK1. Non-phosphorylated starch is not used by the O.s.-OK1 protein as a substrate, i.e. the O.s.-OK1 protein also does not need P-starch as a substrate. The nucleic acid sequence defining the identified O.s.-OK1 protein is shown under SEQ ID NO 3 and the amino acid sequence coding the O.s.-OK1 protein is shown under SEQ ID NO. 4. The amino acid sequence coding the O.s.-OK1 protein shown under SEQ ID NO 4 has an identity of 57% with the amino acid sequence coding the A.t.-OK1 protein shown under SEQ ID NO 2. The nucleic acid sequence coding the O.s.-OK1 protein shown under SEQ ID NO 3 has an identity of 61% with the nucleic acid sequence coding the A.t.-OK1 protein shown under SEQ ID NO 1.

Manufacture of the Plasmid pMI50 Containing the Nucleic Acid Sequence Coding an OK1 Protein from *Oryza sativa*

The vector pMI50 contains a DNA fragment, which codes the complete OK1 protein from rice of the variety M202.

The amplification of the DNA from rice was carried out in five sub-steps.

The part of the open reading frame from position 11 to position 288 of the sequence specified under SEQ DIE NO 3 was amplified with the help of reverse transcriptase and polymerase chain reaction using the synthetic oligonucleotides Os_ok1-R9 (GGAACCGATAATGCCTACATGCTC) and Os_ok1-F6 (AAAACTCGAGGAGGATCAATGACGTCGCTGCGGCCCCTC) as a primer on RNA of immature rice seeds. The amplified DNA fragment was cloned in the vector pCR2.1 (Invitrogen catalogue number K2020-20). The plasmid obtained was designated as pML123.

The part of the open reading frame from position 250 to position 949 of the sequence specified under SEQ DIE NO 3 was amplified with the help of reverse transcriptase and polymerase chain reaction using the synthetic oligonucleotides Os_ok1-F4 (CCAGGTTAAGTTTGGTGAGCA) and Os_ok1-R6 (CAAAGCACGATATCTGACCTGT) as a primer on RNA of immature rice seeds. The amplified DNA fragment was cloned in the vector pCR2.1 (Invitrogen catalogue number K2020-20). The plasmid obtained was designated as pML120.

The part of the open reading frame from position 839 to position 1761 of the sequence specified under SEQ DIE NO 3 was amplified with the help of reverse transcriptase and polymerase chain reaction using the synthetic oligonucleotides Os_ok1-F7 (TTGTTCGCGGGATATTGTCAGA) and Os_ok1-R7 (GACAAGGGCATCAAGAGTAGTATC) as a primer on RNA of immature rice seeds. The amplified DNA fragment was cloned in the vector pCR2.1 (Invitrogen catalogue number K2020-20). The plasmid obtained was designated as pML121.

The part of the open reading frame from position 1571 to position 3241 of the sequence specified under SEQ DIE NO 3 was amplified with the help of reverse transcriptase and polymerase chain reaction using the synthetic oligonucleotides Os_ok1-F8 (ATGATGCGCCTGATAATGCT) and Os_ok1-R4 (GGCAAACAGTATGAAGCACGA) as a primer on RNA of immature rice seeds. The amplified DNA fragment was cloned in the vector pCR2.1 (Invitrogen catalogue number K2020-20). The plasmid obtained was designated as pML119.

The part of the open reading frame from position 2777 to position 3621 was amplified with the help of polymerase chain reaction using the synthetic oligonucleotides Os_ok1-F3 (CATTTGGATCAATGGAGGATG) and Os_ok1-R2 (CTATGGCTGTGGCCTGCTTTGCA) as a primer on genomic DNA of rice. The amplified DNA fragment was cloned in the vector pCR2.1 (Invitrogen catalogue number K2020-20). The plasmid obtained was designated as pML122.

The cloning together of the sub-parts of the open reading frame of OK1 was carried out as follows.

A 700 base pair along ApaI fragment of pML120, containing part of the open reading frame of OK1, was cloned in the ApaI site of pML121. The plasmid obtained was designated as pMI47.

A 960 base pair long fragment containing the areas of vectors from pML120 and pML123 coding for OK1 was amplified by means of polymerase chain reaction. In doing so, the primers Os_ok1-F4 (see above) and Os_ok1-R9 (see above), each in a concentration of 50 nm, and the primers Os_ok1-F6 and Os_ok1-R6, each in a concentration of 500 nm, were used. The amplified DNA fragment was cloned in the vector pCR2.1 (Invitrogen catalogue number K2020-20). The plasmid obtained was designated as pMI44.

An 845 base pair long fragment of pML122 was re-amplified for introducing a XhoI site after the stop codon with the primers Os_ok1-F3 (see above) and Os_okt-R2Xho (AAAACTCGAGCTATGGCTGTGGCCTGCTTTGCA) and cloned in the vector pCR2.1 (Invitrogen catalogue number K2020-20). The plasmid obtained was designated as t pMI45.

A 1671 base pair long fragment containing part of the open reading frame of OK1 was obtained from pML119 by digesting with the restriction enzymes SpeI and PstI. The fragment was cloned in pBluescript II SK+ (Genbank Acc.: X52328). The plasmid obtained was designated as pMI46.

A 1706 base pair long fragment containing part of the open reading frame of OK1 was excised with the restriction enzymes SpeI and XhoI from pMI46 and cloned in the vector pMI45, which had been excised with the same restriction enzymes. The plasmid obtained was designated as pMI47.

A 146 base pair long fragment containing part of the open reading frame of OK1 was excised with the restriction enzymes AflII/NotI from pMI43 and cloned in the vector pMI44, which had been excised with the same restriction enzymes. The plasmid obtained was designated as pMI49.

A 1657 base pair long fragment containing part of the open reading frame of OK1 was excised with the restriction enzymes NotI and NarI from the vector pMI49 and cloned in the vector pMI47, which had been excised with the same restriction enzymes. The plasmid obtained was designated as pMI50 and contains the whole coding region of the OK1 protein identified in rice.

10. Production of an Antibody, which Specifically Recognises an Ok1 Protein

As an antigen, ca. 100 μg of purified A.t.-OK1 protein was separated by means of SDS gel electrophoresis, the protein bands containing the A.t.-OK1 protein were excised and sent to the company EUROGENTEC S.A. (Belgium), which carried out the manufacture of the antibody under contract. Next, the preimmune serums of rabbits were investigated to see whether they would already detect a protein from an A. t. total extract before immunisation with recombinant OK1. The preimmune serums of two rabbits detected no proteins in the range 100-150 kDa and were thus chosen for immunisation. 4 injections of 100 μg of protein (Tag 0, 14, 28, 56) were given to each rabbit. 4 blood samples were taken from each rabbit: (Tag 38, Tag 66, Tag 87 and the final bleeding). Serum, obtained after the first bleeding, already showed a specific reaction with OK1 antigen in Western blot. However, in all further tests, the last bleeding of a rabbit was used.

11. Production of Transgenic Rice Plants, which Exhibit Increased Activity of an OK1 Protein a) Manufacture of the Plasmid pGlo-A.t.-OK1

The plasmid pIR94 was obtained by amplifying the promoter of the globulin gene from rice by means of a polymerase chain reaction (30×20 sec 94° C., 20 sec 62° C., 1 min 68° C., 4 mM $Mg_2SO_4$) with the primers glb1-F2 (AAAA-CAATTGGCGCCTGGAGGGAGGAGA) and glb1-R1 (AAAACAATTGATGATCAATCAGACAATCACTAGAA) on the genomic DNA of rice of the variety M202 with High Fidelity Taq Polymerase (Invitrogen, catalogue number 11304-011) and cloned in pCR2.1 (Invitrogen catalogue number K2020-20). The plasmid pIR115 was obtained by cloning a synthetic piece of DNA consisting of the two oligonucleotides X1 (TGCAGGCTGCAGAGCTCCTAG-GCTCGAGTTAACACTAGTAAGCTTAATTAAGAT ATCATTTAC) and X2 (AATTGTAAATGATATCTTAAT-TAAGCTTACTAGTGTTAACTCGAGCCTAGGAGCT CTGCAGCCTGCA) in the vector pGSV71 excised with SdaI and MunI.

The plasmid pIR115 obtained was excised with SdaI, the protruding 3'-ends smoothed with T4 DNA polymerase, and a HindIII/SphI fragment from pBinAR (Höfgen and Willmitzer, 1990, Plant Science 66, 221-230) with a size of 197 base pairs, smoothed by means of T4 DNA polymerase and containing the termination signal of the octopine synthase gene from *Agrobacterium tumefaciens*, was inserted. The plasmid obtained was designated as pIR96.

The plasmid pIR103 was obtained by cloning a 986 base pair long DNA fragment from pIR94 containing the promoter of the globulin gene from rice, which was cloned in the plasmid pIR96.

pGSV71 is a derivative of the plasmid pGSV7, which is derived from the intermediate vector pGSV1. pGSV1 constitutes a derivative of pGSC1700, the construction of which has been described by Cornelissen and Vanderwiele (Nucleic Acid Research 17, (1989), 19-25). pGSV1 was obtained from pGSC1700 by deletion of the carbenicillin resistance gene and deletion of the T-DNA sequences of the TL-DNA region of the plasmid pTiB6S3.

pGSV7 contains the replication origin of the plasmid pBR322 (Bolivar et al., Gene 2, (1977), 95-113) as well as the replication origin of the *Pseudomonas* plasmid pVS1 (Itoh et al., Plasmid 11, (1984), 206). pGSV7 also contains the selectable marker gene aadA, from the transposon Tn1331 from *Klebsiella pneumoniae*, which gives resistance against the antibiotics spectinomycin and streptomycin (Tolmasky, Plasmid 24 (3), (1990), 218-226; Tolmasky and Crosa, Plasmid 29(1), (1993), 31-40).

The plasmid pGSV71 was obtained by cloning a chimeric bar gene between the border regions of pGSV7. The chimeric bar gene contains the promoter sequence of the cauliflower mosaic virus for initiating the transcription (Odell et al., Nature 313, (1985), 180), the bar gene from *Streptomyces hygroscopicus* (Thompson et al., Embo J. 6, (1987), 2519-2523) and the 3'-untranslated area of the nopaline synthase gene of the T-DNA of pTiT37 for terminating the transcription and polyadenylation. The bar gene provides tolerance against the herbicide glufosinate ammonium.

A DNA fragment, which contains the sequence of the entire open reading frame of the OK1 protein from *Arabidopsis*, was excised from the vector A.t.-OK1-pGEM, and cloned into the vector pIR103. For this purpose, the plasmid A.t.-OK1-pGEM was excised with the restriction enzyme Bsp1201, the ends were smoothed with T4-DNA polymerase, and re-excised with SalI. The DNA fragment coding the OK1 protein from *Arabidopsis thaliana* was cloned into the vector pIR103, which was excised with EcI136II and XhoI. The plasmid obtained was designated as pGlo-A.t.-OK1.

b) Transformation of Rice Plants

Rice plants (variety M202) were transformed with *Agrobacterium* (containing the plasmid pGlo-A.t.-OK1), using the method described by Hiei et al. (1994, Plant Journal 6(2), 271-282).

c) Analysis of the Transgenic Rice Plants and the Starch Synthesised from these

By way of quantitative RT PCR analysis, it was possible to identify plants, which exhibit an expression of mRNA coding A.t.-OK1 protein.

Plants, which exhibit a detectable amount of mRNA coding A.t.-OK1 protein in comparison to corresponding wild type plants, were grown in the greenhouse. Grains of these plants were harvested. Starch, isolated from these mature grains, showed an increased content of phosphate covalently bonded to the respective starch in comparison to starch, which was isolated from grains of corresponding wild type plants.

12. Production of Transgenic Potato Plants, which Exhibit Increased Activity of an OK1 Protein a) Manufacture of the Plasmid pBinB33-Hyg Starting with the plasmid pBinB33, the EcoRI-HindIII fragment containing the B33 promoter, a part of the polylinker, and the ocs-terminator were excised and spliced into the correspondingly excised vector pBIB-Hyg (Becker, 1990, Nucl. Acids Res. 18, 203). The plasmid pBinB33 was obtained by splicing the promoter of the patatin gene B33 from *Solanum tuberosum* (Rocha-Sosa et al., 1989) as a DraI fragment (nucleotide −1512-+14) into the vector pUC19 excised with Ssti, the ends of which had been smoothed with the help of the T4 DNA polymerase. This resulted in the plasmid pUC19-B33. The B33 promoter was excised from this plasmid with EcoRI and SmaI and spliced into the correspondingly excised vector pBinAR (Höfgen and Willmitzer, 1990, Plant Science 66, 221-230). This resulted in the plant expression vector pBinB33.

b) Manufacture of the Vector A.t.-OK1-pBinB33-Hyg

The coding sequence of the A.t.-OK1 protein was excised with the restriction endonucleases Bsp1201 and SalI from the plasmid A.t.-OK1-pGEM and spliced into the vector pBinB33-Hyg excised with SmaI and SalI. The plasmid obtained was designated as A.t.-OK1-pBinB33-Hyg.

c) Transformation of Potato Plants

*Agrobacterium tumefaciens* (strain GV2260) was transformed with the plasmid OK1-pBinB33-Hyg. Subsequently, potato plants of the variety Désirée were transformed with the help of the *Agrobacterium tumefaciens* containing the plasma A.t.-OK1-pBinB33-Hyg in accordance with the method described by Rocha-Sosa et al. (EMBO J. 8, (1989), 23-29), and the plants were regenerated. The plants obtained from this transformation event were designated 385JH.

d) Analysis of the Transgenic Potato Plants and the Starch Synthesised from these By means of Northern Blot analysis, it was possible to identify plants of the transformation event 385JH, which exhibit an expression of mRNA, coding the A.t.-OK1 protein.

A Western Blot analysis, which was performed with the antibody described under Example 10, confirmed, that plants of the transformation event 385JH, in which mRNA of the heterologously expressed OK1 protein was detected, also exhibit an increased quantity of OK1 protein in comparison to wild type plants that have not been transformed. FIG. 7 exemplary shows the detection of the A.t.-OK1 Protein in single plants from the transformation event 385JH by means of Western Blot analysis. For induction of the B33 Promotor in leaf tissue single lines of the transformation event 385JH were cultivated on solidified Musharige Skoog medium containing 100 mM sucrose in tissue culture for two days. After harvest protein extracts were produced from leaf tissue of these plants according to the method described under General Methods, Item 1a). After separation of the proteins by means of denaturing polyacrylamide gel electrophoreses 40 μg protein extract of each line was analysed by means of Western Blot analysis using the antibody described under Examples, Item 10. As control samples, protein extracts from *Arabidopsis* plants and from potato wildtype plants (cv Désirée) were also analysed. Plants, which exhibit an increased quantity of OK1 protein and a detectable quantity of A.t.-OK1 protein coding mRNA, were grown in the greenhouse. Starch, which was isolated from tubers of these plants, showed an increased content of phosphate bonded covalently to the corresponding starch.

13. Production of Transgenic Maize Plants, which Exhibit Increased Activity of an OK1 Protein a) Manufacture of the Plasmid pUbi-A.t.-OK1

First the plasmid pIR96 was manufactured. The plasmid pIR96 was obtained by cloning a synthetic piece of DNA consisting of the two oligonucleotides X1 (TGCAGGCTG-CAGAGCTCCTAGGCTCGAGTTAACACTAGTAAGCTT AATTAAGAT ATCATTTAC) and X2 (AATTGTAAAT-GATATCTTAATTAAGCTTACTAGTGT-TAACTCGAGCCTAGGAGCT CTGCAGCCTGCA) into the vector pGSV71 excised with SdaI and MunI. The plasmid obtained was excised with SdaI and the protruding 3'-ends were smoothed with T4 DNA polymerase. The plasmid obtained was excised with SdaI, the protruding 3'-ends were smoothed with T4 DNA polymerase, and a 197 base pair large HindIII/SphI fragment from pBinAR, smoothed with T4 DNA polymerase (Höfgen and Willmitzer, 1990, Plant Science 66, 221-230), and containing the termination signal of the octopine synthase gene from *Agrobacterium tumefaciens*, was inserted. The plasmid obtained was designated as pIR96.

pGSV71 is a derivative of the plasmid pGSV7, which is derived from the intermediate vector pGSV1. pGSV1 constitutes a derivative of pGSC1700, the construction of which has been described by Cornelissen and Vanderwiele (Nucleic Acid Research 17, (1989), 19-25). pGSV1 was obtained from pGSC1700 by deletion of the carbenicillin resistance gene and deletion of the T-DNA sequences of the TL-DNA region of the plasmid pTiB6S3.

pGSV7 contains the replication origin of the plasmid pBR322 (Bolivar et al., Gene 2, (1977), 95-113) as well as the replication origin of the *Pseudomonas* plasmid pVS1 (Itoh et al., Plasmid 11, (1984), 206). pGSV7 also contains the selectable marker gene aadA, from the transposon Tn1331 from *Klebsiella pneumoniae*, which gives resistance against the antibiotics spectinomycin and streptomycin (Tolmasky, Plasmid 24 (3), (1990), 218-226; Tolmasky and Crosa, Plasmid 29(1), (1993), 31-40). The plasmid pGSV71 was obtained by cloning a chimeric bar gene between the border regions of pGSV7. The chimeric bar gene contains the promoter sequence of the cauliflower mosaic virus for initiating the transcription (Odell et al., Nature 313, (1985), 180), the bar gene from *Streptomyces hygroscopicus* (Thompson et al., Embo J. 6, (1987), 2519-2523) and the 3'-untranslated area of the nopaline synthase gene of the T-DNA of pTiT37 for terminating the transcription and polyadenylation. The bar gene provides tolerance against the herbicide glufosinate ammonium.

A 1986 base pair long fragment containing the promoter of the polyubiquitin gene from maize (Genes from Maize (Gens aus Mais) (EMBL Acc.: 94464, Christensen et al., 1992, Plant Mol. Biol. 18: 675-689) was cloned as a PstI fragment into pBluescript II SK+. The plasmid obtained was designated as pSK-ubq.

The plasmid A.t.-OK1-pGEM was excised with the restriction enzyme Bsp120I, the ends were smoothed with T4-DNA polymerase, and it was re-excised with SacI. The DNA fragment coding the OK1 protein from *Arabidopsis thaliana* was cloned into the plasmid pSK-ubq, which was excised with SmaI and SacI. The plasmid obtained was designated as pSK-ubq-ok1.

A fragment was isolated from the plasmid pSK-ubq-ok1, which contains the ubiquitin promoter from maize and the entire open reading frame for the A.t.-OK1 protein from *Arabidopsis thaliana*. For this purpose, the plasmid was excised with the restriction enzyme Asp718I, the ends were filled with T4 DNA polymerase, and it was re-excised with SdaI. The 5799 base pair large fragment obtained was cloned into the plasmid pIR96 excised with EcoRV and PstI. The plasmid obtained from this cloning was designated as pUbi-A.t.-OK1.

b) Transformation of Maize Plants

Maize plants were transformed with the plasmid pUbi-A.t.-OK1 using the method described under General Methods, Item 17.

c) Analysis of the Transgenic Maize Plants and the Starch Synthesised from these Using Northern Blot analysis, plants could be identified, which exhibit an expression of mRNA, coding the A.t.-OK1 protein.

Maize plants, which exhibit a detectable amount of A.t.-OK1 protein coding mRNA in comparison to corresponding wild type plants, were grown in the greenhouse. Single grains of these plants were harvested. Starch, isolated from these grains, showed an increased content of phosphate covalently bonded to the respective starch in comparison to starch, which is isolated from grains of corresponding wild type plants.

14. Manufacture of Transgenic Wheat Plants, which Exhibit Increased Activity of an OK1 Protein a) Manufacture of a Plasmid for the Transformation of Wheat Plants pMCS5 (Mobitec, www.mobitec.de) was digested with BglII and BamHI and re-inserted. The plasmid contained was designated as pML4.

The nos terminator from *Agrobacterium tumefaciens* (Depicker et al., 1982, Journal of Molecular and Applied Genetics 1: 561-573) was amplified with the primers P9 (ACTTCTgCAgCggCCgCgATCgTTCAAACATTTggCAATAAAg TTTC) and P10 (TCTAAgCTTggCgCCgCTAgCAgATCTgATCTAgTAACATAgATgACACC) (25 cycles, 30 sec 94° C., 30 sec 58° C., 30 sec 72° C.), digested with HindIII and PstI, and cloned into the plasmid pML4 having been excised with the same enzymes. The plasmid contained was designated as pML4-nos. A 1986 base pair long fragment containing the promoter of the polyubiquitin gene from maize (Genbank Acc.: 94464, Christensen et al., 1992, Plant Mol. Biol. 18: 675-689) and the first intron of the same gene, shortened through digestion by ClaI and re-insertion, were cloned into this vector. The plasmid contained was designated as pML8.

The entire open reading frame of OK1 from *Arabidopsis thaliana* was cloned into the plasmid pML8. In order to this, the corresponding fragment with Bsp120/NotI was excised from A.t.-OK1-pGEM, and spliced into the NotI site of pML8 in an "in sense" orientation.

A fragment for the transformation of wheat plants can be excised from the obtained vector pML8-A.t.-OK1 with the restriction enzymes AvrII and SwaI, which contains the promoter of the polyubiquitin gene from maize, the entire open reading frame of OK1 from *Arabidopsis thaliana*, and the nos terminator from *Agrobacterium tumefaciens*.

b) Transformation of Wheat Plants

Wheat plants of the Florida variety were transformed with a fragment purified from an agarose gel, which was excised with the restriction enzymes AvrII and SwaI from the plasmid pML8-A.t.-OK1, and which contains the promoter of the polyubiquitin gene from maize, the entire open reading frame of OK1 from *Arabidopsis thaliana*, and the nos terminator from *Agrobacterium tumefaciens*, and with the plasmid pGSV71 using the biolistic method according to the method described by Becker et al. (1994, Plant Journal 5, 299-307).

c) Analysis of the Transgenic Wheat Plants and the Starch Synthesised from these Starch was isolated from mature grains of the T0 plants obtained from the transformation, and the content of phosphate covalently bonded to the starch was determined. The phosphate content of the starch, which was isolated from individual grains, was clearly higher than in the case of the starch, which was isolated from grains of corresponding wild type plants.

The invention claimed is:

1. A genetically modified plant cell comprising at least one foreign nucleic acid molecule that encodes an OK1 protein, wherein the at least one foreign nucleic acid molecule comprises:
   a) a nucleic acid molecule coding a protein having the amino acid sequence of SEQ ID NO: 2;
   b) a nucleic acid molecule coding a protein having an amino acid sequence with at least 95% identity to SEQ ID NO: 2;
   c) a nucleic acid molecule comprising the nucleotide sequence of SEQ ID NO: 1, or the complementary sequence thereof; or
   d) a nucleic acid molecule having at least 95% identity to the nucleic acid molecule of a) or c).

2. The genetically modified plant cell according to claim 1, wherein the at least one nucleic acid molecule comprises a nucleic acid coding a protein having the amino acid sequence of SEQ ID NO: 2.

3. The genetically modified plant cell according to claim 1, wherein the genetically modified plant cell comprises a nucleic acid molecule comprising the nucleotide sequence of SEQ ID NO: 1, or the complementary sequence thereof.

4. The genetically modified plant cell according to claim 1, wherein said plant cell synthesises a modified starch in comparison to the corresponding wild type plant cells that have not been genetically modified.

5. The genetically modified plant cell according to claim 4, wherein the modified starch has an increased starch phosphate content and/or a modified phosphate distribution.

6. The genetically modified plant cell according to claim 5, wherein the modified starch has a modified C-3 phosphate to C-6 phosphate ratio.

7. The genetically modified plant cell according to claim 1, wherein said plant cell synthesises a modified starch in comparison to the corresponding wild type plant cells that have not been genetically modified.

8. The genetically modified plant cell according to claim 7, wherein the modified starch has an increased starch phosphate content and/or a modified phosphate distribution.

9. The genetically modified plant cell according to claim 8, wherein the modified starch has a modified C-3 phosphate to C-6 phosphate ratio.

10. A plant comprising one or more genetically modified plant cells according to claim 1.

11. A plant according to claim 10, wherein said plant is a starch-storing plant.

12. A plant according to claim 11, wherein said starch-storing plant is a maize plant or wheat plant.

13. A plant comprising one or more genetically modified plant cells according to claim 1.

14. A plant according to claim 13, wherein said plant is a starch-storing plant.

15. A plant according to claim 14, wherein said starch-storing plant is a maize plant or wheat plant.

16. Propagation material comprising the genetically modified plant cell according to claim 1.

17. Propagation material comprising the genetically modified plant cell according to claim 1.

18. A harvestable plant part of a plant comprising the genetically modified plant cell according to claim 1.

19. A harvestable plant part of a plant comprising the genetically modified plant cell according to claim 1.

20. A nucleic acid molecule coding a protein with the enzymatic activity of an OK1 protein, comprising:
   a) a nucleic acid molecule coding a protein having the amino acid sequence of SEQ ID NO: 2; or
   b) a nucleic acid molecule comprising the nucleotide sequence of SEQ ID NO: 1, or the complementary sequence thereof.

21. The nucleic acid molecule according to claim 20, wherein said nucleic acid molecule is a nucleic acid molecule coding a protein having the amino acid sequence of SEQ ID NO: 2.

22. A recombinant nucleic acid molecule comprising a nucleic acid molecule according to claim 20.

23. A vector comprising a nucleic acid molecule according to claim 20.

24. The vector according to claim 23, wherein the nucleic acid molecule is linked with at least one regulatory sequence, which initiates transcription in prokaryotic or eukaryotic cells.

25. A host cell, which is genetically modified with a nucleic acid molecule according to claim 20.

26. A composition comprising a nucleic acid molecule according to claim 20.

27. A method comprising using the composition of claim 26 to identify a plant cell having an increased activity of at least one OK1 protein in comparison to wild type plant cells that have not been genetically modified.

28. A vector comprising a recombinant nucleic acid molecule according to claim 22.

29. A host cell, which is genetically modified with a recombinant nucleic acid molecule according to claim 22.

30. A host cell, which is genetically modified with a vector according to claim 23.

31. A host cell, which is genetically modified with a vector according to claim 28.

32. A composition comprising a recombinant nucleic acid molecule according to claim 22.

33. The nucleic acid molecule according to claim 20, wherein said nucleic acid molecule comprises the nucleotide sequence of SEQ ID NO: 1, or the complementary sequence thereof.

34. A method of manufacturing a genetically modified plant, comprising:
   a) introducing at least one foreign nucleic acid molecule that encodes an OK1 protein, wherein the at least one foreign nucleic acid molecule comprises:
      i) a nucleic acid molecule coding a protein having the amino acid sequence of SEQ ID NO: 2;
      ii) a nucleic acid molecule coding a protein having an amino acid sequence with at least 95% identity to SEQ ID NO: 2;
      iii) a nucleic acid molecule comprising the nucleotide sequence of SEQ ID NO: 1, or the complementary sequence thereof; or
      iv) a nucleic acid molecule having at least 95% identity to the nucleic acid molecule of i) or b) regenerating a plant from one or more plant cells from step a); and c) optionally producing one or more additional plants from a plant according to step b).

35. The method according to claim 34, wherein said nucleic acid molecule is a nucleic acid molecule coding a protein having the amino acid sequence of SEQ ID NO: 2.

36. The method according to claim 34, wherein said nucleic acid molecule comprises the nucleotide sequence of SEQ ID NO: 1, or the complementary sequence thereof.

37. The method according to claim 34, wherein said genetically modified plant cell synthesises a modified starch in comparison to the corresponding wild type plant cells that have not been genetically modified.

38. The method according to claim 37, wherein the modified starch has an increased starch phosphate content and/or a modified phosphate distribution.

39. The method according to claim 38, wherein the modified starch has a modified C-3 phosphate to C-6 phosphate ratio.

40. The method according to claim 34, wherein said genetically modified plant cell synthesises a modified starch in comparison to the corresponding wild type plant cells that have not been genetically modified.

41. The method according to claim 40, wherein the modified starch has an increased starch phosphate content and/or a modified phosphate distribution.

42. The method according to claim 41, wherein the modified starch has a modified C-3 phosphate to C-6 phosphate ratio.

43. The genetically modified plant cell of claim 1, wherein the OK1 protein further comprises SEQ ID NO: 5.

44. The nucleic acid molecule of claim 20, wherein the OK1 protein further comprises SEQ ID NO: 5.

45. The method of claim 34, wherein the OK1 protein further comprises SEQ ID NO: 5.

46. The method of claim 27, further comprising hybridizing the nucleic acid molecule in said composition with a nucleic acid from a plant cell.

\* \* \* \* \*